(12) United States Patent
Price

(10) Patent No.: US 6,812,034 B2
(45) Date of Patent: Nov. 2, 2004

(54) FETUIN-MGP-MINERAL COMPLEX IN SERUM ASSAYED TO DETERMINE CALCIFICATION RISK

(75) Inventor: Paul A. Price, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 10/045,596

(22) Filed: Oct. 18, 2001

(65) Prior Publication Data

US 2003/0027211 A1 Feb. 6, 2003

Related U.S. Application Data

(63) Continuation-in-part of application No. 09/477,505, filed on Jan. 4, 2000, now abandoned.

(51) Int. Cl.$^7$ .......................... G01N 33/20; G01N 33/00
(52) U.S. Cl. ........................................... 436/79; 436/87
(58) Field of Search ..................................... 436/79, 87

(56) References Cited

U.S. PATENT DOCUMENTS

| | | |
|---|---|---|
| 5,183,815 A | 2/1993 | Saari et al. |
| 5,196,409 A | 3/1993 | Breuer et al. |
| 5,294,608 A | 3/1994 | Lang et al. |
| 5,395,826 A | 3/1995 | Naumann |
| 5,403,824 A | 4/1995 | D'Souza |
| 5,403,829 A | 4/1995 | Lehtinen |
| 5,409,911 A | 4/1995 | Tyler |
| 5,428,181 A | 6/1995 | Sugioka |
| 5,498,617 A | 3/1996 | Naumann |
| 5,506,211 A | 4/1996 | Barnes |
| 5,616,174 A | 4/1997 | Hayashi |
| 5,733,564 A | 3/1998 | Lehtinen |
| 5,763,611 A | 6/1998 | Kaas |
| 5,856,314 A | 1/1999 | Kaas |
| 5,898,038 A | 4/1999 | Yallampalli |
| 5,945,412 A | 8/1999 | Fuh |

OTHER PUBLICATIONS

L. Ahrengart et al. (1986) "Prevention of Ectopic Bone Formation by Local Application of Ethane–1–hydroxy, 1–diphisphane (EHDP): An Experimental Study in Rabbits", JOR 4:18–26.
Alatli et al. (1996) "Root surface defects in rat molar induced by 1–dydroxyethylidene–1, 1–bisphosphanate", Acta Odontologica Scandinavica 54: 59–65.
V. N. Antic et al. (1996) "Effect of Bisphosphonates on the Increase in Bone Resorption Induced by a Low Calcium Diet", Calcified Tissue Institute 58:443–448.
Baumann et al. (1978) "Biochemical and clinical effects of ethane–1–dydroxy–,1–diphosphanate in calcium nephrolithiasis" Clinical Science and Molecular Medicine 54: 509–516.
Block M.D. et al. (1998) Association of Serum Phosphorus and Calcium X Phosphate Product With Mortality Risk in Chronic Hemodialysis Patients: A National Study vol. 31: 4: 607–617.

Blomen (1995) Bijvoet OLM et al. Bisphosphonate on Bones, Elsevier, Amsterdam 111–124.
Briner et al. (1971) "The control of dental calculus in experimental animals", vol. 21: 1 : 61–73.
Casey et al.(1972) "Polyribosomes in Rat Liver Slices During Incubation in Vitro", Specialia 15:2.
Coates et al. (1998) "Cutaneous Necrosis from Calcific Uremic Arteriolopathy", American Journal of Kidney Diseases, vol. 32: 3: 384–391.
Cohen et al. "Bisphosphonates and Tetracycline: Experimental Models for Their Evaluation in Calcium–Related Disorders", Pharmaceutical Research 15:4:606–613.
Dare et al. (1993) "New Observations on the Etiology of Aortic Valve Disease: A Surgical Pathologic Study of 236 Cases of 1990", Human Pathology, vol. 24 : 12: 1330–1338.
Daoud et al. (1987) "The Effect of Ethane–1–Hydroxy–1, 1–Diphosphonate (EHDP) on Necrosis of Atherosclerotic Lesions", Artherosclerosis 67: 41–48.
Finerman (1981) "Heterotopic Ossification Following Hip Replacement or Spinal Cord Injury. Two Clinical Studies with EHDP", Metab. Bone Dis. & Rel. Res. 4&5: 337–342.
Fleisch et al. (1970) "The Inhibitory Effect of Phosphates on the Formation of Calcium Phosphate Crystals in Vitro and on Aortic and Kidney Calcification in Vivo", Europ. J. Clin. Invest. 1: 12–18.
Fleisch (1997) "Bisphophonates: Preclinical Aspects and Use in Osteoporosis", The Finnish Medical Society DUIODECIM, Ann Med. 29: 55–62.
Fleisch (1998) "Bisphosphonates: Mechanisms of Action", Endocrine Reviews 19(1): 80–100.
Fleisch (1999) "Bisphosphanates: A New Class of Drugs in Diseases of Bone and Calcium Metabolism", Calcium in Drug Actions 21:441–466.
Flora (1980) "Comparative Skeletal Effects of Two Diphosphanates in Dogs", Metab. Bone Dis. Et Rel. vol. 2S 389–407.

(List continued on next page.)

Primary Examiner—Sandra E Saucier
(74) Attorney, Agent, or Firm—Tom Hunter; Quine I.P. Law Group, PC.

(57) ABSTRACT

This invention provides methods of inhibiting calcification of a soft tissue (e.g., an artery, a heart valve, an atherosclerotic plaque, a cancer, a kidney, a prostate, skin, muscle, cartilage, viscera, and heart muscle) in a mammal. These methods involve inhibiting osteoclastic bone resorption in said mammal (e.g., a mammal diagnosed as having or at risk for a pathology characterized by calcification of a soft tissue). The inhibition is preferably by administration of a bisphosphonate to the mammal in a concentration sufficient to inhibit bone resorption without inhibiting bone mineralization. The methods of this invention can also be used to mitigate a symptom of atherosclerosis in a mammal. Such methods involve inhibiting osteoclastic bone resorption in the mammal. In preferred embodiment, the inhibiting is by administration of a bisphosphonate to the mammal in a concentration sufficient to inhibit bone resorption without inhibiting bone mineralization

12 Claims, 20 Drawing Sheets

OTHER PUBLICATIONS

Goldsmith (1997) "Vascular Calcification in Long–Term Haemodialysis Patients in a Single Unit: A Retrospective Analysis", Nephron 77: 37–43.

Golomb (1986) "Controlled Release of Diphosphonate to Inhibit Bioprosthetic Heart Valve Calcification: Dose–Response and Mechanistic Studies", Journal of Controlled Release 4:181–194.

Hafner (1995) "Uremic Small–Artery Disease with Medical Calcification and Intimal Hyperplasia (so–called calciphylaxis): A complication of chronic renal failure and benefit from parathyroidectomy", Journal of the American Academy of Dermatology 33:954–962.

Hollander et al. (1979) "Effects of Anticalcifying and Anti-fibrobrotic Drugs on Pre–Established Atherosclerosis in the Rabbit", Arthrosclerosis 33: 111–123.

King (1971) "Effect of Disodium Ethane–1–Hydroxy–1, 1–Disphosphonate on Bone Formation", Clin. Oth & Rel. Res. 78:251–269.

Kramsch et al. (1978) "The Effect of Agents Interfering with Soft Tissue Calcification and Cell Proliferation on Calcific Fibrous–Fatty Plaques in Rabbits", Circulation Research 42(4):562–572.

Kramsch (1981) "Atherosclerosis: Prevention by Agents Not Affecting Abnormal Levels of Blood Lipids", Science vol. 213: 1511–1512.

Larsson (1974) "The Short–Term Effects of High Doses of Ethylene–1–Hydroxy–1, 1–Diphosphonate upon Early Dentin Formation", Calc. Tiss. Res. 16: 109–127.

Levy et al. (no date) "Inhibition of Calcification of Bioprosthetic Heart Valves by Local Controlled–Release Diphosphonate", Science 228: 190–192.

Mori et al. (1998) "Expression of Matrix Gla Protein (MGP) in an In Vitro Model of Vascular Calcification", FEBS Letters 443: 19–22.

Ogawa (1980) "NaF, SrCI2, EHDP", Jpn. J. Oral Biol., 55:199–226–No Translation.

Plasmans (1978) "The Effect of Ethane–1–Hydroxy–1, 1–Diphosphonic Acid (EHDP) on Matrix Induced Ectopic Bone Formation", Clin. Orth. & Rel. Res. 132: 233–243.

Price (1998) "Warfarin Causes Rapid Calcification of the Elastic Lamellae in Rat Arteries and Heart Valves", Arterioscler Thromb Vasc. Biol. 18: 1400–1407.

Reiner et al. (no date) Diphosphonate Treatment in Myositis Ossifacans Progressiva (no publication).

Rosenblum et al. (1975) "The Effect of Disodium Ethane–1–Hydroxy–1, 1–Diphosphonate (EHDP) On a Rabbit Model of Athero–Arterioscloerosis", Artherosclerosis 22:411–424.

Rosenblum (1977) "The Effects of Various Diphosphonates on a Rat Model of Cardiac Calciphylaxis", Calif. Tiss. Res. 23: 151–159.

Schenk (1973) "Effect of Ethane–1–Hydroxy–1, 1–Diphosphonate (EHDP) and Dichloromethylene Diphosphonate (CI2MDP) on the Calicification and Resorption of Cartilage and Bone in the Tibial Epiphysis and Metaphysis of Rats", Calc. Tiss. Res. 11: 196–214.

Slooff (no date) "The use of a Diphosphonate in Para–Articular Ossifications after Total Hop Replacement. A Clinical Study", Prothese Totale De Genou Guepar.

Takeo (1989) "Functional Changes of Aorta with Massive Accumulation of Calcium", Athersclerosis 77: 175–181.

Takeo (1991) "Alterations in Cardiac Function and Subcellular Membrane Activities after Hypervitaminosis D3", Molec. & Cellu. Biochem. 107: 169–183.

Thomas et al. (1985) "Results of the Administration of Diphosphonate for the Prevention of Heterotopic Ossification after Total Hip Arthroplasty", Journ. Of Bone and Joint Surgery 3: 400–403.

Ylitalo et al. (1994) "Effects of Clodronate(Dichloromethylene Bisphosphonate) on the Development of Experimental Atherosclerosis in Rabbits", J. Lab. Clin. Med. 123: 769–776.

Weile et al. (1990) "Effects of Single Doses of 1–Hydroxyethylidene–1, 1–Bisphosphonate on the Mineralizing Front of Rat Incisor Enamel: A Microradiographic and Scanning Electron Microscopic Study", Arch. Oral. Biol. 35(11) 857–867.

Zhu et al. (1994) "Effects of Etidronate and Lovastatin on the Regression of Atherosclerosis in Choletero–Fed Rabbits", Cardiology 85: 370–377.

NO ALENDRONATE

ALENDRONATE AT
0.25 mg P/kg/day

ALENDRONATE FOR ALL 8 DAYS

ALENDRONATE FOR LAST 2 DAYS ONLY

ALENDRONATE FOR FIRST 6 DAYS

NO ALENDRONATE

NO BISPHOSPHONATE

IBANDRONATE AT 0.01 mg P/kg/day

ALENDRONATE AT 0.25 mg P/kg/day

NO
ALENDRONATE

ALENDRONATE AT
0.025 mg P/kg/day

ALENDRONATE AT
0.25 mg P/kg/day

FETUIN-MGP-MINERAL COMPLEX IN SERUM ASSAYED TO DETERMINE CALCIFICATION RISK

CROSS-REFERENCE TO RELATED APPLICATIONS

This application is a continuation-in-part of U.S. Ser. No. 09/477,505, filed on Jan. 4, 2000, (now abandoned), which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by US Public Health Service Grant AR25921. The Government of the United States of America may have certain rights in this invention.

FIELD OF THE INVENTION

This invention relates to modulators of soft tissue calcification. In particular, this invention relates to the discovery that inhibition of bone resorption will also result in the inhibition of calcification of soft tissues.

BACKGROUND OF THE INVENTION

The bisphosphonates have been known to chemists since the middle of the 19th century, when the first synthesis occurred in 1865 in Germany (Menschutkin (1865) *Ann. Chem. Pharm.*, 133: 317–320). Bisphosphonates were used in industry, mainly as corrosion inhibitors or as complexing agents in the textile, fertilizer and oil industries. Their ability to inhibit calcium carbonate precipitation, similar to polyphosphates was put to use in the prevention of scaling (Blomen (1995) Pages 111–124 in Bijvoet OLM et al., eds. *Bisphosphonate on Bones*, Elsevier, Amsterdam).

More recently, bisphosphonates have been developed as drugs for use in various diseases of bone, tooth, and calcium metabolism. The bisphosphonates have two fundamental previously known biological effects: inhibition of calcification when given at high doses and inhibition of bone resorption.

Bisphosphonates have been shown to efficiently inhibit ectopic calcification in vivo. Thus, among others, they prevent experimentally induced calcification of many soft tissues when given both parentally and orally (Fleisch et al. (1970) *Eur. J. Clin. Invest.*, 1: 12–18; Rosenblum et al. (1977) *Calcif. Tissue Res.*, 23: 151–159). In contrast to pyrophosphate, which acts only when given parenterally, bisphosphonates are active when administered orally. They have also been shown to have activity when released locally from various matrices (Levy wet al. (1985) *Science*, 228: 190–192; Golomb et al. (1986) *J. Contr. Rel.*, 4: 181–194). In addition, topical administration can lead to a decreased formation of dental calculus (Briner et al. (1971) *Int. Dent. J.* 21: 61–73). This effect is used to prevent tartar formation in humans by the addition of bisphosphonates to toothpastes. In addition, certain bisphosphonates inhibit ectopic ossification when given systemically (Plasmans et al. (1978) *Clin. Orthop.*, 132: 233–243) or locally (Ahrengart and Lindgren (1986) *J. Orthop., Res.* 4: 18–26).

Of the bisphosphonates, etidronate has been used in humans to prevent ectopic calcification and ossification. Unfortunately with respect to calcification, the results have been disappointing. In conditions such as scleroderma, dermatomyositis, and calcinosis universalis, the results have proven at best inconclusive (Fleisch (1988) Pages 440–466 in Baker PF (ed) *Handbook of Experimental Pharmacology*, Springer-Verlag, N.Y.). In urolithiasis, the dose that was believed to potentially be effective was such that normal bone mineralization was inhibited (Baumann et al. (1978) *Clin. Sci. Mol. Med.*, 54: 509–516). Other reports also describe the effects of bisphosphonates on ectopic ossification, especially fibrodysplasia ossificans progressiva (Reiner et al. (1980) Pages 237–241 in Caniggia A (ed) *Etidronate*. Instituto Gentili, Pisa.), and ossification after spinal cord injury, cranial trauma, and total hip replacement (Slooff et al. (1974) *Acta Orthop. Belg.* 40: 820–828; Finerman and Stover (1981) *Metab. Bone Dis. Relat. Res.*, 4: 337–342; Thomas and Amstutz (1985) *J. Bone Joint Surg. (Am)* 67: 400–403). While such studies have raised the hope that bisphosphonates might be used clinically to inhibit various types of calcifications, when administered in doses approximating those that inhibit soft tissue calcification, bisphosphonates have impaired the mineralization of normal calcified tissues such as bone and cartilage (King et al. (1971) *Clin. Orthop.*, 78: 251–270; Schenk et al. (1973) *Calcif. Tissue Res.*, 11: 196–214; Flora et al. (1980) *Metab. Bone Dis. Rel. Res.*, 2: 389–407), and, when given in higher amounts, also dentine (Larsson (1974) *Calcif. Tiss. Res.*, 16: 109–127), enamel (Ogawa (1980) *Jpn. J. Oral Biol.*, 22: 199–226; Weile et al. (1990) *Arch. Oral Biol.*, 22: 199–226), and cementum (Alatli and Hammarstrom (1996) *Acta Odontol. Scand.*, 54: 59–65).

Moreover, while the different bisphosphonates vary greatly in their activity in bone resorption, they do not vary greatly in the inhibition of mineralization. For most bisphosphonates, the effective daily dose was believed to be on the order of 5–20 mg of compound phosphorus per kg, administered parenterally, suggesting that the bisphosphonates inhibit calcification at high doses via a common mechanism.

Thus, although bisphosphonates have proven successful when administered to humans or other mammals to inhibit bone resorption, the propensity to inhibit the calcification of normal bone when administered at dosages believed high enough to inhibit ectopic calcification, has hampered the therapeutic use of bisphosphonates in the treatment of ectopic calcifications.

SUMMARY OF THE INVENTION

This invention provides new approaches to the treatment of ectopic calcifications and various arteriioscleroses (e.g., atherosclerosis). The methods of this invention are premised, in part, on the discovery that agents that inhibit bone resorption will also inhibit ectopic calcification and/or plaque formation and related pathologies associated with arteriosclerosis. Without being bound to a particular theory, it is believed that the process of bone resorption, delivers solubilized calcium (e.g. in a calcium phosphate/protein complex) to the blood where it can travel to sites far removed from bone and there act as a nucleation complex for the formation of ectopic calcifications or atherosclerotic plaques and/or contribute to the formation of an existing calcium deposition.

Various agents, in particular bisphosphonates, are often able to inhibit bone resorption at far lower dosages than the dosages at which they have been observed to inhibit bone calcification. It was believed that the effect on bone resorption was mediated via a biological/cellular mechanism and the effect on bone calcification was mediated by a physiochemical mechanism (e.g. direct binding to hydroxyapatite).

Similarly, it was believed that bisphosphonates could inhibit ectopic calcification by the same physio-chemical mechanism as that used to inhibit bone mineralization. Consequently it was believed that although high dosages of bisphosphonates could inhibit ectopic calcification, this approach had little therapeutic value because of the adverse effect on bone mineralization.

The discovery of this invention, that ectopic calcification can be inhibited by inhibition of bone resorption allows the treatment of pathologies associated with undesired calcification at low dosages, e.g. at dosages that do not adversely effect bone mineralization. Thus, in view of the discoveries described herein, a new therapeutic modality is provided for the alleviation of ectopic calcifications and/or arteriosclerotic plaque formation.

Thus, in one embodiment, this invention provides methods of inhibiting calcification of a soft tissue (e.g., an artery, a heart valve, an atherosclerotic plaque, a cancer, a kidney, a prostate, skin, muscle, cartilage, viscera, and heart muscle) in a mammal. These methods involve inhibiting osteoclastic bone resorption in said mammal (e.g., a mammal diagnosed as having or at risk for a pathology characterized by calcification of a soft tissue) The inhibition is preferably by administration of a bisphosphonate to the mammal in a concentration sufficient to inhibit bone resorption without inhibiting bone mineralization. In preferred embodiments, the bisphosphonate effects a significant reduction of bone resorption at a concentration at least 10-fold, more preferably at least 100-fold, and most preferably at least 1000-fold lower than the concentration at which said bisphosphonate effects a significant reduction of bone mineralization (preferably in the same assay and at the same confidence level). The bisphosphonate may be administered at a dosage at least 10-fold, more preferably at least 100-fold, and most preferably at least 1000-fold lower than concentration at which said bisphosphonate effects a significant reduction of bone mineralization (preferably in the same assay and at the same confidence level). Particularly preferred bisphosphonates include, but are not limited to alendronate, ibandronate, zoledronate, incadronate, risedronate, EB-1053, neridronate, olpadronate, pamidronate, YH 529, tiludronate, and clodronate.

In another embodiment this invention provides methods of method of inhibiting calcification of soft tissue (e.g., an artery, a heart valve, an atherosclerotic plaque, a cancer, a kidney, a prostate, skin, muscle, cartilage, viscera, and heart muscle) in a mammal diagnosed as having or at risk for a pathology characterized by calcification of a soft tissue. These methods involve administering to the animal a low dosage of a bisphosphonate, where the low dosage is sufficient to inhibit the calcification, but below the dosage of the bisphosphonate that inhibits normal bone mineralization. Preferred bisphosphonates and dosages include those described above. In one embodiment the bisphosphonate is alendronate administered at a dosage ranging from the minimum dose that produces a detectable inhibition of bone resorption up to 0.5 mg P/kg/day. In another embodiment, the bisphosphonate is alendronate administered to humans at an oral dosage ranging from 5 mg to 40 mg per day. In still another embodiment, the bisphosphonate is ibandronate administered at a dosage ranging from the minimum dose that produces a detectable inhibition of bone resorption up to 0.5 mg P/kg/day, preferably at an intra venous dosage of 1 mg per day. In still yet another embodiment, the bisphosphonate is zoledronate, incadronate, risedronate, EB-1053, neridronate, olpadronate, pamidronate, YH 529, tiludronate, or clodronate administered at a dosage ranging from the minimum dose that produces a detectable inhibition of bone resorption up to 0.5 mg P/kg/day. Preferred modes of administration include, but are not limited to, transdermal patch, orally, intravenous injection, subcutaneous injection, and intramuscular injection. The bisphosphonate can be administered as a prophylactic or a therapeutic treatment.

This invention also provides a method of mitigating the symptoms of a disease in a mammal that involves calcification of a soft tissue (an artery, a heart valve, an atherosclerotic plaque, a cancer, a kidney, a prostate, skin, muscle, cartilage, viscera, and heart muscle) The method involves administering to the mammal a low dosage of a bisphosphonate sufficient to inhibit calcification of the soft tissue without inhibiting bone calcification. Such diseases include, but are not limited to atherosclerosis, arterioslerosis, arteriolosclerosis, hypertensive arteriolosclerosis, Monckeberg's arteriosclerosis, heart valve stenosis, uremia, diabetes, hyperparathyroidism, blood clot formation, cancer growth, cancer metastasis, hypertension, vitamin D toxicity, and arthritis. Preferred bisphosphonates and dosages include, but are not limited to the bisphosphonates and dosages described above. The mammal may be diagnosed as having or at risk for a pathology characterized by calcification of a soft tissue.

In still yet another embodiment, this invention provides methods of mitigating the calcification of an implanted prosthetic device in a mammal. These methods involve administering to the mammal a low dosage of a bisphosphonate sufficient to inhibit calcification of the prosthetic device or soft tissue surrounding said prosthetic device without inhibiting calcification of bone. Such prosthetic devices include, but are not limited to, a heart valve bioprosthesis, and a heart valve mechanical prosthesis. The prosthetic devices can also include, but are not limited to, a surgical implant comprising polyetherurethaneurea, a surgical implant comprising polyetherurethane; a surgical implant comprising silicon, a surgical repair material used for the repair of an aneurisms. Preferred bisphosphonates and dosages include, but are not limited to the bisphosphonates and dosages described above.

The methods of this invention can also be used to mitigate a symptom of atherosclerosis in a mammal. Such methods involve inhibiting osteoclastic bone resorption in said mammal. In preferred embodiment, the inhibiting is by administration of a bisphosphonate to the mammal in a concentration sufficient to inhibit bone resorption without inhibiting bone mineralization. Preferred mammals include, but are not limited to mammals diagnosed as having, or at risk for, atherosclerosis. Preferred bisphosphonates and dosages include, but are not limited to the bisphosphonates and dosages described above. The bisphosphonate is administered as a prophylactic or as a therapeutic treatment.

In another embodiment a symptom or progression of atherosclerosis in a mammal is inhibited by inhibiting the removal of mineral by macrophages at sites of calcification. In a preferred embodiment the inhibiting comprises administering a bisphosphonate to the mammal in a concentration sufficient to inhibit calcium removal by said macrophages. The bisphosphonate is preferably administered at a concentration that does not inhibit macrophages at locations other than sites of calcification. Preferred bisphosphonates and dosages include, but are not limited to the bisphosphonates and dosages described above. The method can be prophylactic and/or therapeutic.

Kits are also provided for the mitigation of a pathology associated with calcification of a soft tissue. Preferred kits include a container containing a bisphosphonate that inhibits calcification of a soft tissue at a dosage that does not substantially inhibit calcification of bone and instructional materials teaching the use of said bisphosphonate for treatment of a pathology associated with calcification of a soft tissue or calcification of a prosthetic device. Preferred bisphosphonates and dosages include, but are not limited to the bisphosphonates and dosages described above.

This invention also provides methods of stabilizing the size and/or the crystal structure of calcium or a calcium salt in an aqueous phase. These methods involve contacting the calcium or calcium salt with fetuin.

The stabilized calcium provides a method of delivering a calcification initiator to a preselected site. Such methods involve providing a fetuin-mineral complex attached to a targeting molecule (e.g., antibody, lectin, nucleic acid etc.) where the targeting molecule specifically binds to the preselected site; and contacting the fetuin mineral complex to the preselected site.

Also provided is a method of distributing mineral nuclei within a matrix. This method involves impregnating the matrix with a fetuin-mineral complex and denaturing the fetuin such that the mineral is released from the fetuin mineral complex.

The fetuin can also be used to stabilize the size or crystal structure of a mineral salt in an aqueous phase. This method involves contacting the mineral salt with a fetuin.

This invention also provides substantially isolated mineral salts (e.g. calcium phosphate) stabilized in a complex with fetuin.

Mammals subject to the methods described herein include, but are not limited to humans, non-human primates, canines, felines, equines, bovines, rodents, porcines, and lagomorphs. Thus, veterinary and human medical applications are contemplated.

In particularly preferred embodiments, the bisphosphonates used in the methods of this invention do not include bisphosphonates for which the dosage that inhibits bone mineralization is comparable to or equal to the dosage that inhibits bone resorption. The bisphosphonates used in the methods of this invention preferably do not include etidronate.

DEFINITIONS

Bisphosphonates, previously and erroneously called diphosphonates in the past, are compounds characterized by two C—P bonds. If the two bonds are located on the same carbon atom, the compounds are called geminal bisphosphonates and are analogs of pyrophosphate, containing an oxygen instead of a carbon atom (Formula I.).

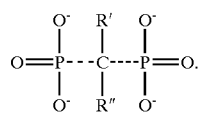

I

In the literature, these compounds are usually called bisphosphonates. This, however, is somewhat misleading, since non-geminal bisphophonates are also bisphosphonates. Thus, as used herein bisphosphonates include, both geminal and non-geminal bisphosphonates.

The P—C—P structure allows a great number of possible variations, either by changing the two lateral chains on the carbon or by esterifyng the phosphate groups. A number of bisphosphonates have been investigated in humans with respect to their effects of bone. A number are commercially available for the treatment of bone disease. These include, but are not limited to, alendronate (4-amino-1-hydroxybutylidene)bis-phosphonate), clodronate (dichloromethylene)-bis-phosphonate, EB-1053 (1-hydroxy-3-(1-pyrrolidinyl)-propylidene)bis-phosphonate, etidronate ((1-hydroxyethylylidene)-bisphosphonate), ibandronate (1-hydroxy-3-(methylpentylamino)propylidene)bis-phosphonate), incadronate ((([(cycloheptylamino)-methylene]bis-phosphonate), neridronate ((6-amino-1-hydroxyhexylidene) bis-phosphonate), olpadronate ((3-dimethylamino)-1-hydroxypropylidene)bis-phosphonate), palmidronate (3-amino-1-hydroxypropylidene)bis-phosphonate), risedronate (1-hydroxy-2-(3-pyridinyl)-ethylidene)bis-phosphonate), tiludronate ([[(4-chlorophenyl)thio)-methylene]bis-phosphonate), YH 529 ([1-hydroxy-2-imidazo-(1,2-a)pyridin-3-ylethylidene)bis-phosphonate), and zoledronate (1-hydroxy-2-(1H-imidazole-1-y) ethylidene)bis-phosphonate), and the like.

The term "bone resorption" refers to a process by which calcified bone tissue is removed from the bone, e.g. via the activity of osteoclasts. Elevated bone resorption may result in decreased bone mass and/or bone density (e.g. osteoporosis).

The terms "calcification" refers to the deposition of calcium in a tissue. The calcium can be in a number of forms, e.g. calcium phosphate, hydroxyapatite, carbonate apatite, amorphous calcium phosphate, etc.

The phrase "inhibition of calcification" or "inhibiting calcification" refers to a decrease in the rate and/or degree of calcification of a soft tissue. The inhibition may be complete or partial. Any measurable inhibition is viewed as an inhibition. A preferred inhibition is a statistically significant decrease in the rate and/or degree of calcification (e.g. at the 90% or better, preferably at the 95% or better, more preferably at the 98% or better, and most preferably at the 99% or better confidence level).

The phrase "without inhibiting bone mineralization" or "without inhibiting substantial bone mineralization" refers to the use of an agent in a dosage that it typically has no substantial effect on bone mineralization. In a preferred embodiment, it typically effects less than a 10%, more preferably less than a 1%, and most preferably less than a 0.1% decrease in the rate of bone mineralization. More preferably it has no statistically significant effect on bone mineralization (e.g. at the 90% or better, preferably at the 95% or better, more preferably at the 98% or better, and most preferably at the 99% or better confidence level). In a most preferred embodiment there is no detectable effect on bone mineralization.

The following abbreviations used are: MGP, matrix Gla protein; BGP, bone Gla protein (osteocalcin); fetuin, α2-HS Glycoprotein; and Gla, γ-Carboxyglutamic Acid.

BRIEF DESCRIPTION OF THE DRAWINGS

FIG. 9A:: ■, serum calcium, mM; FIG. 9B: ●, serum phosphate, mM; FIG. 9C: ▲, serum MGP, μg/ml.

FIG. 12A: serum from an etidronate treated rat; FIG. 12B: serum from a control rat.

FIG. 16A: ■, serum calcium, mM, in warfarin-treated rats; ☐, serum calcium, mM, in control rats; FIG. 16B: ●, serum phosphate, mM, in warfarin-treated rats; ○, serum phosphate, mM, in control rats; FIG. 16C: ▲, serum MGP, μg/ml, in warfarin-treated rats; Δ, serum MGP, μg/ml, in control rats.

DETAILED DESCRIPTION

I. Bisphosphonates and Ectopic Calcification

Figure 1:
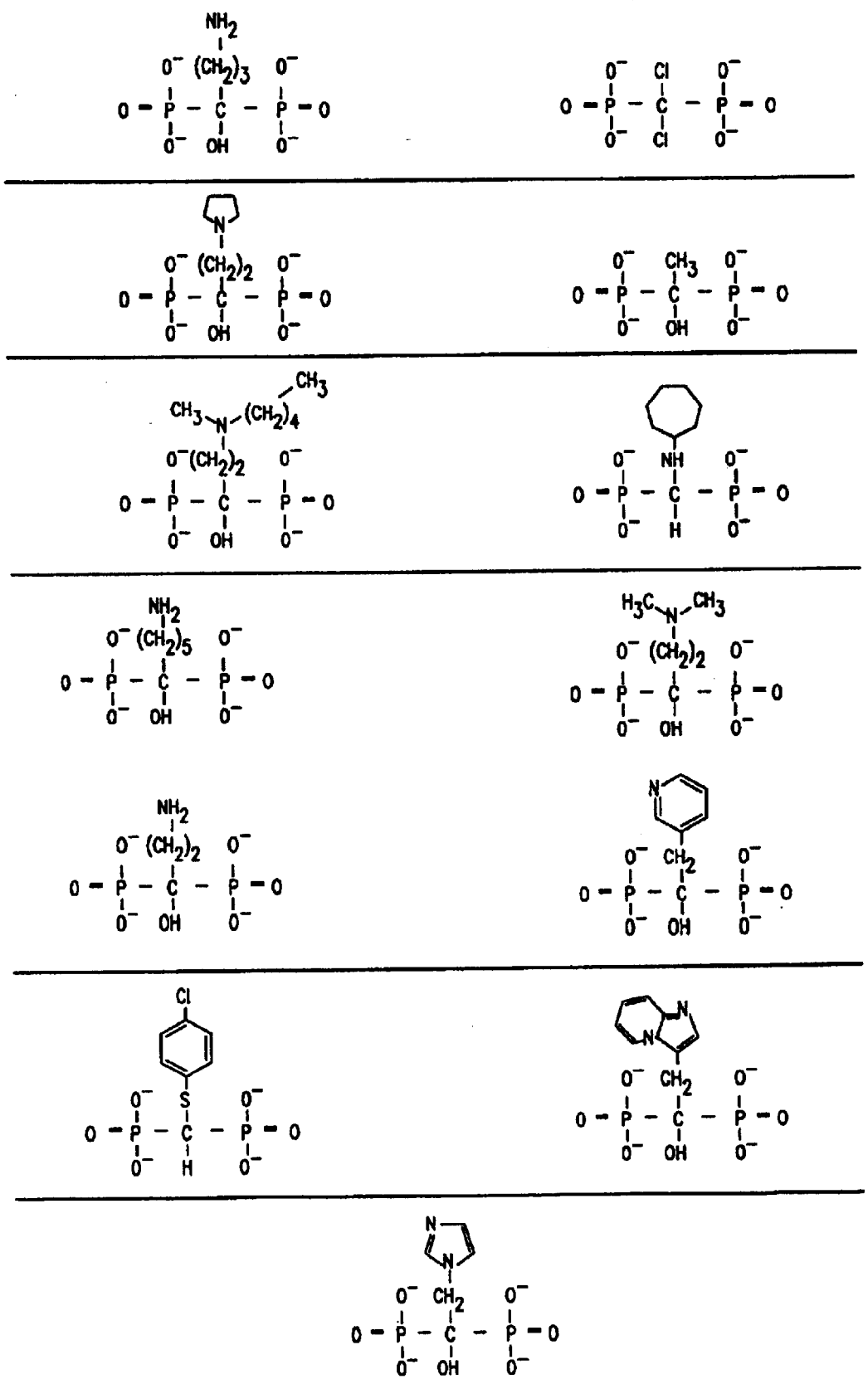
FIG. 1 illustrates a number of commercially available bisphosphonates.

This invention pertains to the discovery that, contrary to prevailing belief, bisphosphonates can be used to prevent calcification of soft tissues at concentrations sufficiently low that the bisphosphonates will not inhibit bone mineralization. Prior to this discovery it was generally believed that bisphosphonates inhibited calcification of soft tissues and bone mineralization through an identical, physiochemical mechanism (e.g. binding to nucleation sites and blocking crystal growth, etc.). Support for this belief was found, in part, in the observation that the first bisphosphonate to be investigated, etidronate, inhibits bone mineralization and soft tissue calcification at about the same high dosage (parenteral etidronate dose of about 5 mg P/kg/day), a dosage which is comparable to the etidronate dosage needed to inhibit bone resorption.

Because of the interest in the use of specific inhibitors of bone resorption to treat clinical disorders such as osteoporosis, a large number of bisphosphonates were subsequently synthesized and tested for their efficacy in inhibiting bone resorption at doses which do not inhibit bone mineralization. These investigations revealed that bisphosphonates differ dramatically in the concentration at which they inhibit bone resorption, with some bisphosphonates 1000 to 10,000 fold more effective on a dose basis than etidronate itself. In contrast, the newer bisphosphonates and etidronate were found to inhibit bone mineralization at comparably high doses (parenteral bisphosphonate doses of about 5 to about 20 mg P/kg/day). The immense difference in the very low effective dose of the newer bisphosphonates required to inhibit bone resorption, and the comparably high doses of the same bisphosphonates required to inhibit bone mineralization, has provided clinicians with a large therapeutic window of bisphosphonate doses that can be used to inhibit bone resorption without inhibiting bone mineralization.

It is our understanding that, prior to this invention, investigators believed that all bisphosphonates inhibit bone mineralization and soft tissue calcification by an identical physicochemical mechanism, and that both processes consequently were believed to require comparably high doses of the newer bisphosphonates (parenteral bisphosphonate doses of about 5 to about 20 mg P/kg/day). Because of this belief, no investigator examined the effect of low doses of the new bisphosphonates to see if it might be possible to inhibit soft tissue calcification without inhibiting bone mineralization.

It was a discovery of this invention that bisphosphonates appear to inhibit calcification of soft tissues by a mechanism fundamentally different from the mechanism by which they inhibit calcification of bone. It was a discovery of this invention that, as illustrated in Example 1, soft tissue calcification appears to be coupled to bone resorption. Thus, inhibition of bone resorption, by any mechanism, will result in an inhibition of soft tissue calcification. Without being bound to a particular theory, it is believed that the bone resorption process releases calcium phosphate complexes (e.g. a calcium phosphate/protein complex) that escape into the blood where they can act as nucleation centers to promote calcification at some site away from the bone (e.g. in an arterial wall, a heart valve, etc.).

In view of this, it was a discovery of this invention that a dosage of bisphosphonates (or other agent) sufficient to inhibit bone resorption will also inhibit soft tissue calcification. As indicated above, bisphosphonates all inhibit bone calcification at approximately the same dosage, while they differ significantly in the dosages required to inhibit bone resorption. Where the dosage level of the bisphosphonates required to inhibit bone resorption (and thereby inhibit soft tissue calcification) is lower than the dosage level required to inhibit bone calcification there will exist a therapeutic window; that is a dosage range wherein the bisphosphonate will inhibit soft tissue calcification without substantially inhibiting bone calcification.

Thus, in one embodiment, this invention provides methods of inhibiting calcification of soft tissue in a mammal. The methods involve administering to the animal a low dosage of a bisphosphonate, where the low dosage is sufficient to inhibit said calcification, but below the dosage of said bisphosphonate that inhibits normal bone mineralization. Such bisphosphonates can be used to treat a wide variety of disorders characterized by ectopic calcification as described below.

It was a discovery of this invention that inhibition of macrophages engaged in resorption of dystrophic calcifications can prevent and/or inhibit and/or induce regression in atherosclerosis. Without being bound by a particular theory, it is believed that calcification in the artery intima attracts macrophages which are able to actively resorb calcium deposited at this site. Macrophages in the intima then take up oxidized low density lipoproteins (LDLs) and become foamy cells which eventually die, releasing cholesterol in the intima and creating the cholesterol-rich atheroma. Calcification therefore creates a continuing cycle of macrophage recruitment and cholesterol deposition. This is a cycle which can be broken by specifically inhibiting macrophages at the calcification site.

Thus, in one embodiment, this invention provides methods of treating (prophylactically or therapeutically) atherosclerosis. The methods involve inhibiting macrophage-mediated calcium resorption. In a preferred embodiment, this is accomplished by administering an inhibitor that specifically inhibits macrophages involved in calcium uptake. In a particularly preferred embodiment, this is accomplished using a bisphosphonate at a relatively low dosage (e.g. a dosage comparable to that which inhibits bone resorption).

II. Indications

In view of the foregoing, the methods of this invention are particularly applicable in two contexts: 1) Where the organism (animal or human) is at risk for or has an ectopic calcification; and 2) Where the organism (animal or human) is at risk for, or has, atherosclerosis or arteriosclerosis.

A) Ectopic Calcification

In one embodiment the methods of this invention are used for the treatment (therapeutic or prophylactic) of an organism having, or at risk for, a calcification of a soft tissue. As used herein, a "soft tissue" refers to a tissue that is not calcified in a normal healthy mammal. Such ectopic calcifications arise in a wide variety of contexts including, but not limited to calcification of one or more heart valves (e.g. aortic valve), calcifications of lymph nodes, renal calcifications (e.g. nephrocalcinosis), calcifications of muscles and/or tendons, calcifications in the gall bladder, calcifications associated with uremia (e.g. associated with end-stage renal disease), certain cancer growths and/or metastases, calcification associated with blood clot formation, and the like.

The frequency of stenosis (associated with heart valve disease) as a cause of heart valve failure is very high, over 75%, and essentially all stenotic valves fail because of calcification. The number of subjects at risk for stenosis and heart valve replacement is fairly high, since it includes all subjects with some extent of heart valve calcification, which is about 30% of human subjects in their 60s. This high incidence of risk for stenoses suggests that the methods of this invention could be used prophylactically to decrease the risk of heart valve failure in all subjects for which there is evidence of progressive valve calcification.

Other ectopic calcifications are associated with trauma, repetitive stress, surgery, and/or biological implants. In particular, biological implants (e.g. prostheses) are vulnerable to undesired calcification. Bioprosthetic devices in which calcification is a serious problem include, but are not limited to porcine and bovine (i.e., exogenous) aortic, pulmonary, and mitral heart valve bioprotheses (e.g., Carpentier-Edwards Standard and Supraanular porcine bioprosthetic valves and Hancock porcine-heterograft bioprosthetic valves), heart valves and other surgical implants made from bovine, porcine, or human pericardium, and human valve homografts/allographs (human cadaver) and autografts (fabricated from the patient's own pulmonary valve, thigh connective tissue, or pericardium, etc.).

Other prosthetic devices in which calcification is a problem include, but are not limited to mechanical heart valves, particularly those made using polyetherurethaneurea and polyetherurethane; other surgical implants made from polyetherurethaneurea and polyetherurethane, silicone implants (including breast implants); and synthetic materials used for repair of aneurisms and other vascular problems.

B) Atherosclerosis and Arteriosclerosis

As indicated above, the methods of this invention are applicable to mammals (e.g. humans) having, or at risk for, atherosclerosis. Atherosclerosis refers to a progressive narrowing and hardening of the arteries over time. More generally, the methods of this invention are applicable to any arteriosclerosis that involves the deposition of calcium in the vascular intima. Thus, the methods of this invention are applicable to atheroscleroses including, but not limited to, atheroscleroses associated with Diabetes mellitus, hypertension, familial hypercholesterolemia, familial combined hyperlipidemia, familial dysbetalipoproteinemia, familial hypoalphalipoproteinemia, hypothyroidism, cholesterol ester storage disease, systemic lupus erythematosus, and homocysteinemia. In addition, the methods of this invention are applicable to non-atheromatous arterioscleroses involving calcium deposition including, but not limited to Diabetes mellitus, chronic renal insufficiency, chronic vitamin D intoxication, Monckeberg's arteriosclerosis, arteriosclerosis, hypertensive arteriosclerosis, pseudoxanthoma elasticum, idiopathic arterial calcification in infancy, aortic valvular calcification in the elderly, and Werner's syndrome.

Differential diagnoses for these conditions and/or for risk of these conditions are well known to medical personnel.

III. Agents for Use in this Invention

A) Preferred Agents

Preferred agents for use in the methods of this invention include, but are not limited to, bisphosphonates, more preferably bisphosphonates for which the dosage that inhibits bone resorption is lower than the dosage that inhibits bone calcification. In particularly preferred bisphosphonates the dosage that inhibits bone resorption is distinguishably lower than the dosage that inhibits bone calcification, more preferably there is a statistically significant difference between the dosage that inhibits bone resorption and the dosage that inhibits bone calcification (e.g. at 90% or better, preferably at 95% or better, more preferably at 98% or better, and most preferably at 99% or better confidence level). Most preferred bisphosphonates inhibit bone resorption at a dosage one or more orders of magnitude, preferably at a dosage two or more orders of magnitude, more preferably at a dosage 3 or more orders of magnitude and most preferably at a dosage four or more orders of magnitude lower than the dosage that inhibits bone calcification.

Particularly preferred bisphosphonates are commercially available and include, but are not limited to, alendronate (4-amino-1-hydroxybutylidene)bis-phosphonate), clodronate (dichloromethylene)-bis-phosphonate, EB-1053 (1-hydroxy-3-(1-pyrrolidinyl)-propylidene)bis-phosphonate, ibandronate (1-hydroxy-3-(methylpentylamino)propylidene)bis-phosphonate), incadronate (([(cycloheptylamino)-methylene]bis-phosphonate), neridronate ((6-amino-1-hydroxyhexylidene)bis-phosphonate), olpadronate ((3-dimethylamino)-1-hydroxypropylidene)bis-phosphonate), palmidronate (3-amino-1-hydroxypropylidene)bis-phosphonate), risedronate (1-hydroxy-2-(3-pyridinyl)-ethylidene)bis-phosphonate), tiludronate ([[(4-chlorophenyl)thio)-methylene]bis-phosphonate), YH 529 ([1-hydroxy-2-imidazo-(1,2-a)pyridin-3-ylethylidene)bis-phosphonate), and zoledronate (1-hydroxy-2-(1H-imidazole-1-y) ethylidene)bis-phosphonate), and the like.

Other bisphosphonates are also known to those of skill in the art. Thus, for example, U.S. Pat. No. 5,317,015 describing the synthesis and use of azacyclic bisphosphonates, and U.S. Pat. No. 5,103,036 describing the preparation of 3-alkenylidene-1,1-bisphosphonates. Methods of synthesizing numerous other bisphosphonates are well known to those of skill in the art (see, e.g., U.S. Pat. Nos. 5,622,973, 5,616,571, 5,616,560, 5,403,829, 5,338,731, 5,196,409, and the like).

Methods of assaying new bisphosphonates for use in the methods of this invention are straightforward. In one embodiment, the bisphosphonates is simply assayed for a dosage that inhibits bone resorption and for the dosage at which it inhibits bone calcification as illustrated in the examples, and as taught in the literature (see, e.g., Muhlbauer et al. (1991) *J. Bone and Mineral Res.* 6: 1003–1010; Antic et al. (1996) *Calcif. Tissue Int.* 58: 443–448). If the dosage at which the bisphosphonate in question inhibits bone resorption is lower than the dosage at which the bisphosphonate inhibits bone calcification, and toxicity is acceptable, the bisphosphonates is a good candidate for use in the methods of this invention.

B) Bisphosphonate Dosages

It was a discovery of this invention that, in contrast to the prevailing belief, bisphosphonates can be administered at low dosages rather than at high dosages to inhibit ectopic calcification and/or to treat atherosclerosis and related conditions. In particular, suitable low dosages are dosages at which the bisphosphonates inhibit bone resorption without inhibiting bone mineralization. Thus preferred dosages range from a dosage sufficient to inhibit bone resorption and/or ectopic calcification (a minimum therapeutically effective dose) up to a dosage comparable to that used to inhibit bone calcification. Such a dosage range is often at least 10-fold, preferably at least 100-fold, more preferably at least 1000-fold, and most preferably at least 10000-fold less than the dosage that inhibits bone calcification. Dosages that inhibit bone resorption and that inhibit bone calcification will vary with the formulation and mode of administration and can be determined from the product literature for commercially available bisphosphonates. Suitable dosages for other bisphosphonates can be determined empirically.

In the case of alendronate in one preferred embodiment, the aldendronate is administered to humans at an oral dosage ranging from about 5 mg to about 40 mg per day. In the case of ibandronate, in one preferred embodiment, the ibandronate is preferably administered at an intravenous dosage of 1 mg/day. For zoledronate, incadronate, risedronate, EB-1053, neridronate, olpadronate, pamidronate, YH 529, tiludronate, or clodronate a preferred dosage ranges from the minimum dose that produces a detectable inhibition of bone resorption up to 0.5 mg P/kg/day.

C) Formulation and Administration of Bisphosphonates

Acute, sub-acute, and chronic administration of bisphosphonates has, in general, revealed little toxicity. This is generally explained by their rapid incorporation into calcified tissue and hence their short presence in the circulation. Accordingly, a wide variety of formulations and routes of administration are available.

The compounds of the present invention can be administered to a mammalian host in a variety of forms adapted to the chosen route of administration, i.e., orally, or parentally. Parenteral administration in this respect includes, but is not limited to, administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, when an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 0.1% to about 6% of the weight of the unit. The amount of active compound in such therapeutically useful compositions is such that a suitable dosage, as described above, will be obtained. Preferred compositions or preparations according to the present invention are prepared so that an oral dosage unit form contains between about 0.01 mg and about 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as a preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as an ester, a free base or a pharmacologically acceptable salt can be prepared in water or other aqueous solution (e.g. water suitably mixed with a surfactant such as hydroxypropylcellulose). Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions can be obtained by the use of agents delaying absorption, for example, aluminum monostearate and gelatin.

Sterile injectable solutions are prepared by incorporating the active compound in the required amount in the appropriate solvent with various of the other ingredients enumerated above, as required, typically followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice. Thus, for example, to enhance bioavailability of oral formulations, the therapeutic compound may be formulated with a chelator (e.g. EDTA).

The physician will determine the dosage of the present therapeutic agents which will be most suitable for prophylaxis or treatment in accordance with the advantageous low dosages as taught herein and it will vary with the form of administration and the particular compound chosen, and also, it will vary with the particular patient under treatment. He will generally wish to initiate treatment with small dosages and increase the dosage by small increments until the optimum effect under the circumstances is reached.

The compounds of the invention may also be employed in combination with one or more other active agents. Thus, for example, the compounds described herein may be administered with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin, etc.

IV. Other Inhibitors of Calcification

The methods described herein are not limited to bisphosphonates. As indicated above, it was a discovery of this invention that essentially any agent that inhibits osteoclastic bone resorption at a dosage that does not also substantially inhibit bone calcification will also inhibit ectopic calcification. Thus, other agents (e.g. non-bisphosphonates) that inhibit osteoclastic bone resorption are good candidates for use in the methods of this invention. Such agents can be identified by routine screening e.g. as illustrated in the Examples.

Similarly, it was a discovery of this invention that agents that inhibit macrophage-mediated removal of mineral will also inhibit the development and/or progression of atherosclerosis. Thus agents that inhibit macrophage activity (e.g. genisteine), more preferably agents that specifically inhibit macrophages involved in the uptake of calcium (e.g. by rapidly associating with calcium so that they are internalized by this subset of macrophages) are good candidates for the methods of this invention.

V. Fetuin Complexes

It was also a discovery of this invention that the serum protein fetuin forms a stable complex with a calcium phosphate mineral phase and that this complex can under some circumstances be detected in blood. Without being bound to a particular theory it is believed that the fetuin/calcium phosphate complex is a form in which calcium removed during bone resorption is solubilized in plasma and migrates to new sites where it can act as a nucleation site for calcium deposition and thereby contribute to ectopic calcification and to atherosclerotic plaque formation.

The fetuin-mineral complex can be synthesized using pure fetuin, calcium, and phosphate (see, Example 2). In brief, the procedure allows the synthesis of small mineral particles of uniform size which can be seen by transmission electron microscopy. Because the size of the fetuin mineral complex is very small, a solution containing very high concentrations of the fetuin mineral complex is quite clear and the complex does not settle. The particles are stable, with no apparent changes over 7 days of observation. We believe that the mineral phase trapped by this complex is the first phase formed in calcification of bone and teeth. Prior to this invention, there was no method for preparing this phase in a stable form, and no method for preparing a solution containing this phase at uniform concentration.

The formation of such complexes is readily demonstrated. When concentrated solutions of calcium and phosphate are mixed to create a final mixture containing e.g., 40 mM Calcium and 40 mM phosphate, a dense white precipitate forms within a fraction of a second which slowly sinks to the bottom the test tube. If fetuin is added prior to mixing, the dense white precipitate fails to form and the solution remains quite clear for days. If one looks at the solution by electron microscopy, numerous small mineral nuclei are present which have remarkably uniform size and shape. The nuclei, which are coated with fetuin, account for over 95% of the calcium and phosphate in the mixture. This experiment illustrates the power of the fetuin molecule to direct the course of a mineralization process.

This discovery can be exploited in a number of contexts. For example, this discovery provides a general method for the preparation of any unstable mineral phase by using a protein which binds to this mineral phase selectively in order to trap the unstable phase and prevent its transformation to more stable phases. A fetuin mineral complex can be used to distribute mineral nuclei within a suitable matrix so that subsequent inactivation of fetuin (e.g. by heat, acid, addition of a chaotropic agent, etc.) would cause rapid and uniform calcification of this matrix. This method could be used, for example, to prepare a calcified structure for use in a bio prosthetic device or other device.

Because the fetuin mineral complex is stable in blood, it can be used as a transport vehicle to deliver calcification initiators to desired sites in the body. For example, the fetuin in the complex could be modified so that it binds to a site where calcification is desired (e.g. teeth, bone, etc.) and so that fetuin can be inactivated at this site to allow mineralization to proceed. Typically such a modification would involve coupling a targeting molecule (e.g., an antibody, antibody fragment, single chain antibody, a lectin, a lipid, a carbohydrate, a sugar, etc.) to the fetuin-mineral complex. The targeting molecule is selected to specifically bind to the target (e.g. cell receptor, ligand, etc.) whereby the mineral complex is delivered to the desired target.

It is noted that fetuin is a glycoprotein and methods of attaching molecules to glycoproteins (directly or through a linker) are well known to those of skill in the art. The attachment is preferably by way of a linker. A "linker" as used herein, is a molecule that is used to join the targeting molecule to the fetuin-mineral complex. The linker is capable of forming covalent bonds to both the fetuin and to the targeting molecule. Suitable linkers are well known to those of skill in the art and include, but are not limited to, straight or branched-chain carbon linkers, heterocyclic carbon linkers, or peptide connectors. The linkers may be joined to the constituent amino acids through their side groups (e.g., through a disulfide linkage to cysteine) or joined to the alpha carbon amino and carboxyl groups of the terminal amino acids.

Many procedures and linkers molecules for attachment of various polypeptides are known (see, e.g., European Patent Application No. 188,256; U.S. Pat. Nos. 4,545,985 and 4,894,443, 4,671,958, 4,659,839, 4,414,148, 4,699,784; 4,680,338; 4,569,789; and 4,589,071; and Borlinghaus et al. (1987) *Cancer Res.* 47: 4071–4075; Waldmann (1991) *Science*, 252: 1657).

The fetuin mineral complex can also be used as a reagent to develop fetuin-mineral specific assays which, in turn, can be used to determine the levels of a fetuin mineral complex in human blood. This would provide a method to measure bone metabolic processes relevant to the management of patients with bone disease.

Without being bound to a particular theory, it is believed that a surface of the fetuin molecule binds strongly and specifically to the target mineral phase. This binding exposes surfaces on fetuin which have a high affinity for other bound fetuin molecules, forming strong lateral associations that arrest crystal growth. The oligosaccharide moieties in fetuin, which account for about half of its mass, project away from mineral and form a hydrated shell which keeps the fetuin mineral complex from aggregating or settling from solution. This model suggests that engineered modifications in the mineral interaction surface of fetuin could direct the protein to any desired mineral phase, thereby enabling the protein to control the synthesis of this mineral phase.

VI. Fetuin Complexes as Prognostic Markers, Diagnostic Markers, and Surrogate Markers In still another embodiment, this invention pertains to the discovery that the fetuin-mineral complex in blood (e.g. serum), is an effective prognostic and diagnostic marker for calcification of arteries and other soft tissues, atherosclerosis, and osteoporosis. In general, increased levels (e.g. increased serum concentration) of the fetuin-mineral complex in a mammal indicates that the mammal is at increased risk for or has calcification of arteries and/or other soft tissues, and/or atherosclerosis, and/or osteoporosis.

When used as a prognostic or diagnostic marker, the fetuin-mineral complex level (serum concentration) is preferably used in the context of a differential diagnosis or prognosis for presence or risk of atherosclerosis, soft tissue calcification and/or osteoporosis. When used in the context of other known diagnostic markers and/or risk factors for each of these conditions, it is possible to determine for which condition, or combination of conditions, the fetuin mineral complex is an indicator.

The fetuin-mineral complex also provides a convenient marker for the response of an organism for treatment. In this context, a mammal (e.g. a human or non-human mammal) having one or more of the above-identified conditions is treated for those condition(s). The fetuin-mineral complex level in the mammal (e.g. in a blood sample from the mammal) is monitored before and/or during and/or after the treatment. A decrease in the level of the fetuin mineral complex (preferably a statistically significant decrease) indicates that the mammal is responding to the treatment.

The decrease in fetuin-mineral complex, is typically evaluated with respect to a control. Suitable controls include, but are not limited to blood from the same mammal obtained before the treatment, blood from the same mammal obtained at an earlier time point in the course of the treatment, the level of a fetuin-mineral complex found in a normal healthy mammal of the same species, a predetermined concentration of a fetuin-mineral complex, and the like.

Methods of detecting and/or isolating the fetuin mineral complex are detailed in Example 3. Using the methods described therein, one of skill can readily optimize protocols to facilitate fetuin-mineral complex isolation from essentially any mammalian species including humans. Thus, for example, in one particularly preferred embodiment, when isolating the fetuin mineral complex from humans the fetuin-mineral complex is sedimented by using high centrifugational speeds and relatively long centrifugation times. The following is an example of a procedure that can be used to sediment the complex for quantitative determination of its level in serum or plasma:

175 µl of human serum or heparin plasma is aliquoted into a Beckman airfuge tube (5 by 20 mm ultraclear polyallomer tube). The tube is placed into the A-110 rotor of the Beckman airfuge (air-driven ultracentrifuge, Beckman Coulter, Inc.) and the air pressure is adjusted to achieve a final centrifugational speed of 110,000 rpm. This is typically accomplished with an air pressure of about 30 psi. It is useful to mark the top of the tube on the side away from the axis of rotation, since this is the side that will have the pellet containing the fetuin mineral complex. The tube is centrifuged for a total of 1 h at 110,000 rpm. The supernatant is then removed using a flat gel loading pipet tip (USA Scientific) on a pipetman, and transfer to an epitube. In this procedure it is important that the pipet tip be placed away from the side of the tube that contains the pellet (see above). THe airfuge tube is inverted and gently tapped on a kimwipe to remove any remaining supernatant. The airfuge tube is checked to see if a fetuin-mineral complex can be detected. If there is a substantial amount of the fetuin-mineral complex it can be seen as a small glassy pellet on the bottom side of the tube furthest from the axis of rotation. Then 35 µl of 0.15M HCl is added to the tube and incubated 1 h at room temperature in order to dissolve the fetuin-mineral complex. The level of calcium, and/or phosphate, and/or MGP, and/or fetuin can be determined in the dissolved pellet. The amount of fetuin-mineral complex can be calculated from the amount of any of these constituents that are found in the pellet. The level of calcium, and/or phosphate, and/or MGP, and/or fetuin in the supernatant and in the original sample is determined. If a substantial amount of the complex is present, there will be a significantly lower level of these components in the supernatant than in the original solution, and the amount of the complex can be determined from this difference.

This method is most often useful for MGP, since MGP associated with the pellet typically accounts for a significant amount of the total MGP in the original serum sample.

Detection of low levels of the fetuin mineral complex may be hampered by the presence of small amounts of serum that wet the tube even after the supernatant is removed, since the supernatant will contain calcium, phosphate, MGP, and fetuin. To control for this problem, set up an identical tube of the sample but skip step the centrifugation step. The amount of calcium, phosphate, MGP, and/or fetuin in this acid extract can then be subtracted from the amount present in the tube that was centrifuged. An alternative approach is to gently add 100 µl of 0.15M NaCl to the tube, taking care to avoid disturbing the pellet. The NaCl wash is immediately removed and Add 35 µl of 0.15M HCl is added to the tube and incubated 1 h at room temperature in order to dissolve the fetuin-mineral complex as described above.

The complex can be detected directly. Alternatively, any one or more of the constituents of the complex can be detected and used to provide a measure of the amount of the complex present. Such consitutents include, but are not limited to the fetuin, matrix Gla protein, secreted phosphoprotein 24, platelet factor 4, calcium, phosphate, mineral phase, and the like.

VII. Kits

In still another embodiment, this invention provides kits for inhibiting ectopic calcification and/or atherosclerosis. The kits include one or more bisphosphonates preferably formulated as pharmaceuticals (e.g. in a pharmacologically acceptable excipient). In addition, the kits preferably include instructional materials containing directions (i.e., protocols) describing the indications for the use of the compositions and recommending dosages as described herein.

In another embodiment, this invention provides kits for the presence or likelihood (risk for) atherosclerosis, and/or calcification of an artery or other soft tissue, and/or osteoporosis. The kits typically comprise one or more reagents used in the isolation and/or detection of a fetuin mineral complex (e.g. as described in Example 3). The kit, optionally, also includes instructional materials providing protocols for the isolation and/or detection (e.g. quantification) of a fetuin-mineral complex.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Bisphosphonates Prevent Artery Calcification at Doses that Inhibit Bone Resorption, But Not Bone Mineralization The present experiments were carried out to test the hypothesis that bisphosphonates inhibit artery calcification by virtue of their ability to inhibit bone resorption. The hypothesis that bone resorption is linked with artery calcification originated in experiments carried out to understand the factors which enhance artery calcification in rats treated with high doses of warfarin, a vitamin K antagonist which inhibits the γ-carboxylation of matrix Gla protein and thereby causes arteries and other soft tissues to calcify. In the course of these studies we observed that warfarin treatment induces artery calcification to the greatest extent in young, rapidly growing rats, and that adult rats are completely resistant to warfarin induced artery calcification. The susceptibility of young rats to warfarin induced artery calcification is related to growth and not age per se, since warfarin treatment fails to induce artery calcification in young rats fed a restricted diet with a caloric content adequate to maintain body weight without permitting bone growth or weight gain. These experiments showed that growth processes promote artery calcification, and were consistent with the hypothesis that bone metabolism could in fact be the critical determinant for susceptibility to warfarin-induced artery calcification. In a second series of experiments we observed that high doses of vitamin D accentuate artery calcification in rats treated with warfarin. Since vitamin D is known to potently stimulate bone resorption, one explanation for the increased susceptibility of vitamin D treated rats to warfarin-induced artery calcification could be a link between bone resorption and artery calcification.

Background for these Experiments

Bisphosphonates have been previously shown to inhibit bone resorption, normal bone mineralization, and experimentally induced artery calcification (see Fleisch (1998) *Endocrine Rev.* 19: 80–100 for a recent review). The first bisphosphonate to be studied thoroughly, etidronate, inhibits bone resorption, normal bone mineralization, and artery calcification at comparably high doses. Because of the interest in the use of specific inhibitors of bone resorption to treat clinical disorders such as osteoporosis, a large number of bisphosphonates have been synthesized and tested for their efficacy in inhibiting bone resorption at doses which do not inhibit bone mineralization. Among the bisphosphonates currently in clinical use, two of the most potent bone resorption inhibitors are alendronate and ibandronate, which are 1000 and 10000 fold more effective resorption inhibitors than etidronate, respectively. Since all bisphosphonates inhibit bone mineralization at comparably high doses (Fleisch (1998) *Endocrine Rev.* 19: 80–100; Fleisch (1997) *Ann. Med.* 29: 55–62), the discovery that alendronate and ibandronate are far more potent bone resorption inhibitors allows the inhibition of bone resorption in patients using doses of these drugs which do not affect normal mineralization processes.

The mechanisms by which bisphosphonates inhibit mineralization processes in vivo are poorly understood. Bisphosphonates bind strongly to hydroxyapatite, the mineral phase of bone, and are cleared rapidly from blood by virtue of their ability to bind to bone mineral (Ibid.). In vitro, all bisphosphonates potently inhibit formation of calcium phosphate mineral phases from supersaturated solutions of calcium and phosphate, and the concentrations of different bisphosphonates that are required to inhibit calcification in vitro are comparable (Ibid.). In vivo, all bisphosphonates potently inhibit normal mineralization of bone and other structures, and the concentrations of different bisphosphonates that are required to inhibit normal mineralization are comparable and quite high (parenteral bisphosphonate doses of 5 to 20 mg P/kg/day) (Fleisch (1998) *Endocrine Rev.* 19: 80–100). Because all bisphosphonates inhibit normal bone mineralization in vivo at comparably high doses, and all bisphosphonates inhibit formation of hydroxyapatite from supersaturated solutions in vitro at comparable concentrations, it has been suggested that both actions reflect the same basic ability of these compounds to bind to hydroxyapatite crystals and inhibit crystal growth by a physicochemical mechanism.

Investigators have held that the inhibition of experimentally induced artery calcification by bisphosphonates is also related to the ability of these compounds to bind to hydroxyapatite crystals and inhibit crystal growth in vitro, and to the ability of these compounds to inhibit normal bone mineralization in vivo, and have indeed stated that it would be impossible to use such drugs to inhibit calcification of arteries and other soft tissues without also inhibiting normal mineralization process (Fleisch (1998) *Endocrine Rev.* 19: 80–100; Fleisch (1997) *Ann. Med.* 29: 55–62). In the present study we have for the first time demonstrated that bisphosphonates inhibit artery calcification by a different mechanism than the mechanism by which they inhibit normal bone mineralization, namely by inhibiting bone resorption. It is therefore possible to use the newer class of more potent bone resorption inhibitors, such as alendronate and ibandronate, to inhibit calcification of arteries and heart valves without affecting normal mineralization processes.

Experimental Procedures

Materials

Vitamin $K_1$ (phylloquinone), vitamin $D_3$ (cholecalciferol), and warfarin were purchased from Sigma (St. Louis, Mo.). Etidronate (Didronel, Proctor and Gamble Pharmaceuticals) and alendronate (Fosamax, Merck and Co., Inc.) were purchased from University City Pharmacy, San Diego, Calif., and Ibandronate (Bondronat, Boehringer Mannheim) was purchased from Idis World Medicines, Surrey, United Kingdom. Stock solutions of alendronate and etidronate were prepared in 0.15 M NaCl, titrated to pH 7.4 with NaOH, and stored at 4° C. Ibandronate was diluted with 0.15M NaCl and stored at 4° C. All bisphosphonate doses are stated in mg P so that the molar effectiveness of the drugs can be compared directly, a method which has been employed in earlier studies (Muhlbauer et al. (1991) *J. Bone and Mineral Res.* 6: 1003–1010; Antic et al. (1996) *Calcif. Tissue Int.* 58: 443–448). The following values were used to convert from actual measured weight of bisphosphonate to mg P for each drug used: Alendronate $(Na)(H_2O)_3$=62 mg P per 325 mg drug, etidronate $(Na)_2$=62 mg P per 250 mg drug, and ibandronate $(Na)(H_2O)$=62 mg P per 357 mg drug. Stock solutions of vitamin $K_1$ were prepared at 10 mg per ml and stored in sterile, foil wrapped containers at 4° C. Stock solutions of sodium warfarin were prepared at 50 mg per ml in 0.15M NaCl and stored at 4° C. Finally, stock solutions of vitamin D were prepared fresh for each 3 day subcutaneous injection cycle at a concentration of 1.65 mg/ml in 7% emulphor (alkamuls EL-620, Rhone-Poulenc) and then wrapped in foil and stored at 4° C. Simonsen albino rats (Sprague-Dawley derived) were purchased from Simonsen labs (Gilroy, Calif.).

Methods

For measurement of mineral accumulation in arteries, each tissue was removed within 30 minutes of death and immediately frozen. Tissues were subsequently washed extensively with buffer and extracted with 1 ml of 10% formic acid for 24 h at room temperature, as described. Calcium levels in serum were determined colorimetrically using cresolphthalein complexone (Sigma) and phosphate levels in serum and in acid tissue extracts were determined calorimetrically as described (Zhu et al. (1994) *Cardiology*, 85: 370–377). Tissue sectioning and staining were carried out by Biomedical Testing Services, Inc., (San Diego, Calif.).

Male Sprague Dawley rats were fed ad libitum with rodent diet 5001 (Purina Mills Inc., St. Louis, Mo.), a diet that is 0.67% phosphorus and 0.95% calcium by weight. This diet contains 500 µg per kg of phylloquinone and has no added menadione. In all experiments, animals were killed by exsanguination while under metofane anesthetic, and selected tissues were removed immediately and fixed in 10% buffered formalin or frozen at −20° C. for later studies. All animal experiments were approved by the UCSD animal subjects committee.

The effect of bisphosphonates on artery calcification was first examined in rats in which artery calcification was induced by treatment with warfarin plus high doses of vitamin D. In brief, 49 day old male rats received subcutaneous doses of 300,000 IU vitamin D per kg at t=0, 24, and 48 h. Starting at t=0, each animal also received injections of warfarin every 12 h and of vitamin K every 24 h. All animals were killed by exsanguination at 96 h. In the initial experiment (FIG. 2), 6 rats were treated with alendronate at a dose of 0.25 mg P/kg/day starting four days prior to the first vitamin D injection, and 6 rats received no alendronate. All animals were killed by exsanguination at 96 h after the first vitamin D dose. In the dose dependence experiments, animals were given identical treatment with warfarin, vitamin K, and vitamin D together with the desired dose and type of bisphosphonate (4 rats per dose) starting 4 days prior to the first vitamin D injection; all animals in the dose dependence experiments (FIGS. 3 and 4, and Table III) were killed by exsanguination at 84 h after the first vitamin D dose. In the experiments on the effect of the timing of alendronate administration on artery calcification (FIGS. 5 and 6), animals were again given identical treatment with warfarin, vitamin K, and vitamin D together with the following treatment with alendronate at a dose of 0.25 mg P/kg/day: Group A received no alendronate (11 rats); Group B received alendronate continuously for 8 days, starting 4 days prior to the first vitamin D injection (6 rats); Group C received alendronate for 6 days, starting 4 days prior to the first vitamin D treatment and ending with the final dose on the second day of vitamin D treatment (at t=24 h) (6 rats); and Group D received alendronate only for the last two days of the 8 day experiment (at t=48 and 72 h) (9 rats). All animals in the experiments on the timing of alendronate dose were killed by exsanguination 96 h after the first vitamin D injection. In the final experiment, 49 day old male rats received subcutaneous doses of 300,000 IU vitamin D per kg at t=0, 24, and 48 h but did not receive warfarin; 4 rats received alendronate at a daily dose of 0.25 mg P/kg/day starting 4 days prior to the first vitamin D injection, 4 rats received ibandronate at dose of 0.01 mg P/kg/day starting 4 days prior to the first vitamin D injection, and 4 rats did not receive bisphosphonate. All animals were killed by exsanguination 96 h after the first vitamin D injection.

The effect of bisphosphonates on artery calcification was also examined in rats treated with warfarin alone using procedures which have been described elsewhere (Price et al. (1998) *Arterioscler. Thromb. Vasc. Biol.* 18: 1400–1407). This procedure induces artery calcification within 2 weeks without the presence of hypercalcemia. In the first series of experiments, 42 day old male rats were treated with warfarin for two weeks and with bisphosphonates beginning 4 days prior to the first warfarin dose according to the following doses: 8 rats received no bisphosphonate; 4 rats received alendronate at 0.25 mg P/kg/day; and 4 rats received ibandronate at 0.01 mg P/kg/day. In the second series of experiments, 42 day old male rats were treated with warfarin for 4 weeks and with bisphosphonates beginning 4 days prior to the first warfarin dose according to the following doses: 8 rats received no bisphosphonate; 3 rats received alendronate at 0.25 mg P/kg/day; 3 rats received alendronate at 0.025 mg P/kg/day; and 4 rats received etidronate at 6.25 mg P/kg/day.

Results

Effect of Bisphosphonates on Artery Calcification in Rats Treated with High Doses of Vitamin D To evaluate the possible relationship between bone resorption and artery calcification we initially examined the effect of alendronate, a bisphosphonate which potently inhibits bone resorption, on artery calcification in rats treated with high doses of vitamin D. In most of these experiments we also treated the animals with the vitamin K antagonist warfarin in order to suppress the γ-carboxylation of matrix Gla protein, a vitamin K-dependent inhibitor of artery calcification, and thereby enhance the extent of artery calcification compared to that seen in animals treated with high doses of vitamin D alone. In previous studies we have shown that treatment with vitamin D plus warfarin causes rapid and massive calcification of the elastic lamellae of the aorta and other arteries, and that significant calcification is apparent 72 h after the first vitamin D injection.

Figure 2:
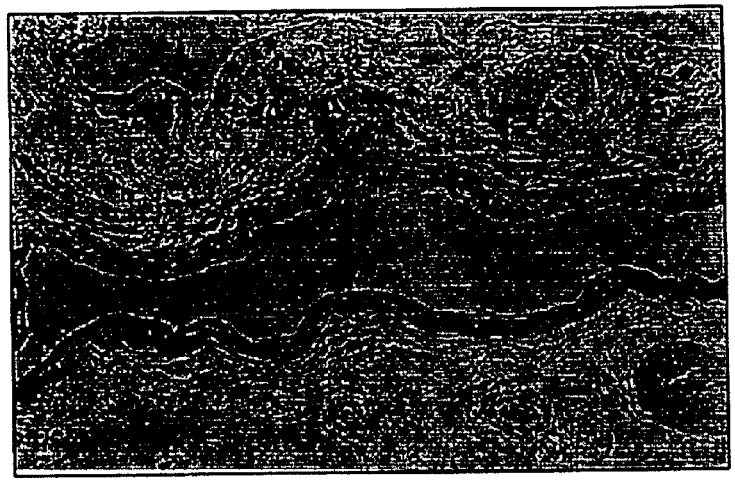
FIG. 2 illustrates the effect of alendronate treatment on von Kossa staining for aorta calcification in rats treated with vitamin D plus warfarin. Twelve 7 week old male Sprague Dawley rats were given subcutaneous injections of 300,000 IU vitamin D/kg body weight at t=0, 24, and 48 h. Beginning with the first vitamin D injection, rats were also treated with subcutaneous injections of vitamin K every 24 h and warfarin every 12 h. Six animals were injected subcutaneously with alendronate at a dose of 0.25 mg P/kg/day beginning 4 days prior to the first vitamin D injection, and the remaining 6 animals received no alendronate. All animals were killed 96 h after the first vitamin D injection and the abdominal aorta segment between the renal branch and the femoral bifurcation was immediately removed from each animal and fixed in 10% buffered formalin. Longitudinal sections of each aorta were stained for mineral by von Kossa. The panels illustrate typical sections from the 6 rats treated with alendronate and from the 6 animals which did not receive alendronate.
Figure 2:
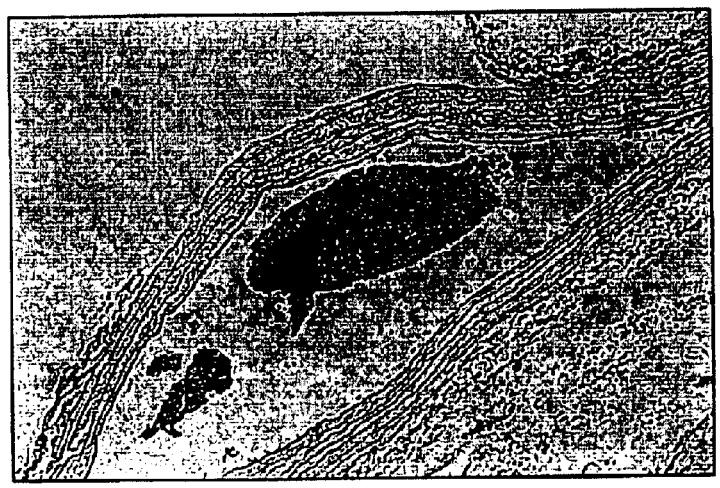

In the initial experiments, we injected 49 day old male rats subcutaneously with alendronate at a dose of 0.25 mg P/kg/day. This dose is comparable to the 0.3 mg P/kg/day subcutaneous dose of alendronate which that has been demonstrated to completely inhibit the increase in bone resorption induced by a calcium deficient diet in 58 day old male rats (Antic et al. (1996) *Calcif. Tissue Int.* 58: 443–448). The daily alendronate treatment was initiated four days prior to the first vitamin D injection because previous studies have shown that it takes about 4 days of alendronate treatment to maximally inhibit bone resorption (FIG. 3 in Antic et al. (1996) *Calcif. Tissue Int.* 58: 443–448). When the animals were examined 96 h after the first vitamin D injection there was no detectable von Kossa staining for mineral in the abdominal aorta of any of the 6 animals treated with vitamin D plus alendronate, while there was massive von Kossa staining for mineral in the elastic lamella of the abdominal aorta media in all 6 of the animals treated with vitamin D plus vehicle (FIG. 2). Alendronate treatment also completely eliminated von Kossa staining in the elastic lamella of aortic heart valves and in the elastic lamella of the media in all other arteries examined, which included the renal, pulmonary, and carotid arteries (Figures not shown). In addition, alendronate treatment eliminated the von Kossa staining of the kidney, a calcification which we have observed in rats treated with high doses of vitamin D plus warfarin that is not associated with arteries. Quantitative analysis of the extent of mineral accumulation revealed that the acid demineralization extracts of the thoracic aorta and carotid arteries of the vitamin D treated animals had calcium and phosphate levels which were at least 40 times higher than found in the corresponding tissues from control rats, while the acid demineralization extracts of the thoracic aorta and carotid artery of animals treated with vitamin D plus alendronate had calcium and phosphate levels which were not significantly elevated compared to levels in control tissues (data not shown).

Previous studies have shown that treatment with high doses of vitamin D alone is highly toxic to animals (Takeo et al. (1989) *Atherosclerosis*, 77: 175–181; Takeo et al. (1991) *Molec. Cell. Biochem.* 107: 169–183), and that concurrent treatment with warfarin augments the lethal nature of vitamin D administration. To examine the relationship between alendronate treatment and mortality, animals were treated with vitamin D plus warfarin and given either alendronate at a dose of 0.25 mg P/kg/day or vehicle starting 4 days prior to the first vitamin D injection. All 4 of the animals treated with vehicle plus vitamin D were dead within 6 days of the first vitamin D administration, while all 4 of the animals treated with alendronate plus vitamin D were alive and healthy at day 12, the end of the period of observation. We conclude that mortality in animals treated with high doses of vitamin D is prevented by treatment with alendronate, and that the probable cause of death in animals treated with high doses of vitamin D is the calcification of some as yet unidentified structure which is critical for life.

Figure 3:
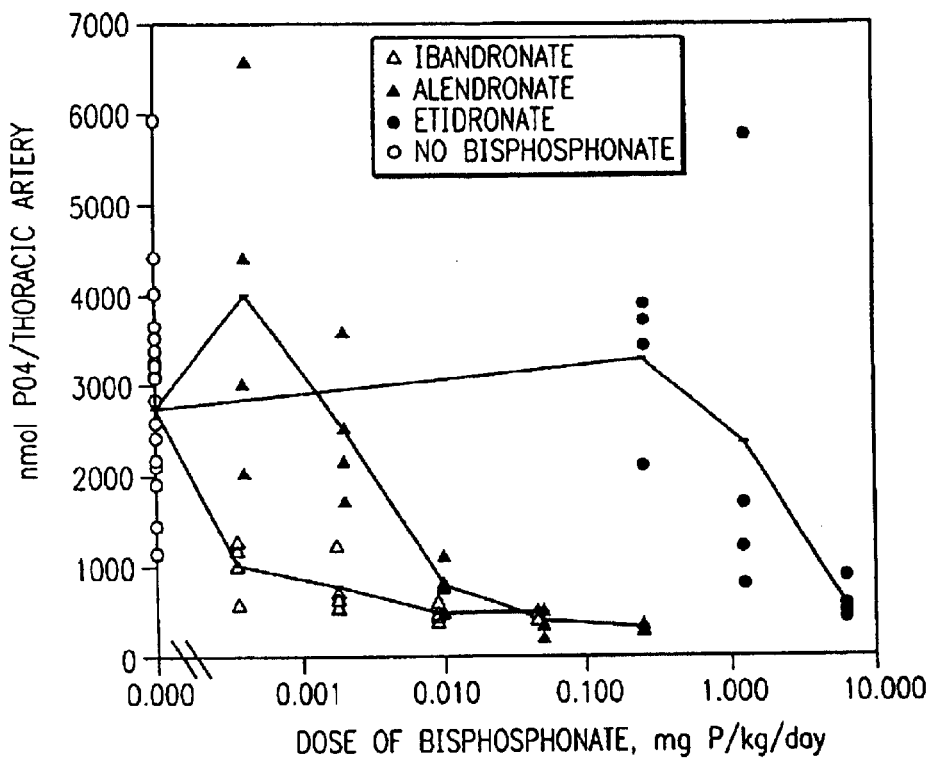
FIG. 3 illustrates the effect of bisphosphonate type and dose on the extent of mineral phosphate accumulation in the thoracic aorta of rats treated with vitamin D plus warfarin. Seventy 7 week old male Sprague Dawley rats were given subcutaneous injections of 300,000 IU vitamin D/kg body weight at t=0, 24, and 48 h. Beginning with the first vitamin D injection, all rats were also treated with subcutaneous injections of vitamin K every 24 h and warfarin every 12 h. Twenty-two rats did not receive a bisphosphonate. The remaining 48 rats were divided among 12 treatment groups and each group was given daily subcutaneous injections of the different bisphosphonates at the doses indicated in the Figure beginning 4 days before the first vitamin D injection. All animals were killed 84 h after the first vitamin D injection and the thoracic aorta segment between the renal branch and the heart was immediately removed from each animal. The level of phosphate in the acid demineralization extract of each artery is shown for all 70 animals, and the lines are drawn to connect the mean values of aorta phosphate in each treatment group (○, no bisphosphonate; Δ, ibandronate; ▲, alendronate; and ●, etidronate). The level of phosphate in the thoracic aorta of untreated control rats of this age is 445+/−104 (X+/−SD) nmol phosphate per thoracic aorta.
Figure 4:
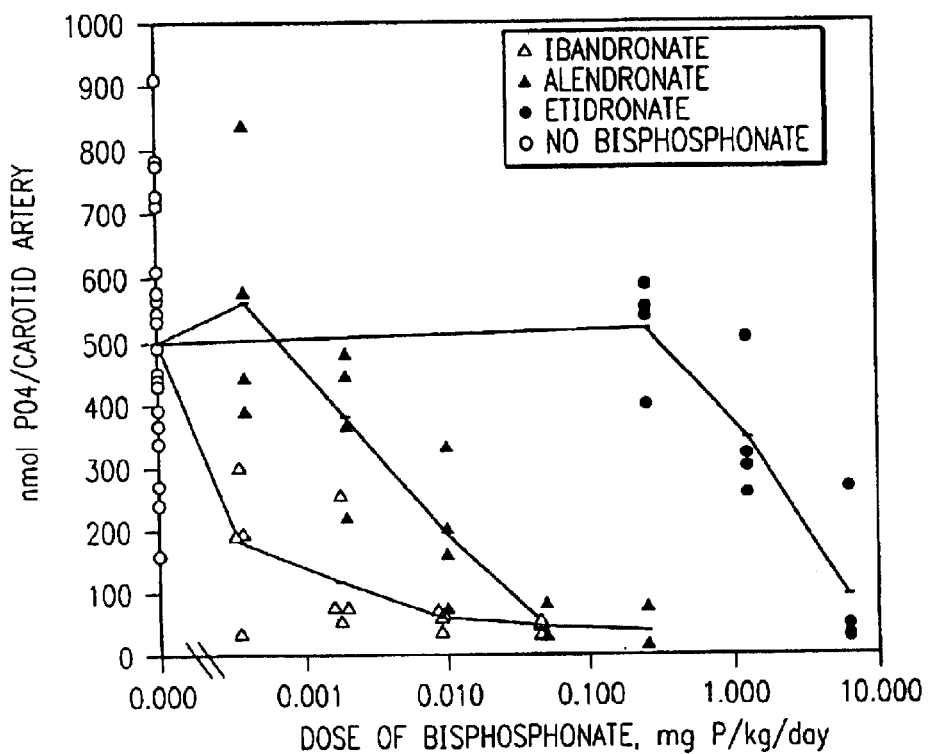
FIG. 4 illustrates the effect of bisphosphonate type and dose on the extent of mineral phosphate accumulation in the carotid arteries of rats treated with vitamin D plus warfarin. Both carotid arteries were removed from each of the 70 animals in the experiment described in the legend to FIG. 3, and the level of phosphate in the acid demineralization extract of the two arteries from each of the 70 animals is shown with lines drawn to connect the mean values of carotid phosphate in each treatment group (○, no bisphosphonate; Δ, ibandronate; ▲, alendronate; and ●, etidronate). The level of phosphate in the carotid artery of untreated control rats of this age is 51+/−22 nmol phosphate per carotid artery.

In the next series of experiments, we established the dependence of artery calcification in vitamin D treated rats on the dose of three bisphosphonate inhibitors of bone resorption, etidronate, alendronate, and ibandronate. In these experiments we examined the extent of artery calcification at 84 h after the first vitamin D dose rather than at 96 h because of the significant mortality observed in rats treated with vitamin D plus warfarin at the 96 h time point. All three bisphosphonates dramatically inhibited artery calcification, and the dose of bisphosphonate required for inhibition correlated with the known differences in the potency of these drugs as inhibitors of bone resorption. Ibandronate and alendronate completely eliminated von Kossa staining for mineral in the abdominal aorta at doses of ibandronate of 0.0018 mg P/kg/day and above and at an alendronate dose of 0.25 mg P/kg/day, and etidronate significantly reduced the extent of von Kossa staining in the abdominal aorta at the highest dose tested, 6.25 mg P/kg/day (Table I). Quantitative analysis of the accumulation of mineral phosphate in the acid demineralization extracts of the thoracic aorta and of the two carotid arteries revealed that the dose of bisphosphonate required to reduce the extent of mineralization by half in the thoracic aorta is 0.0002 mg P/kg/day for ibandronate, 0.005 for alendronate, and 2 for etidronate (FIG. 3) and that the dose required to reduce the extent of mineralization by half in the carotid artery is 0.00018 mg P/kg/day for ibandronate, 0.005 for alendronate, and 2 for etidronate (FIG. 4). The level of mineral phosphate in the acid demineralization extracts of the thoracic aorta and of the two carotid arteries at the two highest doses of alendronate and ibandronate were not significantly above control values, which were 445+/−104 (X+/−SD) nmol phosphate per thoracic aorta and 51+/−22 nmol phosphate per carotid artery.

TABLE I

Effect of bisphosphonate dose on the extent of von Kossa staining for calcification in the thoracic aorta of rats treated with vitamin D plus warfarin (see legends to FIGS. 3 and 4) Seventy 7 week old male Sprague Dawley rats were given subcutaneous injections of 300,000 IU vitamin D/kg body weight at t = 0, 24, and 48 h. Beginning with the first vitamin D injection, all rats were also treated with subcutaneous injections of vitamin K every 24 h and warfarin every 12 h. Twenty two rats did not receive a bisphosphonate. The remaining 48 rats were divided among 12 treatment groups and each group was given bisphosphonates at the doses indicated in the Table beginning 4 days before the first vitamin D injection. All animals were killed 84 h after the first vitamin D injection and the abdominal aorta segment between the renal branch and the femoral bifurcation was immediately removed from each animal and fixed in 10% buffered formalin. Longitudinal sections of each abdominal aorta were stained for mineral by von Kossa, and all sections from each of the 70 animals were examined blindly by two observers, and the extent of calcification was scored with 5 as most calcified and with 0 as no calcification. (n) = number of rats in the indicated treatment group.

| | | Histology Score | | | |
|---|---|---|---|---|---|
| | | Observer #1 | | Observer #2 | |
| Treatment | N | x ± S.D. | Range | x ± S.D. | Range |
| No Bisphosphonate | 22 | 3.2 ± 1.5 | 0.0–5 | 3.4 ± 1.4 | 1–5 |
| Ibandronate: | | | | | |
| 0.00036 mg P/kg/day | 4 | 1.0 ± 0.8 | 0–2 | 1.0 ± 0.8 | 0–2 |
| 0.0018 mg P/kg/day | 4 | 0.0 ± 0.0 | 0–0 | 0.0 ± 0.0 | 0–0 |
| 0.009 mg P/kg/day | 4 | 0.0 ± 0.0 | 0–0 | 0.0 ± 0.0 | 0–0 |
| 0.045 mg P/kg/day | 4 | 0.0 ± 0.0 | 0–0 | 0.0 ± 0.0 | 0–0 |
| Alendronate: | | | | | |
| 0.0004 mg P/kg/day | 4 | 2.8 ± 1.0 | 2–4 | 3.3 ± 1.3 | 2–5 |
| 0.002 mg P/kg/day | 4 | 2.5 ± 0.6 | 2–3 | 2.0 ± 0.8 | 1–3 |
| 0.010 mg P/kg/day | 4 | 2.0 ± 1.8 | 1–5 | 2.5 ± 1.3 | 1–4 |
| 0.050 mg P/kg/day | 4 | 0.8 ± 0.5 | 0–1 | 0.4 ± 0.5 | 0–1 |
| 0.25 mg P/kg/day | 4 | 0.0 ± 0.0 | 0–0 | 0.0 ± 0.0 | 0–0 |
| Etidronate: | | | | | |
| 0.25 mg P/kg/day | 4 | 3.5 ± 1.3 | 2–5 | 4.5 ± 1.0 | 3–5 |
| 1.25 mg P/kg/day | 4 | 1.8 ± 2.4 | 0–5 | 2.0 ± 2.4 | 0–5 |
| 6.25 mg P/kg/day | 4 | 0.3 ± 0.5 | 0–1 | 0.1 ± 0.3 | 0–0.5 |

The dose of bisphosphonate required to inhibit vitamin D-induced artery calcification is compared with the dose of bisphosphonate required to inhibit arotinoid-induced bone resorption in Table II. As seen, the relative potency of etidronate, alendronate, and ibandronate as inhibitors of artery calcification parallels the relative potency of these drugs as inhibitors of bone resorption. The absolute parenteral dose of alendronate and ibandronate needed to inhibit artery calcification by half is actually about 2- to 5-fold lower than the dose required to inhibit arotinoid-induced bone resorption by half. Taken together, these comparisons strongly suggest that the actions of bisphosphonates on bone resorption and artery calcification are linked. The most reasonable hypothesis is that artery calcification is in fact linked to bone resorption.

TABLE II

A comparison of the dose dependence of the effects of bisphosphonates on artery calcification and on bone resorption. The data for the effect of daily subcutaneous dose of bisphosphonate on vitamin D-induced artery calcification is taken from FIGS. 2 and 3. The data for the effect of daily subcutaneous dose of alendronate and ibandronate on arotinoid-induced bone resorption are from FIG. 3 in (Muhlbauer et al. (1991) J. Bone and Mineral Res. 6: 1003–1010), and the relative antiresorption potency of bisphosphonates in the rat is from Table I in (Muhlbauer et al. (1991) J. Bone and Mineral Res. 6: 1003–1010). Note that the bone resorption studies were carried out in male rats initially 200–230 g, and the vitamin D induced artery calcification studies presented here were carried out in male rats initially 200 g.

| | Artery Calcification | | Bone Resorption | |
|---|---|---|---|---|
| Bisphosphonate | Dose for 50% inhibition mg P/kg/day | Relative potency | Dose for 50% inhibition mg P/kg/day | Relative potency |
| Etidronate | 2 | 1 | — | 1 |
| Alendronate | 0.005 | 400 | 0.01 | 1000 |
| Ibandronate | 0.00019 | 10500 | 0.001 | 10000 |

A potentially trivial explanation for the correlation between the bisphosphonate doses required to inhibit artery calcification and bone resorption could be that the hypercalcemia induced by high doses of vitamin D, a potent stimulator of bone resorption, might be reduced by bisphosphonate treatment. As seen in Table III, however, none of the bisphosphonates tested here significantly reduced the increased level of serum calcium caused by vitamin D treatment, which remained at 40% above normal serum calcium levels at all bisphosphonate doses tested. We therefore conclude that the effectiveness of bisphosphonates as inhibitors of artery calcification in the vitamin D-treated rat is not due to a simple reduction in the extent of hypercalcemia induced by treatment with vitamin D. Bisphosphonate treatment did significantly reduce the level of serum phosphate, but the magnitude of the reduction was only about 16% for the two highest doses of alendronate and 11% for the two highest doses of ibandronate (Table III). In repeat experiments using the 0.25 mg P/kg/day dose of alendronate, no significant reduction in serum calcium or phosphate could be demonstrated at 48 h, 60 h, and 72 h after the first vitamin D injection, and so the reduction in serum phosphate levels in the bisphosphonate treated animals occurs relatively late in the time course of vitamin D induced artery calcification.

TABLE III

Effect of bisphosphonate type and dose on serum levels of calcium and phosphate in rats treated with vitamin D plus warfarin. See legend to Table I for a more detailed description of this experiment. Serum calcium and phosphate levels were determined using blood removed from all 70 animals at the end of the experiment, 84 h after the first vitamin D injection. The values given are the mean and standard deviation for serum calcium and phosphate levels in the animals in each bisphosphonate treatment group.

| Bisphosphonate | Dose (mg P/kg/day) | Serum Ca (mg/dL) | Serum P (mg/dl) | N |
|---|---|---|---|---|
| Etidronate | 6.25 | 15.0 ± 0.5 | 8.2 ± 0.4*** | 4 |
| | 1.25 | 13.5 ± 0.7 | 9.5 ± 0.3** | 4 |
| | 0.25 | 13.7 ± 1.2 | 10.8 ± 0.5 | 4 |

TABLE III-continued

Effect of bisphosphonate type and dose on serum levels of calcium and phosphate in rats treated with vitamin D plus warfarin. See legend to Table I for a more detailed description of this experiment. Serum calcium and phosphate levels were determined using blood removed from all 70 animals at the end of the experiment, 84 h after the first vitamin D injection. The values given are the mean and standard deviation for serum calcium and phosphate levels in the animals in each bisphosphonate treatment group.

| Bisphosphonate | Dose (mg P/kg/day) | Serum Ca (mg/dL) | Serum P (mg/dl) | N |
|---|---|---|---|---|
| Alendronate | 0.25 | 14.5 ± 0.1 | 9.5 ± 0.7** | 4 |
|  | 0.05 | 15.5 ± 0.4 | 9.9 ± 0.5* | 4 |
|  | 0.01 | 15.9 ± 0.4 | 10.0 ± 0.9 | 4 |
|  | 0.002 | 13.6 ± 0.2 | 10.2 ± 0.6 | 4 |
|  | 0.0004 | 13.3 ± 0.7 | 10.8 ± 1.2 | 4 |
| Ibandronate | 0.045 | 15.4 ± 0.3 | 9.9 ± 0.4* | 4 |
|  | 0.009 | 14.9 ± 0.6 | 10.4 ± 0.7 | 4 |
|  | 0.0018 | 15.5 ± 0.9 | 10.3 ± 0.6 | 4 |
|  | 0.00036 | 13.8 ± 0.6 | 9.9 ± 0.5* | 4 |
| W/D Control | 0 | 14.5 ± 1.1 | 11.4 ± 1.4 | 22 |

*, $p < 0.05$ when compared with the W/D control;
**, $p < 0.025$ when compared with the W/D control;
***, $p < 0.001$ when compared with the W/D control.

We employed concurrent treatment with the vitamin K antagonist warfarin in all of the experiments discussed above in order to enhance the extent of artery calcification compared to that seen in animals treated with vitamin D alone. In order to establish that the effectiveness of bisphosphonates as inhibitors of artery calcification is not due to a possible interaction between the bisphosphonate and warfarin, we also examined the effectiveness of bisphosphonates as inhibitors of artery calcification in animals treated with vitamin D that were not also treated with warfarin. These experiments demonstrated that 0.01 mg P/kg/day of ibandronate and 0.25 mg P/kg/day of alendronate completely eliminated all von Kossa staining for mineral in the aorta and carotid arteries of the 4 animals in each group when examined at 96 h after the first vitamin D injection, while the 4 animals which did not receive bisphosphonate all had extensive artery calcification (figure not shown). We therefore conclude that the effectiveness of bisphosphonates as inhibitors of artery calcification is equivalent in animals treated with vitamin D alone and in animals treated with vitamin D plus warfarin.

Effect of Timing of Alendronate Administration on the Inhibition of Artery Calcification in Vitamin D-Treated Rats To further address the mechanism by which bisphosphonates inhibit artery calcification, we examined the relationship between the timing of alendronate administration and the extent to which alendronate inhibits artery calcification. The strategy of this experiment was to adjust the timing of alendronate administration so that one group would receive alendronate only during the period prior to artery calcification and another group would receive alendronate only during the period in which artery calcification actually occurs. Animals were given the same doses of vitamin D and warfarin and were divided into four treatment groups based on the timing of the 0.25 mg P/kg/day dose of alendronate: Group A received no alendronate; Group B received alendronate continuously for 8 days, starting 4 days prior to the first vitamin D injection; Group C received alendronate for 6 days, starting 4 days prior to the first vitamin D treatment and ending with the final dose on the second day of vitamin D treatment (at t=24 h); and Group D received alendronate only for the last two days of the 8 day experiment (at t=48 and 72 h).

Figure 5:
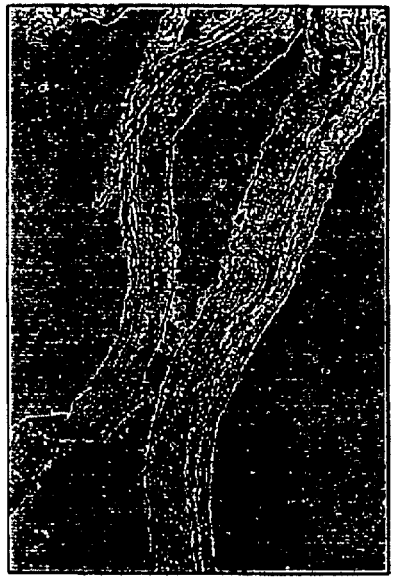
FIG. 5 illustrates the effect of timing of alendronate administration on von Kossa staining of artery calcification in rats treated with vitamin D plus warfarin. Twenty six 7 week old male Sprague Dawley rats were given subcutaneous injections of 300,000 IU vitamin D/kg body weight at t=0, 24, and 48 h. Beginning with the first vitamin D injection, rats were also treated with subcutaneous injections of vitamin K every 24 h and warfarin every 12 h. There were four alendronate treatment groups: 11 animals received no alendronate, 6 received subcutaneous injections of alendronate at 0.25 mg P/kg/day starting four days prior to the first warfarin injection with the eighth and last dose at t=72 h; 6 received alendronate at 0.25 mg P/kg/day starting four days prior to the first warfarin injection with the sixth and last dose at t=24 h; and 9 received alendronate on the last two days only, at t=48 and 72 h. All animals were killed 96 h after the first vitamin D injection and the abdominal aorta segment between the renal branch and the femoral bifurcation was immediately removed from each animal and fixed in 10% buffered formalin. Longitudinal sections of each aorta were stained for mineral by von Kossa. The panels illustrate typical sections from rats that did not receive alendronate (lower right), rats that received alendronate on the last 2 days only (upper right), rats that received alendronate only on the first 6 days (lower left), and rats that received alendronate for all 8 days (upper left).
Figure 5:
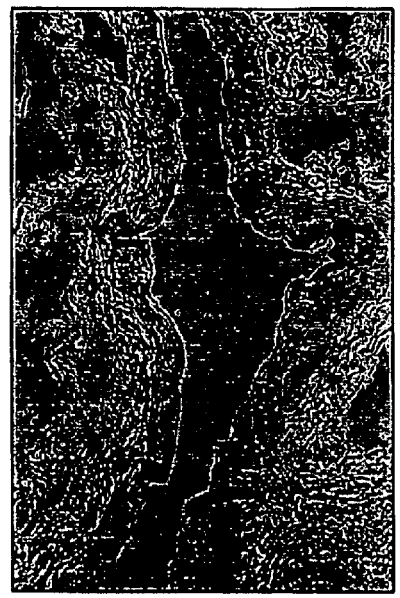
Figure 5:
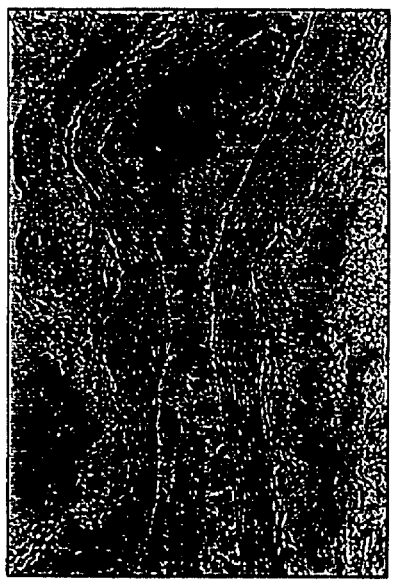
Figure 5:
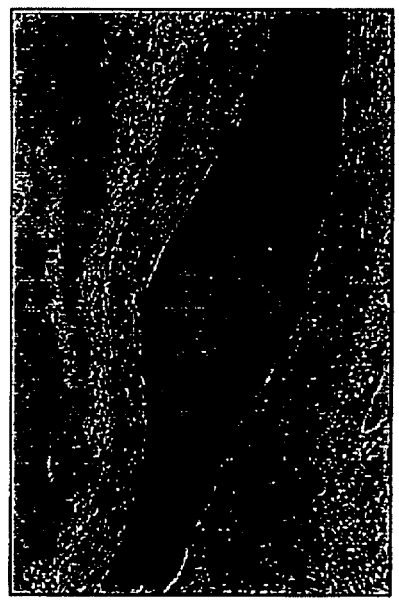

Histochemical examination of mineralization in the abdominal aorta using the von Kossa stain revealed massive calcification in the 11 animals treated with vitamin D alone (group A), reduced levels of calcification in the 9 animals treated with alendronate for the last 2 days of the 8 day experiment (group D), and no evidence of calcification in the 6 animals treated with alendronate for the first 6 days only (group C) and in the 6 animals treated with alendronate for the entire 8 days (group B) (FIG. 5). Quantitative analysis of the accumulation of mineral phosphate in the acid demineralization extracts of the carotid arteries revealed essentially identical results, with very high levels of mineral in the carotid arteries of animals which received vitamin D and no alendronate (FIG. 6), intermediate levels of mineral in the carotid arteries of rats treated with alendronate for the last 2 days of the 8 day experiment (group D), and control levels of mineral in the carotid arteries of rats treated continuously for 8 days with alendronate (group B) and in rats treated with alendronate for the first 6 days only (group C).

The absence of artery calcification in the animals in group C may be revealing as to the mechanism by which bisphosphonates inhibit artery calcification. Since alendronate is cleared rapidly from serum and so would not be expected to be present in the blood of animals in group C during the actual period in which mineralization occurs, the group C results indicate that alendronate need not be present during the actual progression of artery calcification in order to inhibit the calcification process. It is also worth noting that alendronate need not be present during the period of vitamin D-induced hypercalcemia, since serum calcium levels are normal at the time of the last alendronate administration to group C, which is 24 h after the first vitamin D injection, and subsequently rise to 21% above normal at 48 h and to 40% above normal at 72 and 96 h. We believe that the absence of artery calcification in the animals in group C is consistent with the hypothesis that alendronate inhibits artery calcification by virtue of its ability to inhibit bone resorption, since treatment of animals in group C with alendronate for the first 6 days should inhibit resorption through the last two days of the experiment due to the long term action of the drug on osteoclasts (FIG. 6 in Antic et al. (1996) Calcif. Tissue Int. 58: 443–448).

Figure 6:
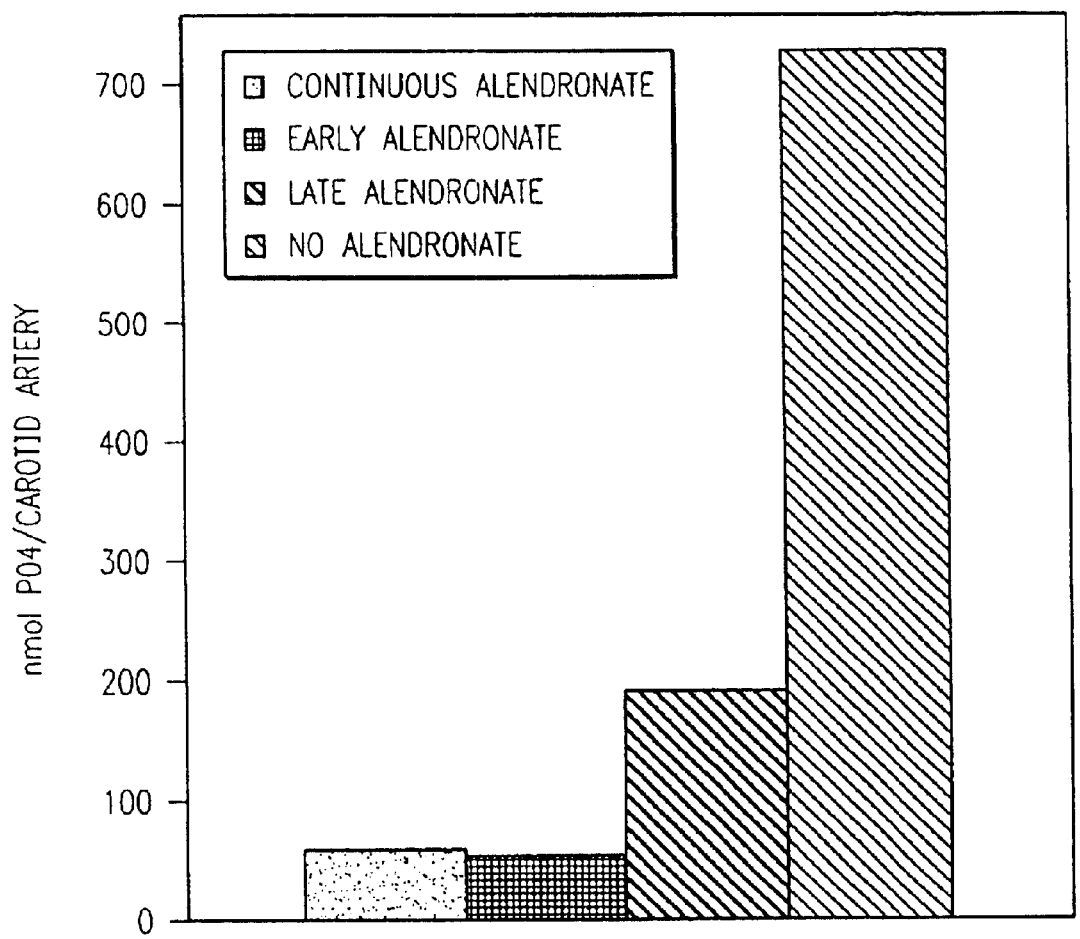
FIG. 6 illustrates the effect of timing of alendronate administration on the extent of mineral phosphate accumulation in the carotid arteries of rats treated with vitamin D plus warfarin. Both carotid arteries were removed from each of the 26 animals in the experiment described in the legend to FIG. 5, and the mean level of phosphate in the acid demineralization extract of the two carotid arteries from each animal in the respective 4 treatment groups are shown. No Alendronate, rats that did not receive alendronate; Late Alendronate, rats that received alendronate only on the last 2 days; Early Alendronate, rats that received alendronate only on the first 6 days; Continuous Alendronate, rats that received alendronate for all 8 days. The level of phosphate in the carotid artery of untreated control rats of this age is 51+/−22 nmol phosphate per carotid artery.

It should be noted that treatment with alendronate during the actual period in which mineralization occurred, the last two days of the experiment, did not completely inhibit artery calcification (FIGS. 5 and 6). This result is also consistent with the hypothesis that alendronate acts by inhibiting bone resorption, since resorption will be only partially inhibited by two days of treatment with this drug (Antic et al. (1996) Calcif. Tissue Int. 58: 443–448). This result is not, however, consistent with the hypothesis that alendronate inhibits artery calcification by virtue of its ability to interact directly with mineral surfaces and so inhibit crystal growth by a direct physicochemical mechanism, since the animals in group D received alendronate throughout the entire period in which artery calcification actually occurred (that is, 48 to 96 h after the first vitamin D injection) and nevertheless had significant artery calcification.

Effect of Bisphosphonates on Artery Calcification in Rats Treated with Warfarin

Figure 7:
FIG. 7 illustrates the effect of alendronate treatment on von Kossa staining for aorta calcification in rats treated with warfarin for two weeks. Twelve 42 day old male Sprague Dawley rats were treated with warfarin every 12 h and with vitamin K every 24 h for 2 weeks. Starting 4 days prior to the first warfarin injection, 4 rats received alendronate at 0.25 mg P/kg/day, 4 rats received ibandronate at 0.01 mg P/kg/day, and 4 rats received no bisphosphonate. The abdominal aorta segment between the renal branch and the femoral bifurcation was removed immediately after the rats were killed and fixed in 10% buffered formalin, and longitudinal sections of each aorta were stained for mineral by von Kossa. The panels illustrate the typical level of calcification seen in the aorta from two animals in each treatment group. No calcification can be detected in untreated control animals at this age.
Figure 7:
Figure 7:
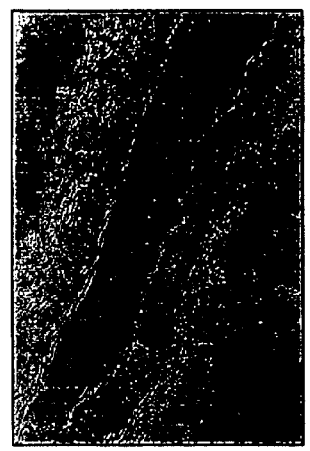
Figure 7:
Figure 7:
Figure 7:
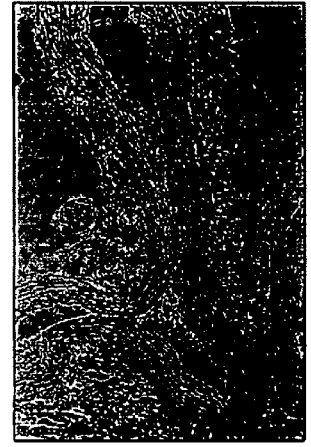

In order to examine the relationship between bone resorption and artery calcification in rats treated with warfarin, rats were treated with warfarin for 2 weeks, which is the minimum treatment period required for warfarin-induced artery calcification, together with bisphosphonates at doses which proved to be effective in inhibiting artery calcification in the vitamin D treated rat. In each case, the daily bisphosphonate treatment was begun 4 days prior to the start of warfarin treatment because previous studies have shown that it takes about 4 days for bisphosphonates to completely inhibit bone resorption (Antic et al. (1996) *Calcif. Tissue Int.* 58: 443–448). All 8 of the rats treated with warfarin alone had extensive calcification of the abdominal aorta, in agreement with earlier studies (Price et al. (1998) *Arterioscler. Thromb. Vasc. Biol.* 18: 1400–1407), while no calcification could be detected in the abdominal aorta of any of the 4 animals treated with warfarin together with alendronate at 0.25 mg P/kg/day. Two of the four animals treated with warfarin together with ibandronate at 0.01 mg P/kg/day had no evidence of calcification in their abdominal aorta, while one had a single small calcification foci and the other had two small calcification foci. These foci were much less intensely stained than the typical calcification foci found in rats treated with warfarin alone. Representative histological sections of the abdominal aorta from each group are shown in FIG. 7. The effect of the 0.25 mg P/kg/day dose of alendronate was examined in a repeat two week warfarin treatment experiment, and again no calcification could be detected in the abdominal aorta of any of the 4 alendronate treated rats.

Figure 8:
FIG. 8 illustrates the effect of alendronate treatment on von Kossa staining for aorta calcification in rats treated with warfarin for four weeks. Fourteen 42 day old male Sprague Dawley rats were treated with warfarin every 12 h and with vitamin K every 24 h for 2 weeks. Starting 4 days prior to the first warfarin injection, 3 rats received alendronate at 0.25 mg P/kg/day, 3 rats received alendronate at 0.025 mg P/kg/day, and 8 rats did not receive alendronate. The abdominal aorta segment between the renal branch and the femoral bifurcation was removed at necropsy and fixed in 10% buffered formalin, and longitudinal sections of each aorta were stained for mineral by von Kossa. The panels illustrate the typical level of calcification seen in the aorta from an animal in each treatment group.
Figure 8:
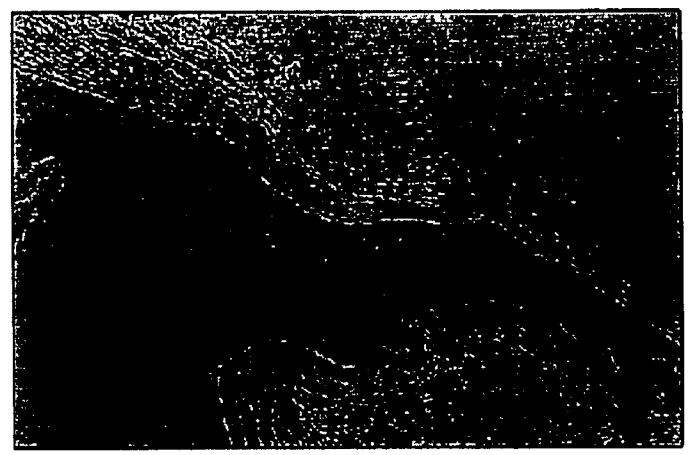
Figure 8:
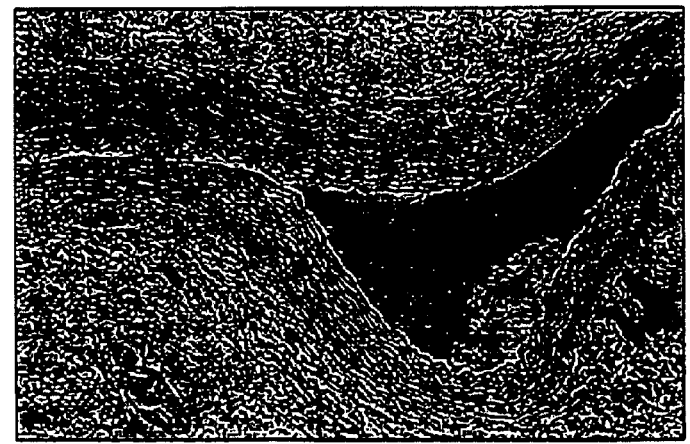

The effect of alendronate and etidronate on warfarin-induced artery calcification was also examined in rats treated for four weeks with warfarin because a longer period of warfarin treatment is necessary in order to achieve calcification levels which can be measured accurately by quantitative analysis of acid demineralization extracts (Price et al. (1998) *Arterioscler. Thromb. Vasc. Biol.* 18: 1400–1407). Rats were again pretreated for 4 days with the bisphosphonate alone, and then treated with the bisphosphonate plus warfarin for a total warfarin treatment time of four weeks. As shown in Table IV and FIG. 8, alendronate treatment produced a dose dependent decrease in the level of mineral phosphate in the carotid arteries without affecting bone growth or weight gain. Etidronate also inhibited calcification of the carotid artery, but the dose needed for this effect is sufficiently high that it inhibits weight gain (Table IV). The final length of the tibia in the 4 animals treated with etidronate plus warfarin (3.59±0.03 cm) was also significantly lower than the length of tibia in the 8 treated with warfarin alone (3.80±0.04 cm, p<0.001).

TABLE IV

Effect of alendronate and etidronate on the accumulation of mineral phosphate in the carotid arteries of rats treated for 4 weeks with warfarin. Beginning at 42 days of age, 18 male rats were given sbucutaneous injections of vitamin K every 24 h and warfarin every 12 h for 4 weeks and 11 control rats received no warfarin. Beginning 4 days prior to the first warfarin injection, three warfarin treated rats received alendronate at a dose of 0.25 mg P/kg/day. All animals were exsanguinated at 4 weeks and both carotid arteries were removed and demineralized with acid. Phosphate levels were determined in all acid extracts, and the mean and SD for phosphate levels in both carotid arteries are shown for each treatment group. Also shoen in the table are average serum calcium and phosphate levels for each group determined on the blood obtained from animals at the end of the experiment, and the average beginning and final weights of the animals.

| Treatment | Number of Rats | Starting wt (gm) | Ending wt (gm) | nmol PO$_4$ Carotid | mg Ca dl serum | mg P dl serum |
|---|---|---|---|---|---|---|
| None | 11 | N.D. | N.D. | 49.4 ± 28.4 | 10.1 ± 0.6 | 9.8 ± 1.0 |
| Warfarin Only | 8 | 149 ± 6 | 301 ± 10 | 735.2 ± 476.1 | 11.1 ± 0.6 | 11.0 ± 1.4 |
| Warfarin + Alendronate | | | | | | |
| 0.025 mg P/kg/day | 3 | 134 ± 6 | 301 ± 8 | 374.0 ± 217.4 | 10.0 ± 0.1 | 10.0 ± 0.1 |
| 0.25 mg P/kg/day | 3 | 151 ± 3 | 300 ± 5 | 63.7 ± 43.1 | 10.8 ± 0.1 | 10.9 ± 0.7 |
| Warfarin + Etidronate | | | | | | |
| 6.25 mg P/kg/day | 4 | 154 ± 4 | 238 ± 11 | 55.2 ± 14.5 | 10.9 ± 0.8 | 8.1 ± 0.6 |

Calcium and phosphate levels were determined in serum obtained at exsanguination for all animals in the 2 and 4 week warfarin treatment experiments, and in no instance were serum calcium or phosphate levels significantly affected by treatment either with warfarin alone or with warfarin in conjunction with a bisphosphonate (data not shown). This result indicates that the effectiveness of bisphosphonates as inhibitors of warfarin-induced calcification of arteries is not due to an effect of bisphosphonates on serum levels of calcium and phosphate.

Discussion

A major conclusion of the present study is that bisphosphonates inhibit the calcification of arteries, heart valves, and kidneys by virtue of their ability to inhibit bone resorption in three artery calcification models, treatment with vitamin D, treatment with vitamin D plus warfarin, and treatment with warfarin alone. The previous hypothesis to explain the ability of high etidronate doses to inhibit artery calcification is probably incorrect, and alendronate and ibandronate, which are members of the newer generation of bisphosphonates developed to more potently inhibit bone resorption, clearly do not inhibit artery calcification by virtue of their ability to directly interact with mineralization sites and thereby inhibit artery calcification by a physico-chemical mechanism. This new conclusion is supported by several lines of evidence: 1. The actual daily subcutaneous doses of alendronate and ibandronate which are required to inhibit artery calcification are in good agreement with the daily subcutaneous doses of these drugs which are required to inhibit bone resorption in male rats of this age (Table II). In contrast, the dose of these drugs required to inhibit normal bone mineralization in vivo, 5 mg P/kg/day, is over 1000 fold greater than the dose required to inhibit artery calcification. 2. The 10,500 fold difference in the doses of the etidronate and ibandronate that are required to inhibit artery calcification is in excellent agreement with the 10,000 fold difference in the doses of the same bisphosphonates that are required to inhibit bone resorption (Table II). This is in marked contrast to the essentially identical doses of etidronate and ibandronate that are required to inhibit normal bone mineralization in vivo (Fleisch (1998) *Endocrine Rev.* 19: 80–100; Fleisch (1997) *Ann. Med.* 29: 55–62.). 3. Studies on the timing of alendronate administration that is required to inhibit artery calcification (FIGS. 5 and 6) demonstrate that the drug is completely effective in inhibiting artery calcification even when administered prior to the first appearance of mineral in the artery and prior to the appearance of vitamin D-induced hypercalcemia. This result is difficult to reconcile with the hypothesis that alendronate inhibits artery calcification by a direct physicochemical mechanism analogous to the mechanism by which it inhibits mineralization in vitro and is thought to inhibit normal bone mineralization in vivo. Because the inhibition of bone resorption by alendronate is known to persist for at least 10 days after the daily administration of the drug is discontinued in male rats of this age (FIG. 6 in Antic et al. (1996) *Calcif. Tissue Int.* 58: 443–448), however, this result is entirely consistent with the conclusion that alendronate inhibits artery calcification by virtue of its ability to inhibit bone resorption.

The discovery that bisphosphonates inhibit artery calcification by virtue of their ability to inhibit bone resorption may well be clinically significant. The previous hypothesis, that the mechanism by which bisphosphonates inhibit artery calcification is related to the mechanism by which they inhibit bone mineralization, led investigators to conclude that bisphosphonates could not be employed as inhibitors of soft tissue calcification without inhibiting normal bone mineralization. To quote from a 1998 review (Fleisch (1998) *Endocrine Rev.* 19: 80–100): "Unfortunately, however, when administered in doses approximating those that inhibit soft tissue calcification, bisphosphonates can impair the mineralization of normal calcified tissues such as bone and cartilage and, when given in higher amounts, also dentine, enamel, and cementum." and "The propensity to inhibit the calcification of normal bone has hampered the therapeutic use of bisphosphonates in ectopic calcification." Our data support the conclusion that etidronate doses which inhibit artery calcification and other ectopic calcifications also inhibit bone mineralization (Table IV), but show for the first time that the newer class of bisphosphonates, such as alendronate and ibandronate, inhibit artery calcification at doses far below the doses which inhibit normal mineralization. The doses of these drugs which inhibit artery calcification are in fact the doses which inhibit bone resorption, and so it seems possible that the inhibition of the calcification of arteries and soft tissues could be an unanticipated and beneficial side effect of doses of these drugs already used in clinical practice to inhibit bone resorption. In this context it is worth noting that the intravenous dose of ibandronate used to inhibit bone resorption in human subjects, 1 mg ibandronate over a 24 h period, translates to an ibandronate dose of 10 $\mu$g P/kg/day for a 50 kg human. This is well above the 0.2 $\mu$g P/kg/day subcutaneous ibandronate dose required for 50% inhibition of artery calcification in the rat (FIGS. 3 and 4).

There are several human diseases in which calcification plays a role, and in which there could be a therapeutic advantage to treating patients with the newer bisphosphonates at doses which are sufficient to inhibit bone resorption but are far below the doses which inhibit normal bone mineralization. From the viewpoint of human health, the most important of these are diseases which affect arteries and heart valves. Since these are the two tissues in which we have here demonstrated the profound ability of low doses of bisphosphonates to inhibit calcification, it seems appropriate to briefly review the human diseases in which artery or heart valve calcification plays a role.

Artery calcification is associated with arteriosclerosis, a term which is derived in part from the Greek word for hardness, sklerosis. Arteriosclerosis refers to hardening of arteries, and the types of arteriosclerosis include atherosclerosis, Monckeberg's arteriosclerosis, hypertensive arteriosclerosis, and arteriolosclerosis. Atherosclerosis is the most prevalent arteriosclerosis, and calcification is typically associated with the atherosclerotic plaque itself. While the relationship between calcification and the progression of atherosclerosis is presently unclear, previous studies have found strong associations between coronary artery disease and the presence of coronary artery calcification identified by autopsy, by computed tomography, and by fluoroscopy (Bartel et al. (1974) *Circulation*, 49: 1247–1253; Blankenhorn (1961) *Am. J. Med. Sci.* 242: 41–49; Simons, et al. (1992) *AJ. Am. Coll. Cardiol.* 20: 1118–1126). Recent studies have also shown that coronary artery calcification is a more sensitive marker for coronary atherosclerosis than other noninvasive techniques (Detrano et al. (1994) *J. Am. Coll. Cardiol.* 24: 354–358; Puentes et al. (1995) *Am. J. Card. Imaging.* 9(suppl 1): 5; Kaufmann et al. (1995) *J. Am. Coll. Cardiol.* 25: 626–632) and that the presence of coronary artery calcification predicts future coronary artery disease morbidity and mortality in asymptomatic and symptomatic adults (Detrano et al. (1996) *J. Am Coll. Cardiol.* 27: 285–290).

It is also worth noting that, in rabbit (Rosenblum et al. (1975) *Atherosclerosis.* 22:411–424) and monkey (Kramsch et al. (1981) *Science* 213:1511–1512 ) models of atherosclerosis, high doses of the bisphosphonate etidronate have been shown not only to inhibit artery calcification, but also to inhibit the accumulation of cholesterol in the artery. High etidronate doses have also been shown to cause the regression of pre-established atherosclerosis in the cholesterol fed New Zealand white rabbit model (Hollander et al. (1979) *Atherosclerosis* 33: 111–123; Zhu et al. (1994) *Cardiology* 85:370–377). As noted above, etidronate is a first generation bisphosphonate and inhibits bone resorption, artery calcification, and normal bone mineralization at comparably high doses. In the studies of etidronate and atherosclerosis cited above, the high doses of etidronate needed to inhibit artery calcification and atherosclerosis do indeed affect normal bone mineralization (Zhu et al. (1994) *Cardiology* 85:370–377). We have here shown for the first time that the newer bisphosphonates can be used to inhibit artery calcification at doses which inhibit bone resorption, but which are at least 1000 times lower than the doses which inhibit normal bone mineralization.

Arteriosclerosis is also frequently associated with uremia and, in dialysis patients, the frequency of artery calcification increases with the duration of dialysis to an incidence of 92% at 16 years (Goldsmith et al. (1997) *Nephron.* 77:37–43). There are two patterns of vascular calcification in uremic patients, calcification of axial arteries (aorta, femoral, iliac) and calcification of peripheral arteries. The latter calcification, referred to as arteriolosclerosis, can lead to cutaneous necrosis and ulceration and is associated with high mortality (Coates et al. (1998) *Am. J. Kidney Dis.* 32: 384–391; Hafner et al. (1995) *J. Am. Acad. Dermatol.* 33:954–962). A recent study of 7,096 hemodialysis patients has identified the serum calcium X phosphate product as an independent risk factor for death, with a relative mortality risk of 1.34 (Block et al. (1998) *Am. J. Kidney Diseases.* 31:

607–617). While the mechanism by which the serum calcium X phosphate product affects mortality in uremic patients has not yet been established, the rate of calcification is known to be exponentially dependent on the calcium X phosphate product. It is therefore tempting to speculate that dystrophic calcification does indeed account for increased mortality in uremic patients.

Heart valve calcification is frequently associated with valvular dysfunction. In a recent study of 236 aortic heart valves excised at the Mayo Clinic in 1990 (Dare et al. (1993) *Human Pathology*. 24:1330–1338), stenosis related to calcification was found in 64% of the excised valves and pure insufficiency without calcification was found in 25%. Ten percent of the heart valves had both stenosis and insufficiency, in these valves insufficiency was typically secondary to degenerative calcification. The prevalence of aortic heart valve calcification increases with age, and in a recent study was detected incidentally on CT scans in 30% of the subjects examined (Lippert et al. (1995) *Am. J. Roentgenology*. 164:73–77). Fifteen percent of the subjects with incidental heart valve calcification were found to have abnormal aortic valve gradients at echocardiography, while none of the subjects without aortic valve calcification had abnormal aortic valve gradients. Calcification is also the major cause of structural valve degeneration in aortic valve bioprotheses (Jamieson et al. (1995) *Ann. Thorac. Surg.* 60:S241-S247; Schoen et al. (1988) *Cardiovasc. Clin.* 18:289–317; Cohn et al. (1989) *Ann. Surg.* 210:435–443) and it is possible that bisphosphonates could inhibit such calcification and thereby reduce the frequency of bioprosthetic valve failure.

We believe that the probable mechanism by which osteoclastic bone resorption promotes artery calcification is by the generation of calcium phosphate crystal nuclei. Some of these nuclei escape to blood and are subsequently deposited in the elastic lamella of arteries and at other soft tissue sites. These nuclei are then able to grow at the deposition sites, due to the fact that serum is supersaturated with respect to calcium phosphate mineral phases such as hydroxyapatite. Our hypothesis is supported in part by evidence that, under some circumstances, a protein mineral complex is released from bone and can be detected in blood.

Example 2

Synthesis and Use of a Fetuin-mineral Comples

Background

We discovered the existence of a complex between a calcium phosphate mineral phase and the serum protein fetuin in the course of investigating the effects of high etidronate doses on the chemical composition of serum in rats. To confirm the chemical composition and nature of this complex, we developed the methods for creating the complex in vitro which are described below.

In a preferred embodiment, the creation of a fetuin mineral complex involves the creation of a solution which is supersaturated with respect to the calcium phosphate mineral phase. This is done in the presence of fetuin at physiological pH (that is, pH values found in serum). In the two procedures outlined below, we have generated the supersaturated conditions by the rapid mixing of calcium and phosphate solutions in order to generate mineral nuclei by a homogeneous nucleation process. It was one of the discoveries of this research that the presence of fetuin arrests the growth and aggregation of the mineral phase so that many small crystallites are formed. Since the size of these crystallites is small, the solution itself remains clear for many days at room temperature in spite of the presence of rather large amounts of the fetuin mineral complex.

Procedures

Procedure for the Preparation of Fetuin Mineral Complex Using Fetal Calf Serum, Calcium, and Phosphate A first approach to preparing a fetuin-mineral complex uses fetal calf serum. The fetal calf serum is brought and about 2 ML is aliquoted into a test tube. Then 0.5 mL of 1 M HEPES (pH 7.4) is added to the fetal calf serum to give a final concentration of 0.2 M HEPES. (The buffer is added at this step in order to prevent a drop in the pH of the solution due to the formation of the mineral phase. If buffer is not present the pH decreases and rather large crystals of brushite form and precipitate.) Then 160 $\mu$l of 0.5 M phosphate buffer* into a 12×75 mm tube.

About 80 $\mu$l of 1 M $CaCl_2$.is placed into a separate 12×75 mm tube. Then 1 mL of the fetal calf serum-HEPES buffer solution prepared above is added to both tubes. The calcium containing tube is covered with parafilm and a hole is poked through the parafilm with a pipette tip. Using a Pasteur pipette and a rubber bulb, the contents of the $PO_4$ tube is rapidly added to that of the Ca tube. (It is critical that mixing be as close to instantaneous as possible at this step in order to create conditions which favor homogeneous nucleation of the mineral phase. Leisurely mixing of the two solutions will form large crystals of calcium phosphate mineral, which are evident as a cloudy precipitate which sinks to the bottom of the tube.) (The order of mixing can be reversed, and the calcium containing solution can be added to the phosphate containing solution.)

The mixture is then re-covered with parafilm and left at room temperature. The size of the crystallites which form are so small that they can only be seen by transmission electron microscopy. Within a few minutes, small spherical crystallites form. These grow and change in structure over the next 3 h to generate numerous crystallites of fairly uniform size. Once the final size is obtained, it remains stable over a period of many days.

Procedure for the Preparation of the Fetuin Mineral Complex Using Purified Bovine Fetuin, Calcium, and Phosphate A second approach to preparing a fetuin-mineral complex uses purified bovine fetuin, calcium, and phosphate fetal calf serum. First, 50 mg of purified bovine fetuin are dissolved in 2.5 mL of 0.2 M HEPES pH 7.4. The mixture is spun at top speed for 30 minutes in an epifuge to clarify the solution. (The Sigma fetuin we use in these experiments contains a small portion of protein which does not dissolve in this buffer.) About 160 $\mu$l of 0.5 M Phosphate buffer* is placed into a 12×75 tube. In a separate 12×75 tube is placed 80 $\mu$l of 1 M $CaCl_2$. 1 mL of the fetuin-HEPES buffer solution prepared in step 2 is rapidly added to both tubes.

The tube containing calcium is covered with parafilm and a hole is poked in the parafilm with a pipette tip. Using a Pasteur pipette and a rubber bulb, rapidly add the contents of the $PO_4$ tube is rapidly added to that of the Ca tube. (It is critical that mixing be as close to instantaneous as possible at this step in order to create conditions which favor homogeneous nucleation of the mineral phase. Leisurely mixing of the two solutions will form large crystals of calcium phosphate mineral, which are evident as a cloudy precipitate which sinks to the bottom of the tube.) (The order of mixing can be reversed, and the calcium containing solution can be added to the phosphate containing solution.)

The mixture is re-covered with parafilm and left at room temperature. The size of the crystallites which form are so small that they can only be seen by transmission electron microscopy. Within a few minutes, small spherical crystallites form. These grow and change in structure over the next 3 h to generate numerous crystallites of fairly uniform size. Once the final size distribution is obtained, it remains stable over a period of many days.

The phosphage buffer used above is prepared by preparing 50 mL of 0.5 M $Na_2HPO_4$ (Dibasic) and 25 mL of 0.5 M $NaH_2PO_4$ (Monobasic). The dibasic it titrated to pH 7.4 with the monobasic solution. Then sodium azide is added to a to a final concentration of 0.02% as a preservative. (This step is optional.)

Modifications of Procedures

The initial concentrations of calcium and phosphate can be varied considerably. In the above experiments the final ion composition is slightly less than 40 mM in calcium and phosphate. We have formed the complex using final ion compositions as low as 5 mM in calcium and phosphate; the major difference is that the complex forms slowly over a period of several days under these conditions. The crystallites which form are still too small to be visualized as cloudiness in the solution, which remains clear, and no crystals sink to the bottom of the tube. The crystallites can be seen by transmission electron microscopy, and are similar in size and structure to those formed after 3 h at room temperature in the experiments outlined above. We have also formed the fetuin mineral complex using initial molar ratios of calcium to phosphate ranging from 2:1 to 0.5:1, and find that the final crystallites formed are identical in properties and structure to those formed under the 1:1 molar ratio conditions.

The fetuin mineral complexes formed by the above procedures can be sedimented by centrifugation for 5 to 30 minutes at high speed in an epifuge. The pellet which forms is translucent and glassy in appearance, and contains fetuin, calcium, and phosphate. The molar ratio of calcium to phosphate in this complex is about 1.25 and the weight ratio of fetuin to calcium in this complex is about 3.

The temperature of the calcium phosphate mixture can be varied. We have also prepared the complex at 7 and 37° C. The complex forms more rapidly at the higher temperature and more slowly at the lower, but the final crystallites formed are identical in properties and structure to those formed at room temperature.

The initial concentration of purified bovine fetuin can be varied. We have successfully formed the fetuin mineral complex using fetuin at 5 mg/ml and an initial ion composition of 10 mM calcium and phosphate, and using fetuin at 1 mg/ml and an initial ion composition of 5 mM calcium and phosphate. In general, less fetuin is required to form a stable complex of uniform size and structure at lower initial concentrations of calcium and phosphate.

The species source of fetuin can be varied. While we have not investigated complex formation using purified fetuin from other species, we have successfully formed the fetuin mineral complex using rat and human serum starting with initial calcium and phosphate concentrations of 10 mM. (Human fetuin is also called α2-HS Glycoprotein.)

Because the rate of homogeneous crystal nucleation is strongly dependent on the initial ion composition, the importance of mixing rapidly is greatest at the higher calcium phosphate concentrations. If time is not a factor, it is easier to mix rapidly enough to create homogeneous nucleation conditions using a low initial ion concentrations, and it is therefore these conditions which favor the formation of fetuin mineral complexes which are the most uniform in structure.

Example 3

A Fetuin-MGP-Mineral Complex in Serum

In this example, study we report the discovery of a novel protein-mineral complex in the serum of rats treated with doses of the bone-active bisphosphonate etidronate that inhibit normal bone mineralization. The composition of this high molecular weight protein-mineral complex consists of about 18% mineral, 80% fetuin, and 2% matrix Gla protein (MGP) by weight, and the presence of the complex in serum after an injection of 8 mg etidronate/100 g body weight elevates calcium by 1.8 fold (to 4.3 mM), phosphate by 1.6 fold (to 5.6 mM), and MGP by 25 fold (to 12 μg/ml). The serum mineral complex reaches maximal levels at 6 h following subcutaneous injection of etidronate, and is subsequently cleared from serum by 24 h. This highly specific complex of fetuin, MGP, and mineral prevents the growth, aggregation, and precipitation of the mineral component, which indicates that the previously reported calcification inhibitory activities of fetuin and MGP may be related to their ability to form stable complexes with nascent mineral nuclei. Treatment with the vitamin K-antagonist warfarin prevents the increase in serum MGP following etidronate injection, which shows that the increase in serum MGP is due to new synthesis and that the γ-carboxylation of MGP is necessary for its binding to the serum mineral complex.

Introduction

The initial objective of the present investigations was to understand how matrix Gla protein (MGP[1]) inhibits the abnormal calcification of arteries and other soft tissues. Recent genetic and biochemical studies have established MGP as the first protein known to act as a calcification inhibitor in vivo. In humans, defects in the MGP gene that predict a non-functional MGP protein have been shown to be responsible for Keutel syndrome (Munroe et al. (1999) *Nature Genetics* 21: 142–144), a rare inherited disease characterized by multiple peripheral pulmonary artery stenoses, by abnormal calcification of cartilages, including costal, nasal, auricle, trachael, and growth plate cartilage, and by nasal hypoplasia and brachytelephalangia (Keutel et al. (1972) *Birth Defects: Orig. Artic. Ser. VIII*(5), 60–68; Teebi et al. (1998) *Am. J. Med. Genet.* 77: 182–187). In mice, targeted deletion of the MGP gene causes rapid calcification of the elastic lamellae of the arterial media which begins at birth and is sufficiently extensive by 3 to 6 weeks of age that the arteries become rigid tubes which fracture, causing death by exsanguination in most of the affected mice by 6 weeks of age (Luo et al. (1997) *Nature* 386: 78–81). MGP deficient mice also display abnormal calcification of growth plate and tracheal ring cartilage. Finally, treatment of rats with the vitamin K antagonist warfarin at doses which inhibit the γ-carboxylation of MGP causes rapid calcification of elastic lamellae of arteries and of aortic heart valves, and increased expression of MGP mRNA in the calcifying artery (Price et al. (1998) *Arterioscler. Thromb. Vasc. Biol.* 18: 1400–1407; Price et al. (2000) *Arterioscler. Thromb. Vasc. Biol.* 20: 317–327).

Matrix Gla protein is a 10 kDa secreted protein which was originally discovered in demineralization extracts of bone, but is now known to be expressed by a wide variety of tissues and cell types. The rat tissues with the highest levels of MGP mRNA are cartilage, heart, kidney, and lung (Fraser and Price (1988) *J. Biol. Chem.* 263: 11033–11036; Hale et al. (1988) *J. Biol. Chem.* 263: 5820–5824) and cells known to express MGP mRNA include osteoblasts, chondrocytes, vascular smooth muscle cells, pneumocytes, kidney cells, and fibroblasts (Fraser and Price (1988) *J. Biol. Chem.* 263: 11033–11036; Hale et al. (1988) *J. Biol. Chem.* 263: 5820–5824; Fraser, J. D., Otawara, Y., and Price, P. A. (1988) *J. Biol. Chem.* 263, 911–916; Shanahan et al. (1993) *Circulation Res.* 73: 193–204; Rannels et al. (1993) *Amer. J. Physiol.* 265: L270-L278; Cancela and Price (1992) *Endocrinology* 130: 102–108).

While several noncalcified tissues do express MGP mRNA at a higher level than bone, significant levels of the protein itself have only been found in bone and calcified cartilage (Hale et al. (1988) *J. Biol. Chem.* 263: 5820–5824; Fraser, J. D., Otawara, Y., and Price, P. A. (1988) *J. Biol. Chem.* 263, 911–916; Shanahan et al. (1993) *Circulation Res.* 73: 193–204; Rannels et al. (1993) *Amer. J. Physiol.* 265: L270-L278; Cancela and Price (1992) *Endocrinology* 130: 102–108; Rice et al. (1994) *J. Bone Min. Res.* 9: 567–576). This observation suggests that the protein may accumulate at sites of calcification, and that much of the protein secreted by noncalcified tissues probably escapes to plasma, where MGP is found at 0.3 to 1 $\mu$g/ml depending on the species. MGP contains 5 residues of the vitamin K-dependent calcium binding amino acid, $\gamma$-carboxyglutamic acid (Gla) (Price et al. (1983) *Biochem. Biophys. Res. Comm.* 117: 765–771; Price and Williamson (1985) *J. Biol. Chem.* 260: 14971–14975) and 3 residues of phosphoserine located at conserved N-terminal sequence positions in MGP from shark, rat, cow, and human tissues (Price et al. (1994) *Protein Sci.* 3: 822–830). Specific proteolytic cleavage at a conserved dibasic site in the C-terminal region has also been observed for MGP isolated from human, bovine, and shark tissues (Rice et al. (1994) *J. Bone Min. Res.* 9: 567–576; Hale et al. (1991) *J. Biol. Chem.* 266: 21145–21149).

The original objective of the present study was to use the geminal bisphosphonate etidronate (ethylhydroxybisphosphonate) to probe the function of MGP in bone metabolism. These studies were prompted by the fact that etidronate and MGP both bind strongly to bone mineral, and by previous studies that showed that etidronate competes with bone Gla protein (BGP; osteocalcin), a related vitamin K dependent protein, for binding to hydroxyapatite in vitro, and that etidronate injection into a rat produced a transient 3 fold elevation in serum BGP levels (Price et al. (1981) in *The Chemistry and Biology of Mineralized Connective Tissues.* (Veis, A., ed) Vol. 1, pp. 327–335., Elsevier, North Holland). We report here that etidronate produced an over 25-fold elevation in serum levels of MGP within 6 h, and that this elevation is caused by the unexpected appearance of a novel complex of calcium, phosphate, fetuin, and MGP in serum following etidronate injection. The structure and properties of this complex have direct relevance to an understanding of how MGP normally inhibits calcification in vivo.

Experimental Procedures

Materials

Simonsen albino male rats (Sprague-Dawley derived) were purchased from Simonsen labs (Gilroy, Calif.). Etidronate was a gift from Proctor and Gamble (Cincinnati, Ohio). Sephacryl S-300 HR gel filtration media was purchased from Pharmacia (Piscataway, N.J.). Ultrafree CL filtration devices were purchased from Millipore Corp. Warfarin was purchased from Sigma (St. Louis, Mo.). Stock solutions of sodium warfarin were prepared at 50 mg per ml in 0.15M NaCl and stored in sterile foil wrapped containers at 4° C. MGP was purified from rat bone as described (Hale et al. (1991) *J. Biol. Chem.* 266: 21145–21149). All other reagents used were reagent grade or better.

Maintenance of Animals

Figure 9A:
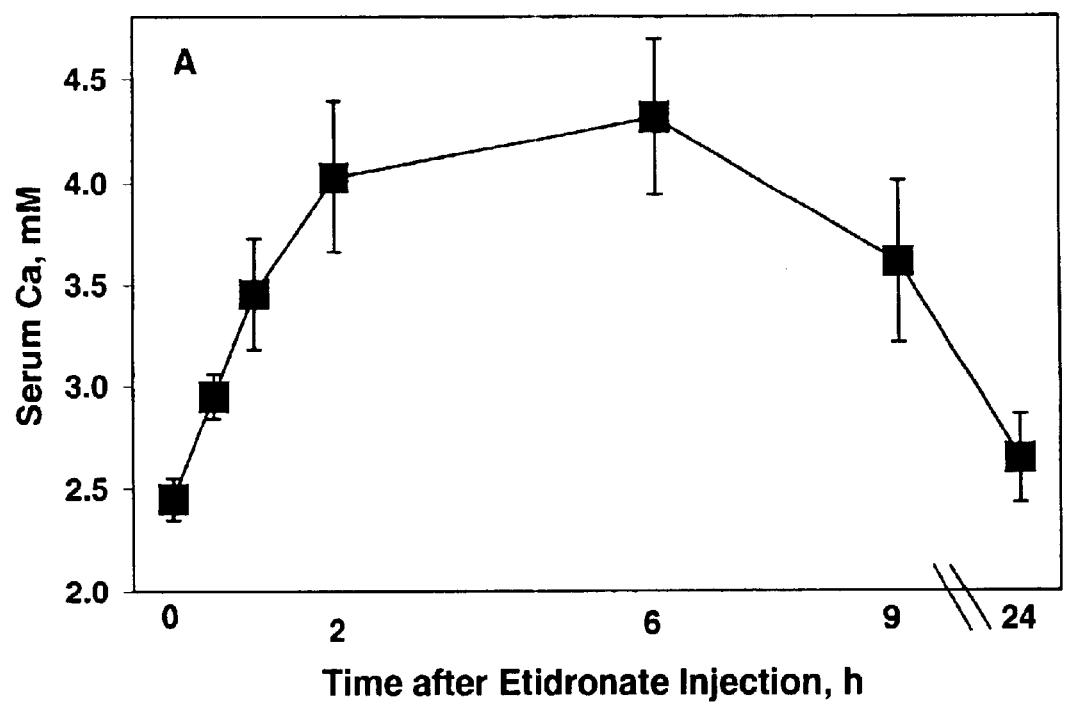
FIGS. 9A, 9B, and 9C show the effect of an 8 mg/100 g etidronate dose on serum levels of calcium, phosphate, and matrix Gla protein. Five forty-day-old male Sprague Dawley rats were given subcutaneous injections of etidronate at a dose of 8 mg/100 g body weight at t=0. Blood was removed from each animal at the indicated times and analyzed to determine the levels of calcium, phosphate, and MGP (see Example 3). Each data point is the average of the individually determined levels in the 5 experimental animals and the error bars denote the standard deviations.
Figure 9B:
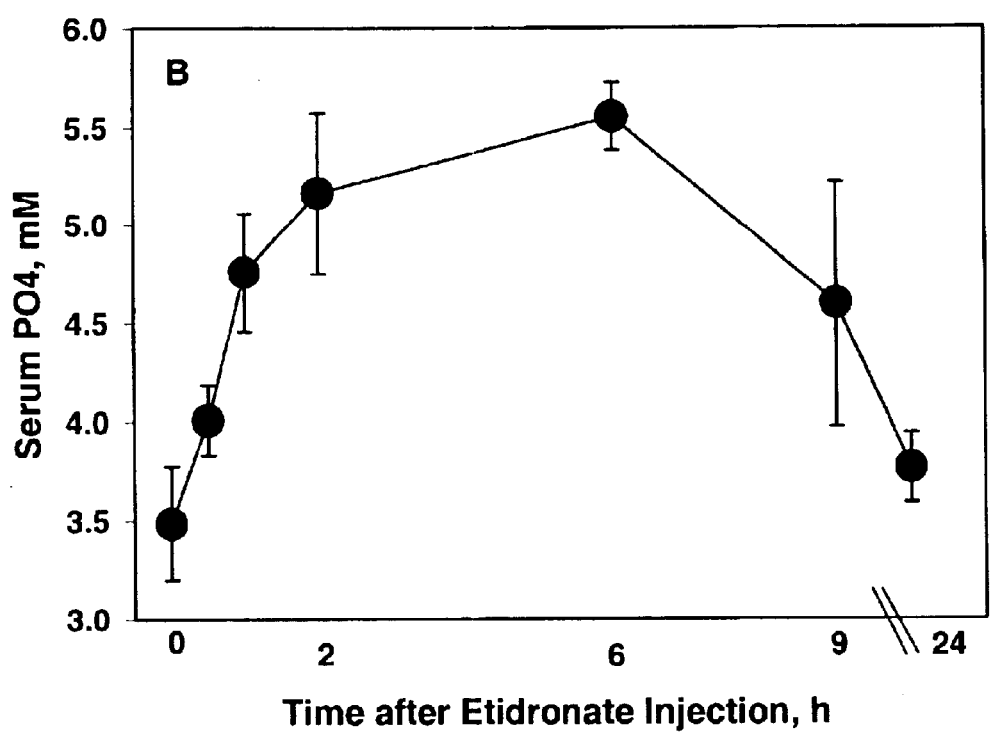
Figure 9C:
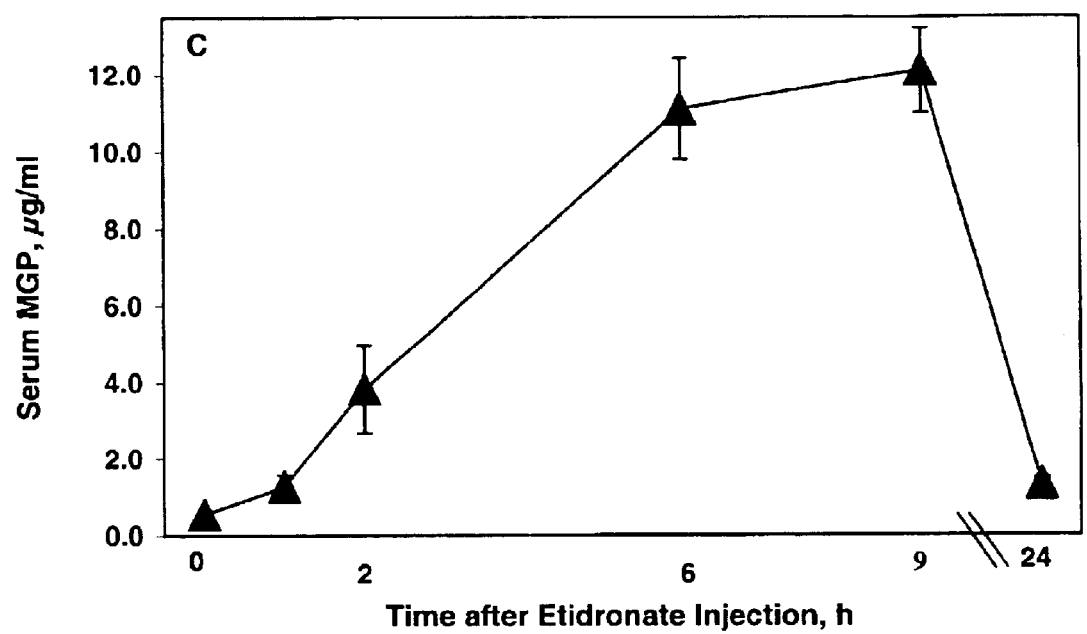

Rats were fed rodent diet 5001 (Purina Mills Inc., St. Louis, Mo.), a diet that is 0.67% phosphorus and 0.95% calcium by weight. Etidronate was dissolved with 0.15 M NaCl, titrated to pH 7.4 with dilute NaOH, and administered subcutaneously to forty-day-old male rats. Control animals received injections of 0.15 M NaCl only. In the initial time course experiment (FIG. 9), 5 forty-day-old male rats were injected with 8 mg etidronate per 100 g body weight at t=0. At the times indicated in FIG. 1, each rat was anesthetized with metofane and a 400 $\mu$l sample of blood was withdrawn from the jugular vein. Blood samples were allowed to clot for 15 min at room temperature and serum was obtained after centrifugation in a clinical centrifuge and then frozen rapidly on dry ice and stored at $-70°$ C. until later analysis. The same procedure was followed for the second time course experiment (FIG. 10), with the difference that the etidronate dose was increased to 32 mg per 100 g body weight.

To determine the effect of warfarin on the generation of the serum protein-mineral complex, 4 rats received subcutaneous injections of 15.4 mg warfarin/100 g body weight and 4 rats received injections of saline vehicle. Two hours later, all rats were injected with etidronate at a dose of 8 mg/100 g (t=0), and 400 $\mu$l of blood were removed from each animal at the indicated times for biochemical analyses. Control experiments were also carried out in which 4 animals received warfarin but not etidronate, and four animals were injected with saline vehicle only. In neither control group could we detect a significant change in serum levels of calcium, phosphate, or MGP at any time point.

In order to examine the possible linkage between the generation of the serum mineral complex and inhibition of bone mineralization, twelve 100 g rats were injected with 4 mg of etidronate at t=0, and were then divided into 2 groups of 6 rats each. 0.5 ml blood samples were obtained from the group 1 rats at t=0, 2, 6, and 12 h, and the rats were exsanguinated at t=24 h. The group 2 rats were injected with a second dose of etidronate at t=24 h, and 0.5 ml blood samples were obtained at t=24, 26, 30, and 36 h. These rats were exsanguinated at t=48 h. Serum was obtained at each time point and stored at $-20°$ C. until later analysis. Tibias from the rats killed at 48 h, as well as from age-matched controls, were removed, cleaned of adhering tissue, and fixed in 70% ethanol. Tibia samples were embedded in plastic and cut into sections of 500 microns by Pathology Associates International (Frederickberg, Md.). The resulting sections were microradiographed using a Hewlett-Packard Model 4380N Faxitron Xray machine. All animal experiments were approved by the UCSD animal subjects committee.

Biochemical Characterization of the Complex Between Calcium, Phosphate, Fetuin, and MGP The serum mineral complex was characterized by filtration using Ultrafree CL filtration devices with a 300 kDa molecular weight cut off membrane. In a typical experiment, blood was obtained from 2 control rats and from 2 rats 6 h after a dose of 8 mg etidronate/100 g, and each blood sample was immediately placed into a 2.5 ml gold top vacutainer tube (SST gel and clot activator tube, Becton Dickinson). Thirty minutes later 1 ml aliquots of the serum were removed, placed into the filtration device, and centrifuged for 80 min at 2500×g to force the sample through the membrane. The filtrate and retentate were then analyzed to determine calcium, phosphate, and volume. The typical filtrate volume recovered was 0.70 ml and the typical retentate volume recovered was 0.26 ml.

The effect of centrifugation on the serum mineral complex was investigated in serum samples obtained 6 h after administration of etidronate at doses of 8 mg/100 g and 32 mg/100 g body weight. At the lower dose, no significant amount of calcium, phosphate, or MGP was sedimented after centrifugation for 30 min at 16,000×g. At the higher dose, a well-defined translucent pellet was obtained after centrifugation for 30 min at 16,000×g. This pellet was dissolved in 1 ml of 50 mM HCl and analyzed for calcium, phosphate, and MGP.

The serum mineral complex was characterized by gel filtration using 25 ml columns of Sephacryl S-300 HR which were prepared in disposable plastic pipets and were equilibrated with 20 mM HEPES pH 7.4, 0.15 M NaCl and 10 mM $CaCl_2$ at room temperature. Serum was obtained from rats 6 h after administration of etidronate at a dose of 8 mg/100 g, and 1 ml aliquots were immediately applied to the Sephacryl column. Fractions of 0.5 ml were then collected and analyzed to determine the level of phosphate and MGP (see below).

Analytical Methods

For determination of MGP and bone Gla protein (BGP), aliquots of fractions and serum samples were diluted into diluent and assayed in triplicate using radioimmunoassay procedures previously described (Cancela and Price (1992) *Endocrinology* 130: 102–108; Rice et al. (1994) *J. Bone Min. Res.* 9: 567–576). Calcium levels in serum and other samples were determined colorimetrically using cresolphthalein complexone (Sigma) and phosphate levels in serum, effluent fractions, and other samples were determined calorimetrically as described (Chen et al. (1956) *Anal. Chem.* 28(11): 1756–1758). For determination of ionic calcium, freshly obtained blood samples were immediately placed into a 2.5 ml gold top vacutainer tube to avoid out gassing of $CO_2$ and the associated shift in pH. Clotted blood was centrifuged for 10 min in a clinical centrifuge, and serum was analyzed for ionic calcium at the UCSD Medical Center Chemistry Laboratory. Electrophoresis was carried out using 4 to 20% polyacrylamide gels (Novex, Inc., San Diego, Calif.) run in Tris-glycine buffer containing SDS. Protein sequencing was carried out on bands transferred to PVDF membranes using a Procise 494 Sequencer (ABI division, PE Biosystems, Foster City, Calif.).

Results

Effect of High Etidronate Doses on Serum Levels of Phosphate, Total Calcium, Ionic Calcium, and Matrix Gla Protein The initial study was carried out to determine the effect of etidronate on serum MGP levels using a subcutaneous dose that, in a previous study, was found to elicit an elevation in serum levels of bone Gla protein (BGP) (Price et al. (1981) in *The Chemistry and Biology of Mineralized Connective Tissues.* (Veis, A., ed) Vol. 1, pp. 327–335., Elsevier, North Holland), a vitamin K-dependent bone protein related in sequence to MGP. Serum was obtained from rats at different times after the subcutaneous administration of etidronate at a dose of 8 mg/100 g body weight, and each serum sample was then analyzed for levels of MGP and BGP by radioimmunoassay. In agreement with the earlier study (Id.), serum levels of BGP were elevated by a maximum of 3 fold and the peak serum BGP level was observed at 1 h (data not shown). In marked contrast, serum MGP levels were increased by 25 fold rather than 3 fold, and the peak level of MGP was observed at 6 h rather than at 1 h.

Because MGP is known to inhibit the calcification of arteries and other soft tissues (Price et al. (1998) *Arterioscler. Thromb. Vasc. Biol.* 18: 1400–1407; Price et al. (2000) *Arterioscler. Thromb. Vasc. Biol.* 20: 317–327), we suspected that the dramatic serum MGP response to etidronate could be associated with the appearance of a calcium phosphate mineral complex in serum. We accordingly carried out a second experiment in which we measured serum levels of MGP, calcium, and phosphate at different times following the administration of etidronate. As shown in FIG. 1, serum calcium and phosphate levels increased rapidly following subcutaneous injection of etidronate, and, by 6 h, the levels of total calcium and phosphate were 76% and 59% above control levels respectively. Serum levels of MGP increased more slowly than total serum calcium and phosphate levels, with half of maximal levels at 3 h for MGP compared with 1 h for calcium and phosphate.

Figure 10:
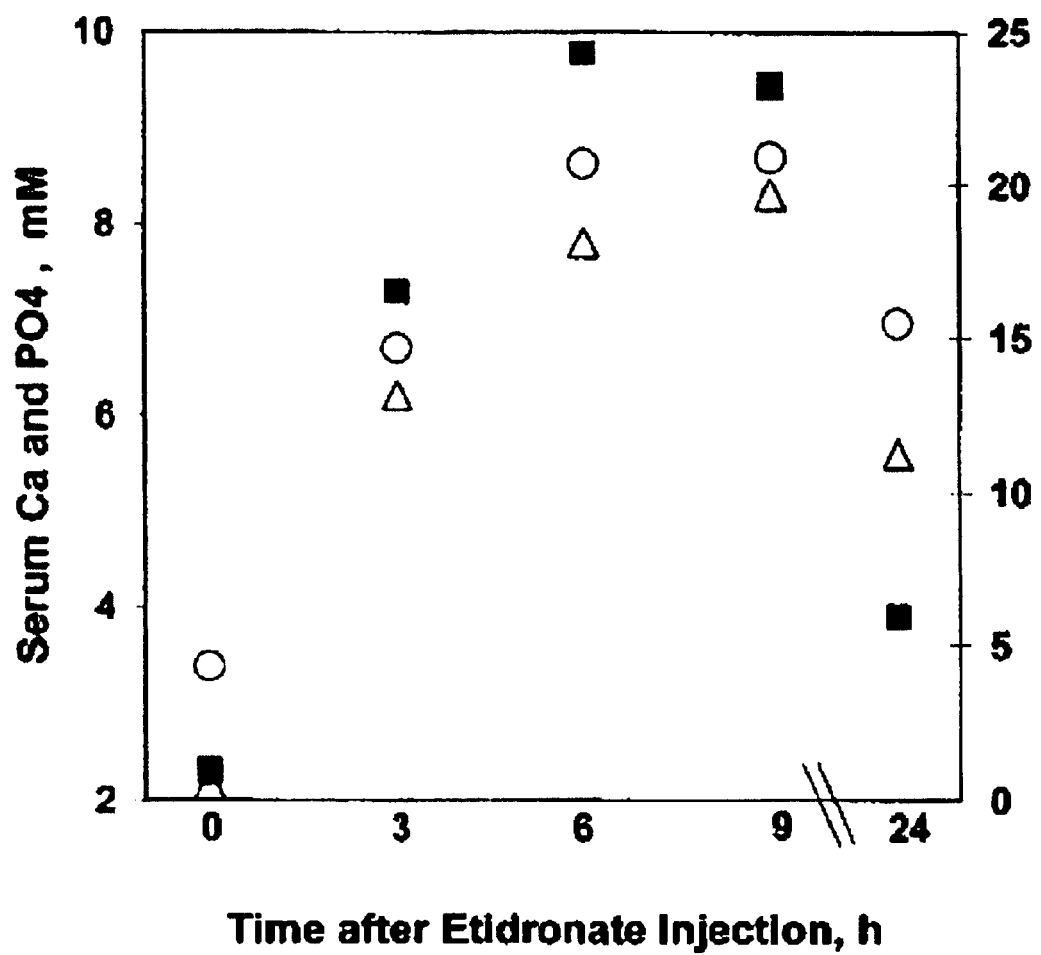
FIG. 10 shows the effect of a 32 mg/100 g etidronate dose on serum levels of calcium, phosphate, and matrix Gla protein. Three forty-day-old male Sprague Dawley rats were given subcutaneous injections of etidronate at a dose of 32 mg/100 g body weight at t=0. Blood was removed from each animal at the indicated times and analyzed to determine the levels of calcium, phosphate, and MGP (see Experimental Procedures). Each data point is the average of the individually determined levels in the 3 experimental animals. ■, serum calcium, mM; ○, serum phosphate, mM; Δ, serum MGP, μg/ml.

To determine whether the rise in total calcium following etidronate administration is due to an increase in ionic calcium or to an increase in a calcium complex, in a follow up experiment 4 rats were exsanguinated at t=0, 1, 2, and 6 h after injection of 8 mg etidronate/100 g body weight and the level of ionic and total calcium were measured in each serum sample. Ionic calcium values were 1.46±0.03 mM at t=0 h, 1.47±0.04 mM at 1 h, 1.51±0.04 mM at 2 h, and 1.46±0.03 mM at 6 h, while total calcium levels were 2.45±0.11 mM at t=0 h, 3.45±0.34 mM at 1 h, 4.05±0.44 mM at 2 h, and 4.41±0.43 mM at 6 h. The failure etidronate to cause a rise in ionic calcium levels indicates that the increase observed in total calcium levels must be due to the appearance of a non-ionic form of calcium in serum. Because there is a parallel increase in serum phosphate and total calcium levels following etidronate injection (FIG. 9), it seemed likely that this non-ionic form of serum calcium is a complex of calcium and phosphate As seen in FIG. 10, a four fold higher subcutaneous dose of etidronate produced a greater elevation in serum total calcium, phosphate, and MGP. The time course of the response to the 32 mg/100 g etidronate dose was similar to the response seen with the 8 mg/100 g dose over the first 9 h, with a maximal level in serum total calcium, phosphate, and MGP at 6 to 9 h following treatment with 32 mg/100 g etidronate. Serum levels of total calcium, phosphate, and MGP remained substantially elevated at 24 h after the 32 mg/100 g dose of etidronate, however, suggesting that the higher dose prolongs the serum response. In spite of the 4.5 fold increase in serum total calcium at 6 h after treatment with 32 mg/100 g of etidronate there was no increase in the level of serum ionized calcium at 6 h, which further supports the conclusion that the increase in serum calcium is due to the appearance of a calcium complex. A two fold lower etidronate dose of 4 mg/100 g body weight produced a smaller increase in serum calcium, phosphate, and MGP at 6 h than the 8 mg/100 g dose (data not shown). In contrast, the amino bisphosphonate alendronate had no effect on serum calcium, phosphate, and MGP levels measured at 1, 2, 6, 12 and 24 h after administration of a 4 mg/100 g dose of the drug (data not shown).

Filtration Evidence for a High Molecular Weight Complex of Calcium, Phosphate, and MGP in the Serum of Etidronate-treated Rats In order to further characterize the calcium complex which is responsible for the rise in total calcium but not ionic calcium following etidronate injection, serum from etidronate treated and control rats was filtered through 300 kDa molecular weight cut off membranes using an Ultrafree CL filtration device, and the filtrate and retentate fractions were separately analyzed for calcium, phosphate, and MGP. As can be seen in Table I, the increase in total serum calcium, phosphate, and MGP levels produced by the 8 mg /100 g dose of etidronate proved to be due to an increase in the levels of calcium, phosphate, and MGP in the high molecular weight retentate fraction, and the filtrate levels of calcium and phosphate were the same for control and etidronate treated rats. This result indicates that the increases in total calcium, phosphate, and MGP seen in the serum of rats treated with etidronate is probably due to the appearance of a high molecular weight serum complex of calcium, phosphate, and MGP.

TABLE I

Effect of filtration through a 300 kDa membrane on serum calcium and phosphate. Serum was obtained from 2 forty-day-old male rats 6 h after subcutanerous injection with etidronate at a dose of 8 mg/100 g body weight, and from 2 age-matched control rats. One ml aliquots of the 4 serum samples were filtered through a 300 kDa molecular weight cut off membrane using a Ultrafree CL filtration device, and the levels of calcium, phosphate, and volume were measured for the filtrate and the retentate fractions (see Experimental Procedures for details). The data show the number of $\mu$mol calcium and phosphate in 1 ml serum prior to filtration, and in the 0.7 ml filtrate and 0.26 ml retentate volumes recovered after filtration. The data are the average of the values for the 2 control rats and the 2 etifronate-treated rats.

|  | Calcium, $\mu$mol | | Phosphate, $\mu$mol | | MGP, ng | |
|---|---|---|---|---|---|---|
|  | Control | Etidronate | Control | Etidronate | Control | Etidronate |
| Initial Serum | 2.68 | 4.30 | 3.56 | 5.10 | 454 | 14,800 |
| Filtrate | 1.20 | 1.18 | 2.72 | 2.98 | 42 | 291 |
| Retentate | 1.28 | 2.72 | 0.98 | 1.84 | 284 | 11,630 |

To determine the stability of the putative serum mineral complex, another 1 ml aliquot of serum from the etidronate treated rats (see Table I legend) was placed into a sealed tube, incubated at room temperature for 1 day, and then filtered through a 300 kDa molecular weight cut off membrane using the method described in Table I. The levels of calcium, phosphate, and MGP in the resulting retentate and filtrate fractions were comparable to the values found for serum filtered immediately after serum was obtained (shown in Table I), with retentate calcium levels of 2.83 $\mu$mol, phosphate of 2.02 $\mu$mol, and MGP of 12,127 ng; and with filtrate calcium levels of 1.21 $\mu$mol, phosphate of 2.79 $\mu$mol, and MGP of 320 ng. This result shows that the putative calcium phosphate mineral phase found in the serum of an etidronate treated rat does not grow at the expense of free calcium and phosphate levels in serum. In another stability test, a 1 ml aliquot of serum from the etidronate treated rat was frozen on dry ice and thawed 5 times and then subjected to filtration. Retentate and filtrate levels of calcium, phosphate, and MGP levels were again comparable with the values shown in Table I, which demonstrates that the amount of the putative serum mineral complex is not affected by repetitive freezing of the serum sample.

Figure 11:
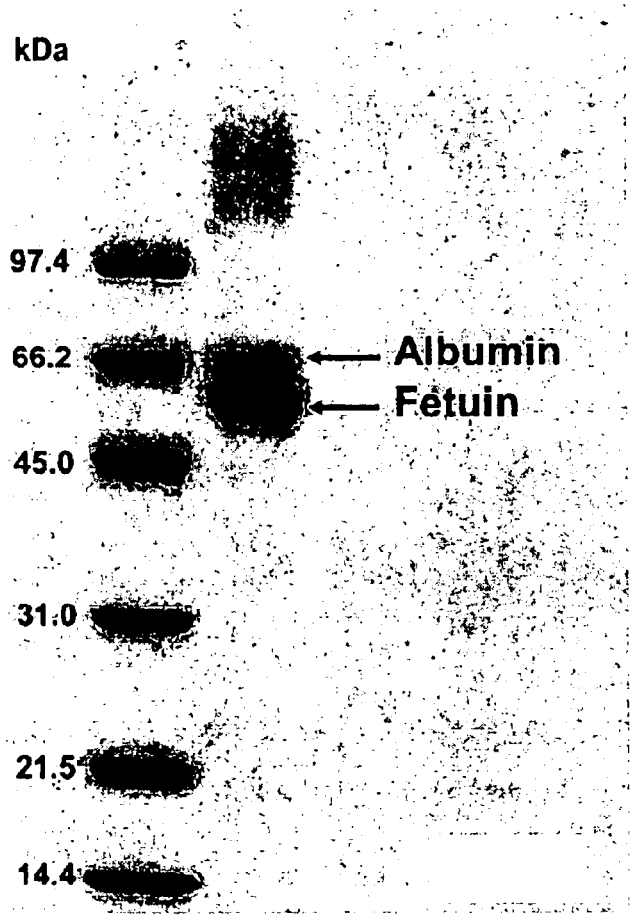
FIG. 11 shows an SDS Polyacrylamide gel electrophoresis of the proteins associated with the serum mineral complex. A 7 μg aliquot of the dissolved pellet from the centrifugation experiment described in Table II was dried, dissolved in loading buffer, and then electrophoresed on a 4 to 20% polyacrylamide gel and stained with Coomassie Brilliant Blue (left lane). Bio-Rad low molecular weight markers are in the left lane.

Centrifugational Evidence for a Complex of Calcium, Phosphate, Fetuin, and MGP in the Serum of Etidronate-treated Rats We next examined the possible sedimentation of the serum calcium phosphate complex during centrifugation, a property that might be anticipated for the complex based on the fact that calcium phosphate mineral phases typically have densities about 3 fold greater than serum. As shown in Table II, centrifugation of serum from rats treated with the 32 mg dose of etidronate resulted in a pellet containing calcium, phosphate, and MGP. When the pellet was dissolved in acid and analyzed by SDS-PAGE, a major band was found at 59 kDa which accounted for at least 80% of the Coomassie staining (FIG. 11). When this component was electrophoretically transferred to PVDF and subjected to N-terminal protein sequencing, one sequence was obtained, A-P-Q-G-A-G-L-G-F-R-(SEQ ID NO:1), which matches the N-terminal sequence of rat fetuin (Ohnishi et cii. (1993) J. Bone and Mineral Res. 8: 367–377). The other major band in the gel had an apparent molecular weight of 66 kDa and accounted for about 10% of the total Coomassie staining; this band was identified as rat serum albumin by N-terminal sequence analysis. Based on the recovery of fetuin in the pellet, we estimate the weight ratio of fetuin to mineral phosphate in the pellet to be 3.4 mg/mg. Since the supernatant level of calcium and phosphate remained above the level in control serum (Table II), it is likely that centnfugation did not sediment all of the calcium complex in these experiments.

TABLE II

Effect of Centrifugation on Serum Calcium and Phosphate. Serum was obtained from 3 forty-day-old male rats 6 h after subcutaneous injection with etidronate at a dose of 32 mg/100 gm body weight and was pooled. A one ml aliquot of pooled serum was immediately centrifuged at 16,000 × g for 30 min at room temperature. The supernatant was removed and the pellet was rinsed once with 1 ml of 0.15 M NaCl and then dissolved with 1 ml of 50 mM HCl. The data show the number of $\mu$mol calcium and phosphate in 1 ml serum prior to centrifugation, and in the supernatant and dissolved pellet.

|  | Calcium, $\mu$mol | Phosphate, $\mu$mol | MGP, ng |
|---|---|---|---|
| Initial Serum | 9.64 | 7.49 | 16,200 |
| Supernatant | 6.88 | 5.84 | 800 |
| Dissolved Pellet | 3.27 | 1.68 | 14,400 |

Because it is conceivable that the nature of the protein mineral complex could be affected by the blood coagulation needed for serum collection, the filtration and centrifugation experiments described above were repeated using heparinized plasma samples. In the filtration experiment, filtrate and retentate levels of calcium, phosphate, and MGP in plasma from control rats and from the etidronate treated rats were each within 5% of the values reported in Table I. In the centrifugation experiment, the amount of calcium, phosphate, and MGP in the supernatant and pellet fractions obtained by centrifuging plasma from control and etidronate treated rats were each within 7% of the values reported in Table II, and the SDS gel of the proteins in the dissolved pellet was indistinguishable from that shown in FIG. 11. These experiments show that the nature of the mineral complex does not appear to be affected by the process of blood coagulation.

In experiments using serum obtained 6 h after administration of 8 mg etidronate/100 g, we were unable to demonstrate the sedimentation of calcium, phosphate, or MGP after 30 minutes centrifugation at 16,000×g. This result indicates that the putative complex of a calcium phosphate mineral phase and protein found following the 8 mg/100 g etidronate dose has different sedimentation properties than the complex found following the 32 mg /100 g dose.

Gel Filtration Evidence for a High Molecular Weight Complex of Calcium, Phosphate, Fetuin, and MGP in the Serum of Etidronate-treated Rats In order to further characterize the calcium phosphate complex found in the serum of rats treated with the 8 mg/100 g dose of etidronate, we sought to partially purify this complex by gel filtration over a column of Sephacryl S300 using 10 mM calcium in the buffer in order to stabilize the putative complex. As seen in FIG. 4, there is a peak of MGP and phosphate in the excluded volume position of the chromatogram of serum from the etidronate treated rat which is not found in the chromatogram of serum from an untreated rat. The MGP antigen recovered in this excluded volume peak accounts for the amount of MGP antigen in the serum sample applied to the column, and there was no detectable MGP antigen in the elution position of the 10 kDa MGP monomer, which is about fraction 40. In contrast, no bone Gla protein (BGP) antigen could be detected in the high molecular weight position in the chromatogram, and all BGP antigen was recovered in a single peak in the fraction 45 position expected for the 6 kDa BGP monomer (data not shown). This result indicates that the association of MGP with the serum mineral complex is highly specific, since it is well established that BGP binds strongly to hydroxyapatite in vitro and in serum (Price et al. (1981) in *The Chemistry and Biology of Mineralized Connective Tissues*. (Veis, A., ed) Vol. 1, pp. 327–335., Elsevier, North Holland; Price et al. (1979) in *Vitamin K Metabolism and Vitamin K-dependent Proteins* (Suttie, J. W., ed), pp. 219–226, University Park Press).

To evaluate the possible presence of other proteins associated with the serum mineral complex, the Sephacryl S300 fractions corresponding to the high molecular weight phosphate peak from an etidronate treated rat (FIG. 12 upper) and the corresponding fractions from a normal rat (FIG. 12 lower) were separately combined with EDTA and fractionated by SDS-PAGE. As shown in FIG. 13, there is a prominent coomassie stained protein band in the lanes for the etidronate treated animal which is not seen in the lanes for the control animal, a band with an apparent molecular weight of about 59 kDa. In order to identify this protein constituent, fraction 23 from the high molecular weight phosphate peak in the chromatogram of etidronate treated rat (FIG. 12 upper) was fractionated by SDS-PAGE followed by electrophoretic transfer to PVDF. N-terminal protein sequencing of this 59 kDa band revealed that its sequence matched the N-terminal sequence of rat fetuin (Ohnishi et al. (1993) *J. Bone and Mineral Res*. 8: 367–377). Comparison of the SDS-PAGE for fraction 23 from the Sephacryl S300 gel filtration of etidronate and control rat serum using a more sensitive colloidal coomassie stain revealed the presence of a band in the 14 kDa position expected for purified MGP in the lanes from the etidronate treated rat but not in the lanes from the control rat (figure not shown). No other band could be detected in the SDS-PAGE of fraction 23 from the etidronate treated rat chromatogram that was not also found at comparable levels in fraction 23 from the control rat chromatogram.

Figure 12A:
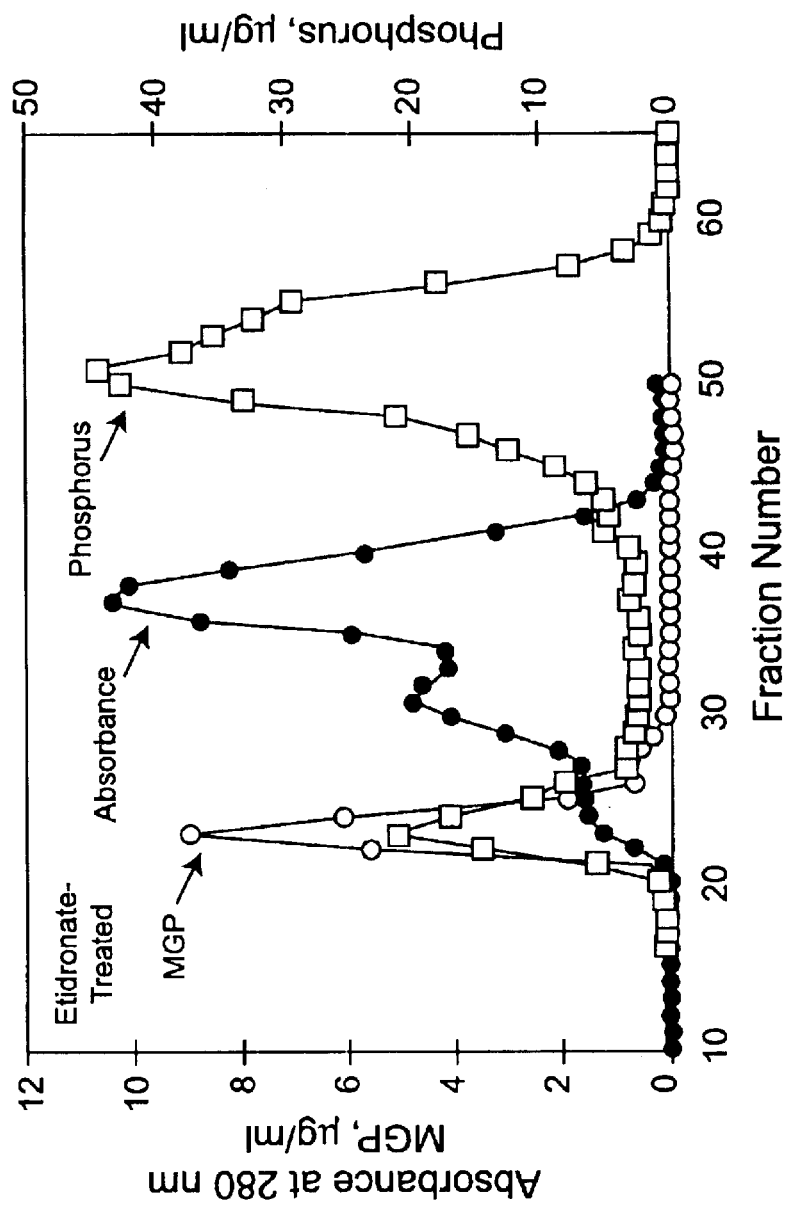
FIGS. 12A and 12B show a Sephacryl S-300 HR filtration of serum from etidronate-treated and control rats. Forty-day-old male rats received a single subcutaneous dose of 8 mg etidronate per 100 g body weight or of vehicle alone and blood was collected 9 h later. One ml serum samples were then immediately applied to a 25 ml column of Sephacryl S-300 HR equilibrated with 20 mM HEPES pH 7.4, 0.15 M NaCl, and 10 mM $CaCl_2$ Temperature, 22°; fraction size, approximately 0.5 ml. ●—●, Absorbance at 280 nm; ○—○, μg/ml MGP as determined by radioimmunoassay;—μg/ml phosphorus.
Figure 12B:
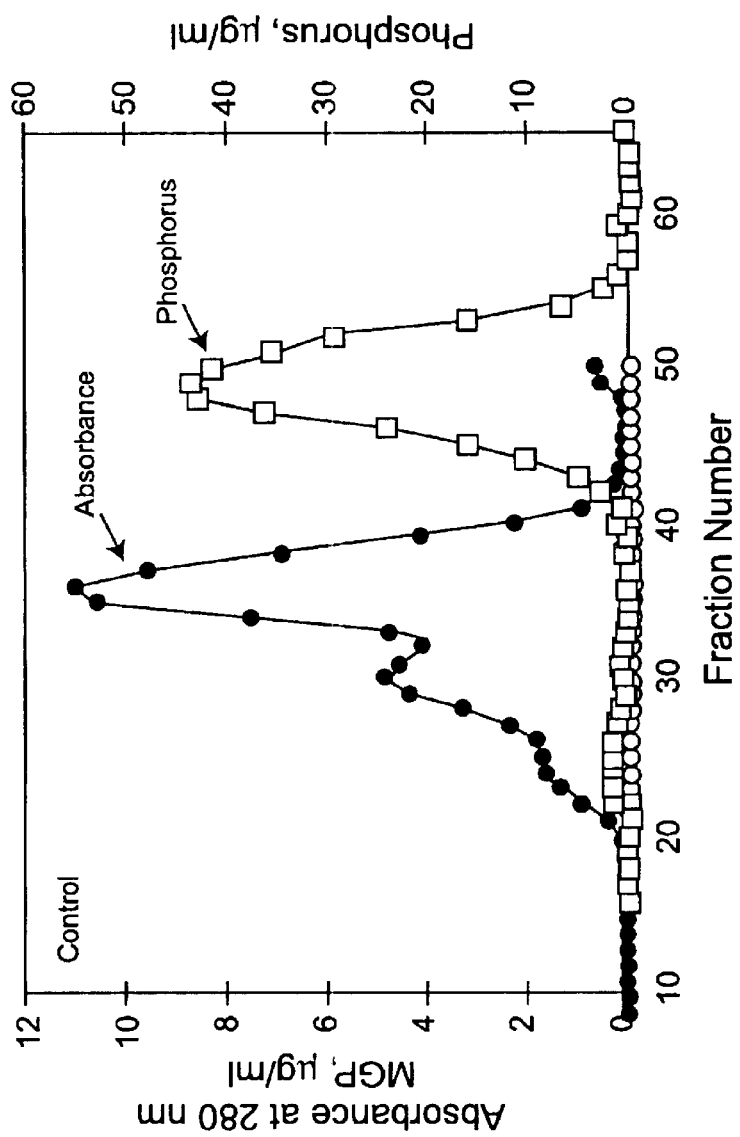
Figure 13:
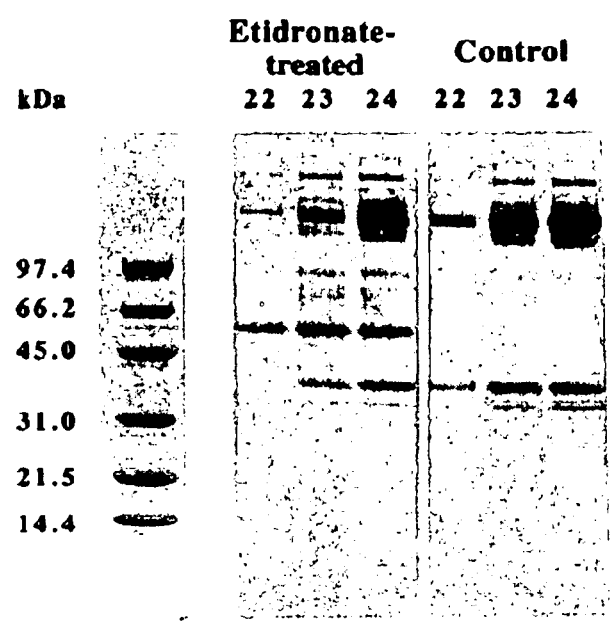
FIG. 13 show the results of electrophoresis of the high molecular weight fractions from the Sephacryl S300 fractionation of serum from etidronate-treated and control rats. Ten μl of fractions 22, 23, and 24 from the chromatograms shown in FIG. 12 upper and lower were each first mixed with 10 μl of 2 X loading buffer containing 60 mM EDTA and then electrophoresed on a 4 to 20% polyacrylamide gel and stained with Coomassie Brilliant Blue.

To estimate the amount of fetuin in the high molecular weight phosphate peak fractions, we performed two repeat SDS-PAGE analyses of fractions 22–24 of FIG. 12 upper together with lanes containing known amounts of pure fetuin. Quantitative analysis of the amount of coomassie staining in these fetuin bands using a densitometer yielded an estimate of 630 µg fetuin in fractions 22–24. The phosphate content of these fractions is 83 µg phosphate, and the weight ratio of fetuin to phosphate is 7.6 mg/mg. The total MGP content of fractions 22–24 is 11 µg (FIG. 12), and the calculated molar ratio of MGP to fetuin in these fractions is 1:8.

Evidence that Editronate Generates the Serum Mineral Complex by Inhibiting Bone Mineralization Previous studies have shown that the doses of etidronate used here to cause the appearance of the complex of calcium, phosphate, fetuin, and MGP in serum also cause the inhibition of the normal calcification of bone and cartilage, resulting in the formation of unmineralized osteoid in bone and of unmineralized cartilage in the growth plate (Schenk et al. (1973) *Calc. Tiss. Res*. 11: 196–214). When 100 g rats are given a dose of 4 mg etidronate per day, this inhibition of mineralization is discontinuous and results in the appearance of alternating bands of calcification and no calcification in the proximal tibia. In the present studies we sought to determine whether the timing of the appearance of the calcium-phosphate-fetuin-MGP complex in serum correlates with the inhibition of growth plate cartilage mineralization. As seen in FIG. 6, microradiographs of the proximal tibial metaphysis of 100 g rats given 4 mg of etidronate at t=0 and 24 h and killed at 48 h revealed alternating bands of calcification and no calcification which are identical to those reported in the earlier study (see FIG. 6 in Schenk et al. (1973) *Calc. Tiss. Res*. 11: 196–214), with inhibition of calcification from approximately 0 to 12 h, calcification from 12 to 24, inhibition of calcification from 24 to 36 h, and calcification from 36 to 48 h. As shown in FIG. 7, the 0 to 12 h and 24 to 36 h intervals during which calcification was inhibited are the intervals during which serum levels of calcium, phosphate, and MGP became elevated, while the 12 to 24 h and 36 to 48 h intervals during which cartilage calcification returned to normal are the intervals in which serum levels of calcium, phosphate, and MGP also returned to normal values. These results show that the appearance of the serum mineral complex following etidronate injection correlates with the timing of the inhibition of growth plate cartilage mineralization.

Figure 16A:
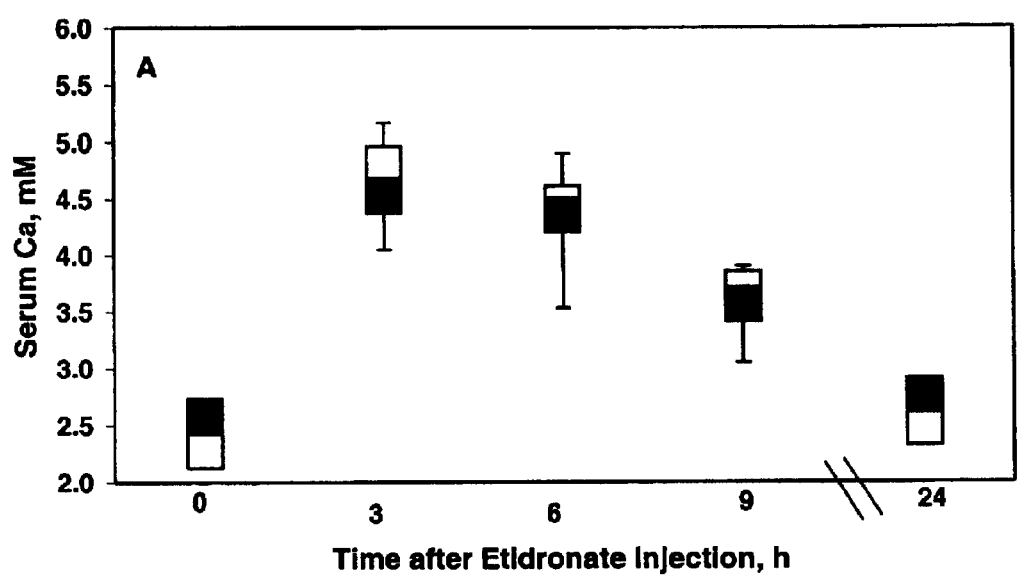
FIGS. 16A, 16B, and 16C show the effect of warfarin on serum levels of calcium, phosphate, and matrix Gla protein in animals treated with a 8 mg/100 g dose of etidronate. Eight forty-day-old male Sprague Dawley rats were given subcutaneous injections of 8 mg etidronate per 100 g at t=0. Four animals also received an injection of 15.4 mg warfarin per 100 g two hours prior to the etidronate injection. Blood was removed from each animal at the indicated times and analyzed to determine the levels of calcium, phosphate, and MGP. Each data point is the average of the individually determined levels in the 4 experimental animals in each treatment group and the error bars denote the standard deviations.
Figure 16B:
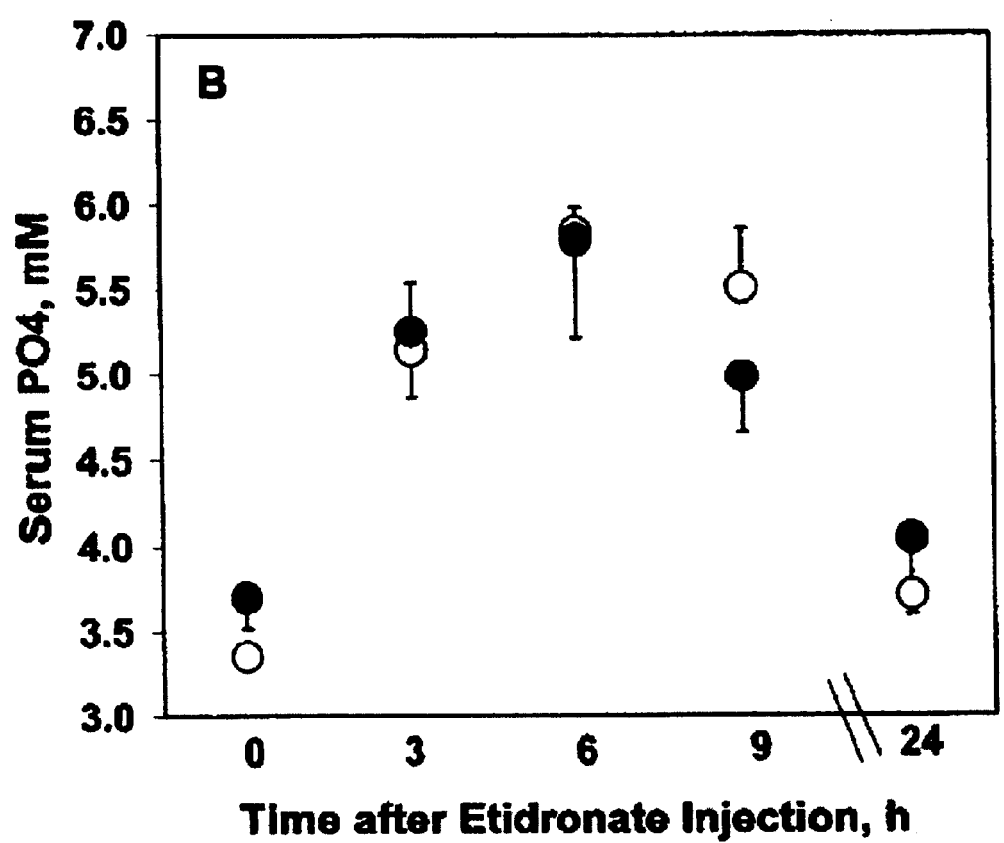
Figure 16C:
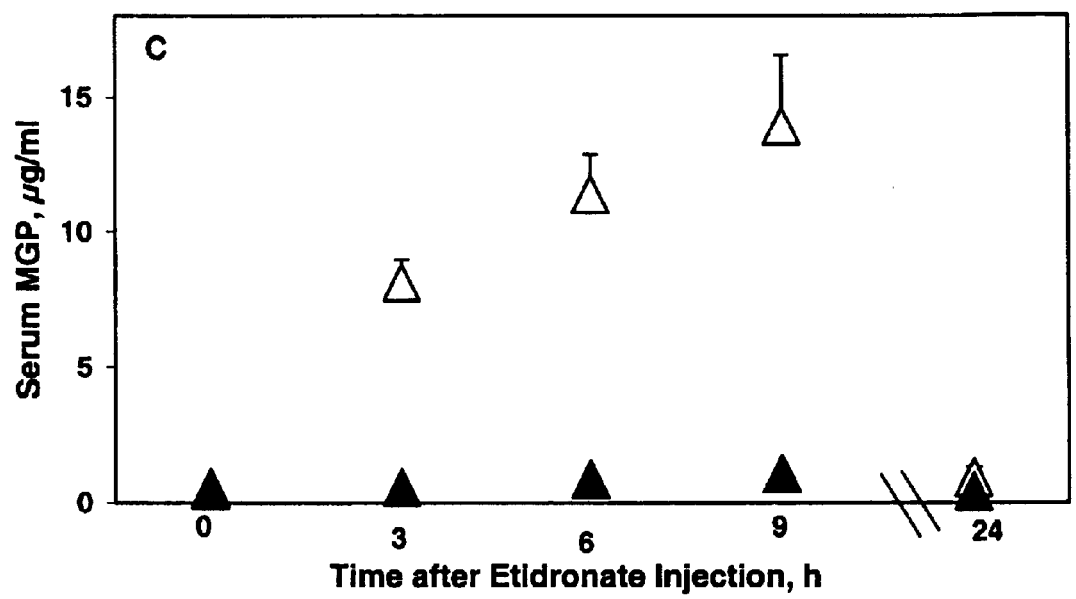

Effect of Warfarin Treatment on the Mineral Complex Found in the Serum of Etidronate-treated Rats We have previously shown that the vitamin K antagonist warfarin inhibits the γ-carboxylation of MGP and thereby inactivates the calcification inhibitory activity of the protein and causes extensive calcification of arteries and heart valves (Price et al. (1998) *Arterioscler. Thromb. Vasc. Biol.* 18: 1400–1407; Price et al. (2000) *Arterioscler. Thromb. Vasc. Biol.* 20: 317–327). To determine whether the γ-carboxylation of MGP is necessary for the accumulation of the protein in the serum complex of calcium, phosphate, and fetuin, rats were injected with warfarin 2 h prior to the administration of etidronate in order to ensure that all MGP synthesized from the time of etidronate administration is non-γ-carboxylated. Blood samples were then obtained at suitable times following etidronate injection and analyzed to determine serum levels of MGP, calcium, and phosphate. As shown in FIG. 16C, warfarin blocked the increase in serum MGP following etidronate administration but did not affect the time course of the elevation in serum calcium and phosphate (FIGS. 16A and 16B). Since warfarin treatment had no effect on serum levels of MGP in animals which did not receive etidronate, warfarin does not inhibit the synthesis of MGP per se, only the accumulation of MGP in serum following etidronate treatment. To further examine the effects of warfarin on the etidronate response, serum was obtained at 6 h following etidronate treatment from rats that were treated concurrently with warfarin. Analysis by Sephacryl S300 chromatography revealed phosphate levels in the high molecular weight, excluded volume position that were comparable to phosphate levels in vitamin K-replete, etidronate treated rats, and MGP levels in the high molecular weight position which were only 5% of the level seen in vitamin K-replete, etidronate treated rats (chromatogram not shown). These results demonstrate that the γ-carboxylation of MGP is critical for its incorporation into the serum mineral complex and also show that the MGP which accumulates in this complex must arise from new MGP synthesis. Because serum calcium and phosphate levels are not affected by warfarin treatment, the absence of MGP in the serum mineral complex does not affect the magnitude of the serum mineral response to etidronate or the subsequent clearance of the mineral complex from serum. SDS gel electrophoresis of the high molecular weight phosphate-containing peak from the Sephacryl S300 chromatogram (data not shown) demonstrated the presence of fetuin at the level found in previous experiments (see FIG. 5), which indicates that the incorporation of fetuin into the serum mineral complex is independent of the presence of MGP.

Discussion

The present study is the first to report the presence of a complex of calcium, phosphate, and protein in serum, and the first to isolate this complex and to determine its structure. This protein mineral complex appears in serum shortly after the administration of the bisphosphonate etidronate and, within 6 h of injection with a 32 mg/100 g dose of etidronate, the presence of this complex in serum increases total serum calcium levels by over 4 fold (to 8.8 mM calcium), phosphate levels by 2.5 fold (to 8.6 mM phosphate), and MGP levels by 36 fold (to 18 µg/ml). Since free calcium and phosphate are not elevated by etidronate treatment (see Table I and text), the protein mineral complex cannot be formed in serum in a physicochemical process driven by the enhanced supersaturation of serum with respect to calcium phosphate mineral phases. In fact when enhanced supersaturated conditions are created in serum by a vitamin D treatment that elevates ionic and total serum calcium by 40%, there is no detectable level of the protein mineral complex in serum (personal observations). It is therefore probable that the protein mineral complex is formed outside of the vascular system as a consequence of etidronate treatment, and subsequently travels to blood. This model does not rule out the possibility that changes in the initial mineral complex may occur after its appearance in serum, and the delayed appearance of MGP in the complex indeed suggests that the MGP content of the complex does change after the initial appearance of the complex in blood.

Figure 14:
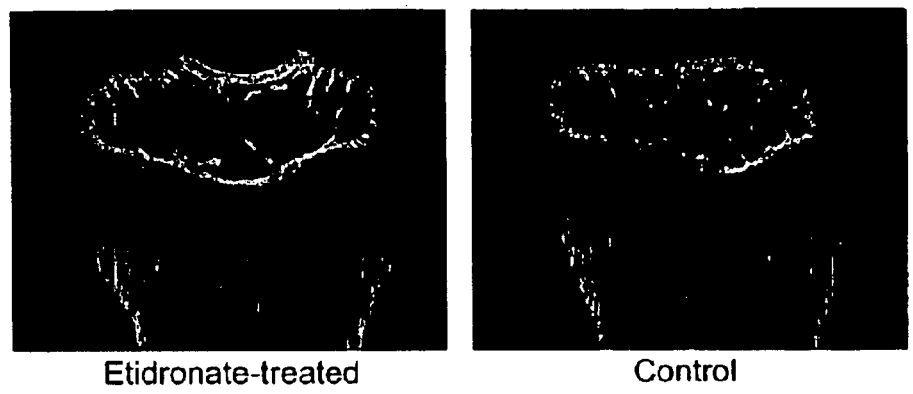
FIG. 14 shows the effect of two 4 mg/100 g doses of etidronate spaced 24 h apart on the microradiograph of the proximal tibia. One hundred gram rats were injected with 4 mg etidronate at t=0 and 24 h, and killed at t=48 h. Tibias were removed from the etidronate-treated rats and from age-matched control rats, fixed in 70% ethanol, embedded in plastic, cut into 500 micron sections, and radiographed. Note the alternating bands of mineralized and non-mineralized matrix in the microradiograph of the proximal tibia from the etidronate-treated rat.
Figure 15:
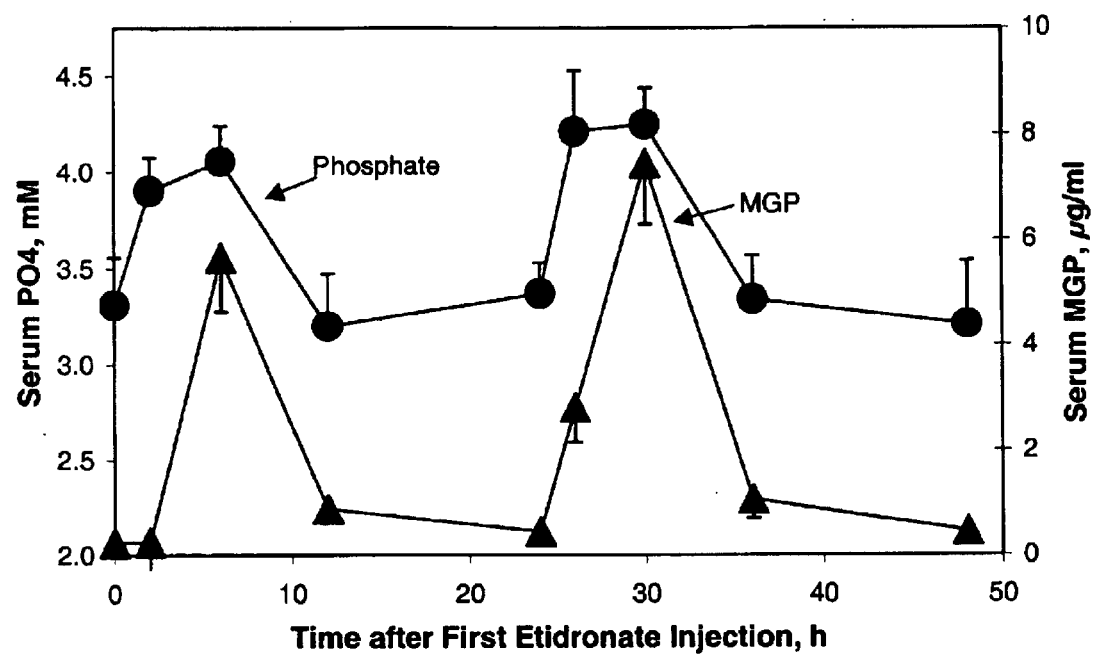
FIG. 15 shows the effect of two 4 mg/100 g doses of etidronate spaced 24 h apart on serum levels of phosphate and matrix Gla protein. Serum was obtained at the indicated times from the rats described in the legend to FIG. 6, and each serum sample was analyzed to determine the levels of phosphate and matrix Gla protein. Each data point is the average of the individually determined levels in 6 experimental animals and the error bars denote the standard deviations. ●, serum phosphate, mM; ▲, serum MGP, μg/ml.

We believe that the serum mineral complex is generated as a consequence of the inhibition of bone mineralization by etidronate rather than as a consequence of the inhibition of bone resorption. Several arguments support this hypothesis: (1.) The appearance of the serum mineral complex and the inhibition of bone mineralization both occur within an hour following etidronate administration (FIG. 9 and (Schenk et al. (1973) *Calc. Tiss. Res.* 11: 196–214)). In contrast, the inhibition of bone resorption by etidronate and other bisphosphonates can only be detected 1 to 2 days following injection of the drug (Antic et al.(1996) *Calcif. Tissue Int.* 58: 443–448). (2.) There is good agreement between the timing of the inhibition of bone mineralization and the appearance of the serum mineral complex following etidronate treatments spaced 24 h apart (FIGS. 14 and 15). (3.) The amino bisphosphonate alendronate does not generate the serum mineral complex even though the dose tested here is over 1000 fold above that needed to inhibit bone resorption in rats of this age. It has been shown previously that this alendronate dose does not inhibit normal bone mineralization (Schenk et al. (1986) *Calcif. Tissue Int.* 38: 342–349).

While the size of the complex cannot be established from these studies, the filtration experiments suggest that the complex must be large enough to be retained by a 300 kDa molecular weight cut off membrane, which supports a size of 300 kDa or larger, and the gel filtration studies indicate that the complex must be large enough to be in the excluded volume position of the Sephacryl S300 column, which is consistent with a size of 250 kDa or larger. The complex may in fact have a range of sizes, since half of the complex formed by the 32 mg/100 g etidronate dose sediments while half of the complex does not (Table II). The size of the complex may also vary with the etidronate dose, since the protein mineral complex found in serum the 8 mg/100 g dose does not sediment upon centrifugation. Fetuin is the major protein component of the serum mineral complex, with an estimated weight ratio of fetuin to mineral of 4.4 for the complex found in serum at the 8 mg/100 g etidronate dose, and an estimated ratio of fetuin to mineral of 1.9 at the 32 mg/100 g dose of etidronate. The MGP content of the serum mineral complex increases with time after etidronate injection, reaching a molar ratio of MGP to fetuin of 1:8. If the average molecular weight of the serum mineral complex were 550,000 daltons, the complex found in serum 6 h following treatment with the 8 mg/100 g dose of etidronate would consist of approximately 8 fetuin molecules, 1 MGP molecule, 790 atoms of calcium, and 580 molecules of phosphate. It should be noted that these calculations are based on the assumption that the only protein constituents of the complex are fetuin and MGP, and that the SDS gel shown in FIG. 3 indicates that higher molecular weight proteins could in fact be present in the complex. Future studies will be needed to identify these components and to establish their possible role in the serum complex.

Since free calcium and phosphate levels remain at control values when serum containing the protein mineral complex is incubated at room temperature for 24 h, a primary function of the protein components of the complex must be to inhibit the growth of the mineral phase component. The protein components must also inhibit the aggregation and precipitation of the mineral phase component, because there is no evidence of the aggregation and precipitation of a mineral phase after 24 h incubation at room temperature. Since the serum complex is cleared from serum within 6 h of attaining its peak value (FIGS. 1 and 7), a secondary function of the protein components may be to target the complex for clearance from blood.

Role of Fetuin in the Serum Complex

The most abundant component of the serum complex is fetuin, not mineral or MGP, and it seems probable that the properties of the complex largely reflect the presence of fetuin in it. It is our hypothesis that fetuin molecules aggregate on the surface of the mineral nuclei and thereby prevent growth of the mineral phase and the generation of additional crystal nuclei. We believe that the most likely role for the protein component of fetuin is to mediate the binding of fetuin to mineral and to associate laterally with other fetuin molecules on the mineral surface to inhibit crystal growth. We further speculate that the 5 oligosaccharide moities of fetuin, which account for 25% of its weight, project away from the mineral and into the surrounding aqueous phase. The functions of oligosaccharides in fetuin would be to lower the density of the mineral complex so that it will not sediment in serum and to prevent aggregation of one complex with another.

Previous studies have demonstrated that fetuin inhibits the sedimentation of calcium from supersaturated solutions of calcium and phosphate after centrifugation for 5 min at 15,000×g (Schinke et al. (1996) *J. Biol. Chem.* 271: 20789–20796). Fetuin in fact accounts for roughly half of the inhibitory activity found in serum. Although the mechanism by which fetuin inhibits calcium precipitation was not identified in these studies, the inhibitory activity was shown to be mediated by acidic amino acids clustered in the D1 cystatin-like domain of fetuin. Our present results are consistent with the putative calcification inhibitor activity of fetuin identified in these earlier studies, and suggest that this action of the protein could be associated with its ability to form stable, soluble complexes with mineral nuclei which inhibit nuclei growth and precipitation.

Fetuin is known to be a major component of serum as well as a major constituent of the extracellular bone matrix (Kazi et al. (1998) *J. Biochem.* 124: 179–186; Triffitt et al. (1976) *Nature* 262: 226–227), and either fetuin pool could be the primary source of the fetuin found in the serum mineral complex. An important objective of future studies will be to determine the origin of fetuin in the serum mineral complex, and to evaluate the possibility that etidronate treatment could directly stimulate the synthesis of fetuin by liver or bone.

Role of MGP in the Serum Mineral Complex

The present studies suggest that MGP accumulates in serum following etidronate injection by virtue of its binding to the serum complex. Since the vitamin K antagonist warfarin completely blocks the accumulation of MGP in the complex, it is clear that the MGP which accumulates in the complex arises from new synthesis, and that accumulation of MGP in the complex requires the vitamin K dependent γ-carboxylation of the protein. We believe that the dramatic increase in the total level of serum MGP following etidronate administration is caused by a reduced rate of MGP clearance from blood rather than by an increased rate of MGP synthesis. Serum proteins the size of the 10 kDa MGP molecule are cleared rapidly by kidney filtration ($t_{1/2}$=5 min), and the 0.5 μg/ml level of MGP found in normal rat serum consequently reflects a dynamic balance between new synthesis and clearance, with 0.25 μg/ml/5 minutes of new MGP synthesis compensating for the amount of MGP lost by kidney filtration. MGP bound to the much larger serum mineral complex would evade this clearance mechanism and so accumulate in serum. This hypothesis accounts for the approximately linear accumulation of MGP in serum over the first 6 h following etidronate injection (FIG. 9) as well as the total increase in serum MGP found at 6 h. (In 6 h the amount of MGP that could accumulate in serum by evading kidney clearance would be the rate of appearance of newly synthesized MGP in serum, 0.25 μg/ml/5 minutes, times 360 minutes, which is 18 μg/ml. This number is in good agreement with the actual level of the protein in serum at this time (FIG. 10)). The alternative hypothesis for the 30 fold increase in serum MGP following etidronate administration is that the presence of the fetuin mineral complex in serum could stimulate a dramatic increase in the rate of MGP synthesis by tissues which contribute MGP to blood. While we cannot rule out this hypothesis entirely, investigations of the level of MGP mRNA in several tissues have failed to reveal a significant increase at 6 h after etidronate treatment (personal observations).

The present studies demonstrate that MGP binds to the fetuin mineral complex with considerable strength and specificity. The gel filtration analysis of the elution position of MGP antigen (FIG. 12 upper) failed to detect the presence of any MGP in the elution position of the MGP monomer, which indicates that the concentration of monomeric serum MGP in equilibrium with MGP bound to the complex must be very low. The binding of MGP to the fetuin mineral complex must also be highly specific, since we could detect no other Coomassie stained proteins associated with the complex other than fetuin and MGP (see FIG. 13). The specificity of this interaction is further supported by the observation that the structurally related vitamin K dependent protein, BGP, fails to accumulate in the complex in spite of its known high affinity for hydroxyapatite (Price et al. (1979) in *Vitamin K Metabolism and Vitamin K-dependent Proteins* (Suttie, J. W., ed), pp. 219–226, University Park Press).

The ability of MGP to bind with great avidity to the mineral complex in spite of the presence of fetuin suggests that MGP could in fact have a greater affinity for mineral than fetuin, and so could be the stronger inhibitor of crystal growth. This possibility is supported by the observation that targeted deletion of the MGP gene in the mouse causes rapid and extensive calcification of the elastic lamellae of arteries beginning at birth (Luo et al. (1997) *Nature* 386: 78–81), while fetuin deficient mice have no evidence of soft tissue calcification except for the specialized case of occasional microcalcifications in a few muscles of some female retired breeder mice (Jahnen-Dechent et al. (997) *J. Biol. Chem.* 272: 31496–31503). Without being bound to a particular theory, we believe the failure of soft tissues to calcify in the fetuin deficient mouse is due in part to the ability of MGP to inhibit calcification, and that the capacity of serum MGP to inhibit calcification is adequate to prevent soft tissue calcification under normal physiological circumstances. One prediction of this hypothesis is that a high capacity stress on the ability to inhibit calcification in serum, such as is imposed by a high dose of etidronate, will cause fetuin deficient mice to experience a massive rate of mineral formation, a mineralization which cannot be retarded by the low capacity inhibitory function of serum MGP. A second prediction of this hypothesis is that warfarin treatment and the fetuin gene deletion should act synergistically to produce more rapid ectopic calcification than is found with either condition alone.

While we have focused here on the ability of fetuin and MGP to prevent the growth of the mineral component of the serum complex, it is important to note that both proteins have other important biological activities. Fetuin binds transforming growth factor-β (TGF-β) and bone morphogenic protein-2 (BMP-2) and blocks the osteogenic activity of these cytokines in cell culture assays (Binkert et al. (1999) *J. Biol. Chem.* 274(40): 28514–28520; Demetriou et al. (1996) *J. Biol. Chem.* 271: 12755–12761). MGP also binds BMP-2 and blocks the activity of BMP-2 on cells in culture (Bostrom et al. (2001) *J. Biol. Chem.* 276(17), 14044–14052). An important goal of future studies will be to determine whether fetuin and MGP retain their ability to block the activity of cytokines when they are part of the serum complex.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining the risk for calcification of arteries and other soft tissues in a mammal, said method comprising:

detecting the level of a fetuin-mineral complex in blood from said mammal, wherein an increased level of the fetuin mineral complex as compared to that found in a control indicates that said mammal is at increased risk for calcification of arteries and other soft tissues.

2. The method of claim 1, wherein said arteries and other soft tissues is arteries.

3. The method of claim 1, wherein said mammal is a non-human mammal.

4. The method of claim 1, wherein said mammal is a human.

5. The method of claim 1, wherein said control is a blood sample from the same species of mammal where said same species of mammal is a normal healthy mammal.

6. The method of claim 1, wherein said detecting comprises detecting the amount of fetuin in a sample of the fetuin mineral complex.

7. The method of claim 1, wherein said detecting comprises detecting the amount of matrix Gla protein in a sample of the fetuin mineral complex.

8. The method of claim 1, wherein said detecting comprises detecting the amount of secreted phosphoprotein 24 in a sample of the fetuin mineral complex.

9. The method of claim 1, wherein said detecting comprises detecting the amount of platelet factor 4 in a sample of the fetuin mineral complex.

10. The method of claim 1, wherein said detecting comprises detecting the amount of calcium in a sample of the fetuin mineral complex.

11. The method of claim 1, wherein said detecting comprises detecting the amount of phosphate in a sample of the fetuin mineral complex.

12. The method of claim 1, wherein said detecting comprises detecting the amount of a mineral phase in a sample of the fetuin mineral complex.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Ala Pro Gln Gly Ala Gly Leu Gly Phe Arg
1               5                   10
```